US012146136B2

(12) United States Patent
Khvorova et al.

(10) Patent No.: US 12,146,136 B2
(45) Date of Patent: Nov. 19, 2024

(54) SYNTHESIS OF MODIFIED OLIGONUCLEOTIDES WITH INCREASED STABILITY

(71) Applicant: UNIVERSITY OF MASSACHUSETTS, Boston, MA (US)

(72) Inventors: Anastasia Khvorova, Westborough, MA (US); Loïc Maurice René Jean Roux, Worcester, MA (US); Ken Yamada, Boston, MA (US)

(73) Assignee: UNIVERSITY OF MASSACHUSETTS, Boston, MA (US)

(*) Notice: Subject to any disclaimer, the term of this patent is extended or adjusted under 35 U.S.C. 154(b) by 0 days.

(21) Appl. No.: 17/213,852

(22) Filed: Mar. 26, 2021

(65) Prior Publication Data

US 2022/0010309 A1    Jan. 13, 2022

Related U.S. Application Data

(60) Provisional application No. 63/000,328, filed on Mar. 26, 2020.

(51) Int. Cl.
*C12N 15/113* (2010.01)
*C07H 19/067* (2006.01)
*C07H 21/02* (2006.01)

(52) U.S. Cl.
CPC ......... *C12N 15/113* (2013.01); *C07H 19/067* (2013.01); *C07H 21/02* (2013.01); *C12N 2310/314* (2013.01)

(58) Field of Classification Search
CPC ... C12N 15/113; C12N 15/231; C07H 19/067
See application file for complete search history.

(56) References Cited

U.S. PATENT DOCUMENTS

| | | | |
|---|---|---|---|
| 4,522,811 A | 6/1985 | Eppstein et al. |
| 5,328,470 A | 7/1994 | Nabel et al. |
| 5,684,143 A | 11/1997 | Gryaznov et al. |
| 5,814,014 A | 9/1998 | Elsberry et al. |
| 5,858,988 A | 1/1999 | Wang |
| 5,939,402 A | 8/1999 | Weis et al. |
| 6,025,335 A | 2/2000 | Weis et al. |
| 6,093,180 A | 7/2000 | Elsberry |
| 6,107,094 A | 8/2000 | Crooke |
| 6,168,587 B1 | 1/2001 | Bellhouse et al. |
| 6,177,403 B1 | 1/2001 | Stedman |
| 6,194,389 B1 | 2/2001 | Johnston et al. |
| 6,291,438 B1 | 9/2001 | Wang |
| 6,471,996 B1 | 10/2002 | Sokoll et al. |
| 6,472,375 B1 | 10/2002 | Hoon et al. |
| 7,459,547 B2 | 12/2008 | Zamore et al. |
| 7,723,512 B2 | 5/2010 | Manoharan et al. |
| 7,732,593 B2 | 6/2010 | Zamore et al. |
| 7,750,144 B2 | 7/2010 | Zamore et al. |
| 7,772,203 B2 | 8/2010 | Zamore et al. |
| 8,013,136 B2 | 9/2011 | Manoharan et al. |
| 8,097,752 B2 | 1/2012 | Calogeropoulou et al. |
| 8,304,530 B2 | 11/2012 | Zamore et al. |
| 8,309,704 B2 | 11/2012 | Zamore et al. |
| 8,309,705 B2 | 11/2012 | Zamore et al. |
| 8,329,892 B2 | 12/2012 | Zamore et al. |
| 8,431,544 B1 | 4/2013 | Agrawal et al. |
| 8,871,774 B2 | 10/2014 | Charifson et al. |
| 9,029,389 B2 | 5/2015 | No et al. |
| 11,820,985 B2 | 11/2023 | Khvorova et al. |
| 2001/0027251 A1 | 10/2001 | Cook et al. |
| 2003/0045705 A1* | 3/2003 | Cook ............... C07D 405/04 536/28.4 |
| 2005/0220766 A1 | 10/2005 | Amalfitano et al. |
| 2006/0078542 A1 | 4/2006 | Mah et al. |
| 2006/0105998 A1 | 5/2006 | Calogeropoulou et al. |
| 2008/0269149 A1 | 10/2008 | Bowles et al. |
| 2009/0281299 A1 | 11/2009 | Manoharan et al. |
| 2009/0318676 A1 | 12/2009 | Manoharan et al. |
| 2010/0186103 A1 | 7/2010 | Gao et al. |
| 2010/0240730 A1 | 9/2010 | Beigelman et al. |
| 2011/0086905 A1 | 4/2011 | Glazer |
| 2012/0136039 A1 | 5/2012 | Aronin et al. |
| 2013/0345218 A1 | 12/2013 | Charifson et al. |
| 2014/0005192 A1 | 1/2014 | Charifson et al. |
| 2014/0005197 A1 | 1/2014 | Charifson et al. |
| 2014/0155387 A1 | 6/2014 | No et al. |
| 2014/0296486 A1 | 10/2014 | Gao et al. |
| 2016/0355808 A1 | 12/2016 | Khvorova et al. |

(Continued)

FOREIGN PATENT DOCUMENTS

| | | |
|---|---|---|
| CN | 107980062 A | 5/2018 |
| EP | 3277814 A1 | 2/2018 |

(Continued)

OTHER PUBLICATIONS

International Preliminary Report on Patentability for PCT International Patent Application No. PCT/US2021/034290, pp. 1-7 (Year: 2021).*
Yamana et al. Nucleic Acids Research vol. 27, 2387-2392 (Year: 1999).*
PubChem CID 16131506 retrieved online from https://pubchem.ncbi.nlm.nih.gov/compound/16131506, pp. 1-11 (Year: 2021).*
Roy et al. Molecules 18, 14268-14284, 17 pages (Year: 2013).*
Rejman et al. Nucleosides, Nucleotides, Nucleic Acids 20, 819-823, pp. 1-6 (Year: 2001).*
Strajbl et al. Journal of Biomolecular Structure & Dynamics 13, 687-694, pp. 1-9 (Year: 1996).*
Alterman et al., "A divalent siRNA chemical scaffold for potent and sustained modulation of gene expression throughout the central nervous system", Nat Biotechnol., Aug. 2019, 37(8): 884-894.
Etzold et al., "The extension of the sugar chain of thymidine: a new route to 5'-deoxyhexose nucleosides", Chemical Communications (London), 1968, Issue 7.

(Continued)

*Primary Examiner* — Brian Whiteman
(74) *Attorney, Agent, or Firm* — LATHROP GPM LLP; James H. Velema, Esq.; Michael J. Spellberg, Esq.

(57) ABSTRACT

This disclosure relates to the synthesis of novel modified oligonucleotides. The synthesis of novel phosphoramidites are also provided.

17 Claims, 24 Drawing Sheets

Specification includes a Sequence Listing.

(56) References Cited

U.S. PATENT DOCUMENTS

| | | |
|---|---|---|
| 2017/0051286 A1 | 2/2017 | Smith |
| 2017/0312367 A1 | 11/2017 | Alterman et al. |
| 2018/0094263 A1 | 4/2018 | Alterman et al. |
| 2020/0385740 A1 | 12/2020 | Khvorova |
| 2022/0010309 A1 | 1/2022 | Khvorova |
| 2024/0141362 A1 | 5/2024 | Khvorova |

FOREIGN PATENT DOCUMENTS

| | | | |
|---|---|---|---|
| EP | 3946369 | A2 | 2/2022 |
| EP | 4126040 | A2 | 2/2023 |
| JP | H06-41183 | A | 2/1994 |
| JP | 2018-516091 | A | 6/2018 |
| WO | WO 1992/013869 | A1 | 8/1992 |
| WO | WO 1994/022890 | A1 | 10/1994 |
| WO | WO 1996/003500 | A1 | 2/1996 |
| WO | WO 2003/029459 | A2 | 4/2003 |
| WO | WO 2004/108956 | A1 | 12/2004 |
| WO | WO 2005/078095 | A1 | 8/2005 |
| WO | WO 2010/033247 | A2 | 3/2010 |
| WO | WO 2010/118263 | A1 | 10/2010 |
| WO | WO 2011/097643 | A1 | 8/2011 |
| WO | WO 2011/125943 | A1 | 10/2011 |
| WO | WO 2012/131365 | A1 | 10/2012 |
| WO | WO 2014/201306 | A1 | 12/2014 |
| WO | WO 2015/113004 | A2 | 7/2015 |
| WO | WO 2016/161374 | A1 | 10/2016 |
| WO | WO 2018/041973 | A1 | 3/2018 |
| WO | WO 2018/223056 | A1 | 12/2018 |
| WO | WO 2020/033899 | A1 | 2/2020 |
| WO | WO 2020/198509 | A2 | 10/2020 |
| WO | WO 2021/195533 | A2 | 11/2021 |

OTHER PUBLICATIONS

International Preliminary Report on Patentability for PCT International Patent Application No. PCT/US2020/025017, dated Sep. 28, 2021.

International Preliminary Report on Patentability for PCT International Patent Application No. PCT/US2019/046013, dated Apr. 28, 2020.

International Search Report and Written Opinion for PCT International Patent Application No. PCT/US2021/024425, dated Oct. 15, 2021.

International Search Report and Written Opinion for PCT International Patent Application No. PCT/US2020/025017, dated Sep. 18, 2020.

International Search Report and Written Opinion for PCT International Patent Application No. PCT/US2019/046013, dated Jan. 9, 2020.

Kachare et al., "Phospho-carboxylic anhydride of a homologated nucleoside leads to primer degradation in the presence of a polymerase", Bioorg Med Chem Letters, Jun. 15, 2014, 24(12): 2720-2723.

Mikhailov et al., "Use of 5-deoxy-ribo-hexofuranose derivatives for the preparation of 5'-nucleotide phosphonates and homoribonucleosides", Collect Czech Chem Commun., 1989, 54(4): 1055-1066.

Ohtsuka et al., "Joining of synthetic ribotrinucleotides with defined catalyzed by T4 RNA ligase", European Journal of Biochemistry, 1977, 81(2): 285-291.

Padiukova et al., "Synthesis of 5'-derivatives of thymidine", Bioorg Khim., 1990, 16(5): 668-673 [Article in Russian—no abstract available].

Rozners et al., "Synthesis and Properties of RNA Analogues Having Amides as Interuridine Linkages at Selected Positions", JACS Articles, Sep. 6, 2003, 125: 12125-12136.

Schlegal et al., "Chirality Dependent Potency Enhancement and Structural Impact of Glycol Nucleic Acid Modification on siRNA", JACS, Jun. 1, 2017, pp. 1-28.

Shukla et al., "Exploring Chemical Modifications for siRNA Therapeutics: A Structural and Functional Outlook", ChemMedChem, Feb. 19, 2010, 5(3): 328-349.

Sípová et al., "5'-O-Methylphosphonate nucleic acids—new modified DNAs that increase the *Escherichia coli* RNase H cleavage rate of hybrid duplexes", Nucleic Acids Research, 2014, 42(8): 5378-5389.

Bertram et al., "Vinylphosphonate Internucleotide Linkages Inhibit the Activity of PcrA DNA Helicase", Biochemistry, Jun. 18, 2002, 41(24): 7725-7731.

Collis et al., "The synthesis of vinylphosphonate-linked RNA", Thesis, Feb. 2008, Retrieved from url: https://core.ac.uk/download/pdf/33564036.pdf.

Crooke, et al., "Phosphorothioate Modified Oligonucleotide-Protein Interactions", Nucleic Acids Research, 48(10): 5235-5253, May 1, 2020.

Dua et al., "Modified siRNA Structure With a Single Nucleotide Bulge Overcomes Conventional siRNA-mediated Off-target Silencing", Molecular Therapy, Jun. 2011, 16(9): 1676-1687.

Extended European Search Report for European Patent Application No. 20777915.8, mailed Apr. 5, 2023.

Extended Supplementary European Search Report for European Patent Application No. 20777915.8, mailed Sep. 15, 2023.

Ghidini et al., "An RNA modification with remarkable resistance to RNase A", Chemical Communications, Aug. 8, 2013, 49: 9036-9038.

Haly et al., "An Extended Phosphate Linkage: Synthesis, Hybridization and Modeling Studies of Modified Oligonucleotides", Nucleosides and Nucleotides, 1996, 15(7-8): 1383-1395.

Hanus et al., "-CH2- lengthening of the internucleotide linkage in the ApA dimer can improve its conformational compatibility with its natural polynucleotide counterpart", Nucleic Acids Research, Dec. 15, 2001, 29(24): 5182-5194.

International Search Report and Written Opinion for PCT International Patent Application No. PCT/US2021/034290, mailed Nov. 4, 2021.

Kofoed et al., "Oligodeoxynucleotides with Extended 3'- and 5'-Homologous Internucleotide Linkages", Acta Chemica Scandanavia, 1997, 51: 318-324.

Magner et al., "Influence of mismatched and bulged nucleotides on SNP- preferential RNase H cleavage of RNA-antisense gapmer heteroduplexes", Scientific Reports, Oct. 2017, 7(12532), 16 pages.

Mazur et al., "Isosteres of natural phosphates. 11. Synthesis of a phosphonic acid analogue of an oligonucleotide", Tetrahedron, 1984, 40(20): 3949-3956.

Namjou et al., "GWAS and enrichment analyses of non-alcoholic fatty liver disease identify new trait-associated genes and pathways across eMERGE Network", BMC Medicine, Jul. 2019, 17: 135, 19 pages.

Noguchi et al., "Allele-specific Gene Silencing of Mutant mRNA Restores Cellular Function in Ullrich Congenital Muscular Dystrophy Fibroblasts", Molecular Therapy-Nucleic Acids, Jun. 2014, 3: e171.

Partial Supplementary European Search Report for European Patent Application No. 20852443.9, mailed Aug. 25, 2023.

Schwarz et al., "Designing siRNA that distinguish between genes that differ by a single nucleotide", Plos Genetics, Sep. 2006, 2(9): e140.

Sibley et al., "Identification of Allele-Specific RNAi Effectors Targeting Genetic Forms of Parkinson's Disease", PLOS One, Oct. 2011, 6(10): e26194.

You et al., "Design of LNA probes that improve mismatch discrimination", Nucleic Acids Research, May 2006, 34(8): e60, 11 pages.

Alisky, et al., Gene Therapy for Amyotrophic Lateral Sclerosis and Other Motor Neuron Diseases, Human Gene Therapy, vol. 11, Issue 17, pp. 2315-2329, Nov. 20, 2000.

Alterman, et al., Hydrophobically Modified siRNAs Silence Huntingtin mRNA in Primary Neurons and Mouse Brain, Molecular Therapy-Nucleic Acids, vol. 4, pp. e266, Dec. 1, 2015.

Alvarez-Erviti, et al., Delivery of siRNA To The Mouse Brain By Systemic Injection Of Targeted Exosomes, Nature Biotechnology, vol. 29, No. 4, pp. 341-345, Apr. 2011.

(56) References Cited

OTHER PUBLICATIONS

Atwell, et al., Stable Heterodimers From Remodeling The Domain Interface Of A Homodimer Using A Phage Display Library, Journal Of Molecular Biology, vol. 270, Issue 1, pp. 26-35, Jul. 4, 1997.
Baker et al., Searching for the ideal triazole: Investigating the 1,5-triazole as a charge neutral DNA backbone mimic, Tetrahedron, Dec. 31, 2019, 76(7): 1-11.
Billy, et al., Specific Interference With Gene Expression Induced By Long, Double-Stranded RNA In Mouse Embryonal Teratocarcinoma Cell Lines, Proceedings of the National Academy of Sciences, vol. 98, No. 25, pp. 14428-14433, Dec. 4, 2001.
Braasch, et al., RNA Interference in Mammalian Cells by Chemically-Modified RNA, Biochemistry, vol. 42, No. 26, pp. 7967-7975, Jun. 11, 2003.
Brummelkamp, et al., A System for Stable Expression of Short Interfering RNAs in Mammalian Cells, Science, vol. 296, Issue 5567, pp. 550-553, Apr. 19, 2002.
Chen, et al., Gene Therapy For Brain Tumors: Regression Of Experimental Gliomas By Adenovirus-Mediated Gene Transfer In Vivo, Proceedings of the National Academy of Sciences, vol. 91, No. 8, pp. 3054-3057, 1994.
Davidson, et al., A Model System For In Vivo Gene Transfer Into The Central Nervous System Using An Adenoviral Vector, Nature Genetics, vol. 3, No. 3, pp. 219-223, Mar. 1, 1993.
Davidson, et al., Recombinant Adeno-Associated Virus Type 2, 4, and 5 Vectors: Transduction of Variant Cell Types And Regions In The Mammalian Central Nervous System, Proceedings of the National Academy of Sciences, vol. 97, No. 7, pp. 3428-3432, Mar. 28, 2000.
De Mesmaeker et al., Replacement of the Phosphodiester Linkage in Oligonucleotides by an Amide: Effect of Backbone Length on Duplex Stability with RNA Complement, Bioorganic & Medicinal Chemistry Letters, Feb. 18, 1997, 7(4): 447-452.
Eckstein, Phosphorothioate Oligodeoxynucleotides: What Is Their Origin and What Is Unique About Them?, Antisense and Nucleic Acid Drug Development, vol. 10, Issue 2, pp. 117-121, Jan. 30, 2009.
Egusquiaguirre, et al., Nanoparticle Delivery Systems For Cancer Therapy: Advances In Clinical And Preclinical Research, Clinical and Translational Oncology, vol. 14, pp. 83-93, 2012.
El Andaloussi, et al., Exosome-Mediated Delivery of siRNA In Vitro And In Vivo, Nature Protocols, vol. 7, No. 12, pp. 2112-2126, Nov. 15, 2012.
El Andaloussi, et al., Exosomes For Targeted siRNA Delivery Across Biological Barriers, Advanced Drug Delivery Reviews, vol. 65, pp. 391-397, 2013.
El Andaloussi, et al., Extracellular Vesicles: Biology And Emerging Therapeutic Opportunities, Nature Reviews Drug Discovery, vol. 12, pp. 347-357, May 2013.
Elmen, et al., Locked Nucleic Acid (LNA) Mediated Improvements in siRNA Stability And Functionality, Nucleic Acids Research, vol. 33, Issue 1, pp. 439-447, Jan. 14, 2005.
Fattal, et al., Biodegradable Polyalkylcyanoacrylate Nanoparticles For The Delivery Of Oligonucleotides, Journal of Controlled Release, vol. 53, pp. 137-143, May 1998.
Fisher, et al., Transduction With Recombinant Adeno-Associated Virus For Gene Therapy Is Limited By Leading-Strand Synthesis, Journal of virology, vol. 70, No. 1, pp. 520-532, Jan. 1996.
Godard, et al., Antisense Effects of Cholesterol-Oligodeoxynucleotide Conjugates Associated with Poly(alkylcyanoacrylate) Nanoparticles, European Journal of Biochemistry banner, vol. 232, pp. 404-410, 1995.
Hamajima, et al., Intranasal Administration of HIV-DNA Vaccine Formulated with a Polymer, Carboxymethylcellulose, Augments Mucosal Antibody Production and Cell-Mediated Immune Response, Clinical Immunology and Immunopathology, vol. 88, Issue 2, pp. 205-210, Aug. 1998.
Haraszti, et al., 5'-Vinylphosphonate improves tissue accumulation and efficacy of conjugated siRNAs in vivo, Nucleic Acids Research, Jul. 27, 2017, 45(13): 7581-7592.
Herdewijn, Heterocyclic Modifications of Oligonucleotides and Antisense Technology, Antisense and Nucleic Acid Drug Development, vol. 10, Issue 4, pp. 297-310, Jul. 8, 2004.
Karlin, et al., Applications And Statistics For Multiple High-Scoring Segments In Molecular Sequences, Proceedings of the National Academy of Sciences of the USA, vol. 90, pp. 5873-5877, Jun. 1993.
Karlin, et al., Methods For Assessing The Statistical Significance Of Molecular Sequence Features By Using General Scoring Schemes, Proceedings of the National Academy of science of the USA, vol. 87, No. 6, pp. 2264-2268, Mar. 1990.
Lagos-Quintana, et al., Identification of Novel Genes Coding for Small Expressed RNAs, Science, vol. 294, Issue 5543, pp. 853-858, Oct. 26, 2001.
Lagos-Quintana, et al., Identification of Tissue-Specific MicroRNAs from Mouse, Current Biology, vol. 12, Issue 9, pp. 735-739, Apr. 30, 2002.
Lam, et al., "A New Type of Synthetic Peptide Library For Identifying Ligand-Binding Activity", Nature, vol. 354, pp. 82-84, Nov. 7, 1991.
Lambert, et al., Nanoparticulate Systems For The Delivery Of Antisense Oligonucleotides, Advanced Drug Delivery Reviews, vol. 47, pp. 99-112, 2001.
Lee, et al., Recent Developments In Nanoparticle-Based siRNA Delivery For Cancer Therapy, BioMed Research International, vol. 2013, Article ID 782041, 10 Pages, Jun. 2013.
Lim, et al., Vertebrate MicroRNA Genes, Science, vol. 299, Issue 5612, p. 1540, Mar. 7, 2003.
Liu et al., Phosphonomethyl Oligonucleotides as Backbone-Modified Artificial Genetic Polymers, Journal of the American Chemical Society, May 3, 2018, 140(21): 6690-6699.
McCaffrey, et al., Gene Expression: RNA Interference in Adult Mice, Nature, vol. 418, No. 6893, pp. 38-39, Jul. 4, 2002.
Miyagishi, et al., U6 promoter-driven siRNAs With Four Uridine 3' Overhangs Efficiently Suppress Targeted Gene Expression In Mammalian Cells, Nature Biotechnology, vol. 20, No. 5, pp. 497-500, May 1, 2002.
Nielsen, et al., Sequence-Selective Recognition of DNA by Strand Displacement With A Thymine-Substituted Polyamide, Science, vol. 254, Issue 5037, pp. 1497-1500, Dec. 6, 1991.
Partial European Search Report for European Patent Application No. 21776020.6, dated Apr. 5, 2024.
Pav et al., Synthesis of oligoribonucleotides with phosphonate-modified linkages, Organic & Biomolecular Chemistry, Jan. 1, 2011, 9(17): 6120.
Pav et al., Tuning the hybridization properties of modified oligonucleotides: from flexible to conformationally constrained phosphonate internucleotide linkages, Organic & Biomolecular Chemistry, Jan. 1, 2017, 15(3): 701-707.
Petersen, et al., Lna: A Versatile Tool for Therapeutics and Genomics, Trends in Biotechnology, vol. 21, Issue 2, pp. 74-81, Feb. 2003.
Putnam, David A., Antisense Strategies and Therapeutic Applications, American Journal of Health System Pharmacy, vol. 53, No. 2, pp. 151-160, Jan. 15, 1996.
Rejman et al., Oligonucleotides with Isopolar Phosphonate Internucleotide Linkage: A New Perspective for Antisense Compounds?, Nucleosides, Nucleotides & Nucleic Acids, Apr.- Jul. 2001, 20(4-7): 819-823.
Rusckowski, et al., Biodistribution and Metabolism of a Mixed Backbone Oligonucleotide (GEM 231) Following Single and Multiple Dose Administration in Mice, Antisense and Nucleic Acid Drug Development, vol. 10, Issue 5, pp. 333-345, Jan. 30, 2009.
Schwab, et al., An Approach For New Anticancer Drugs:Oncogene-Targeted Antisense DNA, Annals of Oncology, vol. 5, Issue 4, pp. 55-58, 1994.
Sipova et al., 5'-O-Methylphosphonate nucleic acids-new modified DNAs that increase the Escherichia coli RNase H cleavage rate of hybrid duplexes, Nucleic Acids Research, Feb. 12, 2014, 42(8): 5378-5389.
Stein, et al., Inhibition of Vesivirus Infections in Mammalian Tissue Culture with Antisense Morpholino Oligomers, Antisense and Nucleic Acid Drug Development, vol. 11, Issue 5, pp. 317-325, Oct. 2001.

(56) References Cited

OTHER PUBLICATIONS

Stein, et al., Systemic and Central Nervous System Correction of Lysosomal Storage in Mucopolysaccharidosis Type VII Mice, Journal of Virology, vol. 73, No. 4, pp. 3424-3429, Apr. 1999.
Vorobjev, et al., Nuclease Resistance and RNase H Sensitivity of Oligonucleotides Bridged by Oligomethylenediol and Oligoethylene Glycol Linkers, Antisense and Nucleic Acid Drug Development, vol. 11, No. 2, pp. 77-85, Apr. 2011.
Wang, et al., Nanoparticle-Based Delivery System for Application of siRNA In Vivo, Current Drug Metabolism, vol. 11, No. 2, pp. 182-196, 2010.
Wright, et al., Identification Of Factors That Contribute To Recombinant AAV2 Particle Aggregation And Methods To Prevent Its Occurrence During Vector Purification And Formulation, Molecular Therapy, vol. 12, Issue 1,, pp. 171-178, Jul. 2005.
Xia, et al., siRNA-Mediated Gene Silencing in Vitroand In Vivo, Nature Biotechnology, vol. 20, No. 10, pp. 1006-1010, Sep. 16, 2002.
Yuan, et al., Recent Advances of siRNA Delivery By Nanoparticles, Expert Opinion on Drug Delivery vol. 8, Issue 4, pp. 521-536, 2011.
Zhang, et al., Several rAAV Vectors Efficiently Cross the Blood-brain Barrier and Transduce Neurons and Astrocytes in the Neonatal Mouse Central Nervous System, Molecular Therapy, vol. 19, Issue 8, pp. 1440-1448, Aug. 1, 2011.
U.S. Appl. No. 16/831,470, filed Mar. 26, 2020 U.S. Pat. No. 11,820,985, Nov. 21, 2023, Anastasia Khvorova.
U.S. Appl. No. 17/213,852, filed Mar. 26, 2021, Anastasia Khvorova.
U.S. Appl. No. 18/459,992, filed Sep. 1, 2023, Anastasia Khvorova.
U.S. Appl. No. 18/417,565, filed Jan. 19, 2024, Anastasia Khvorova.

\* cited by examiner

Examples of exNA-modified RNA oligonucleotides

| Name | Sequence (5' -> 3') |
|---|---|
| Themo-ex1a | (rC)(rG)(rC)(rA)(rU)(ex-rU)(rA)(rG)(rC)(rG) |
| Themo-ex1b | (rC)(rG)(rC)(rA)(rU)(ex-rU)(rA)(rG)(rC)(rG) |
| Themo-ex2 | (rC)(rG)(rC)(rA)(rG)(ex-rU)(rA)(rG)(rC)(rG) |
| Themo-ex3 | (rC)(rG)(rC)(rA)(rC)(ex-rU)(rA)(rG)(rC)(rG) |
| Themo-ex4 | (rC)(rG)(rC)(rA)(rC)(ex-rU)(rA)(rG)(rC)(rG) |
| UC-seq-ex1 | (rU)(rC)(rC)(rU)(rC)(ex-rU)(rU)(rC)(rC)(rU) |
| UC-seq-ex2 | (rU)(rC)(rU)(rC)(ex-rU)(ex-rU)(rU)(rC)(rC)(rU) |
| UC-seq-ex3 | (ex-rU)(rC)(ex-rU)(rC)(ex-rU)(rU)(ex-rU)(rC)(ex-rU)(rC)(ex-rU) |

(rN): 2'-OH ribonucleoside, (ex-rU):exNA ribo-uridine

FIG. 13

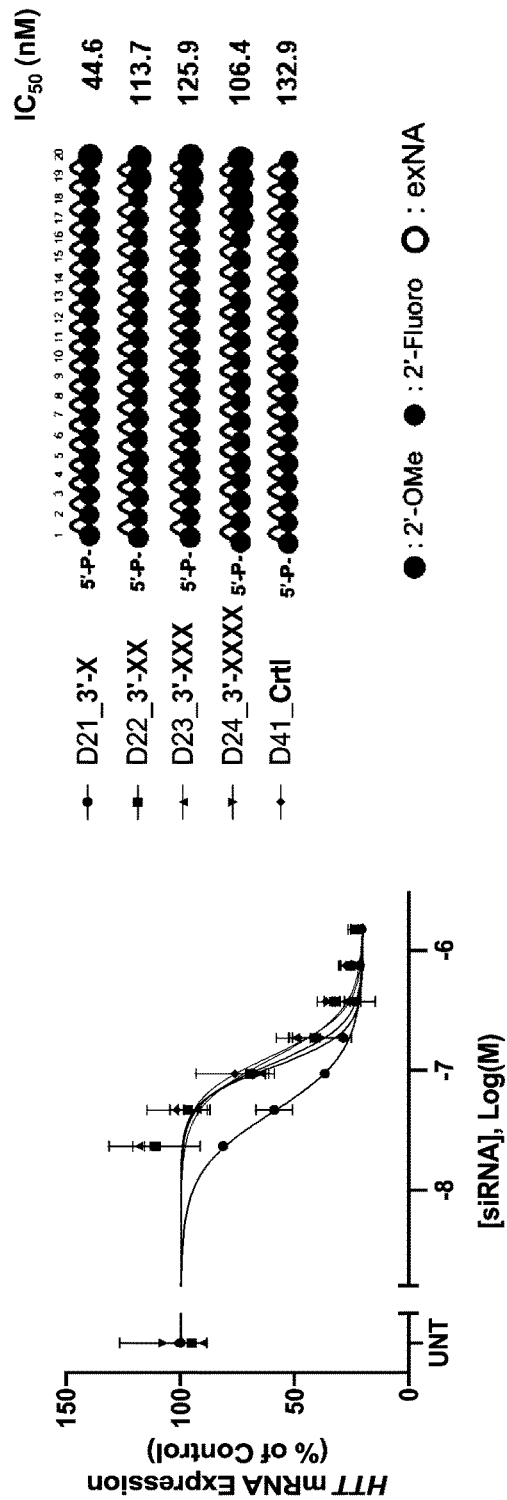
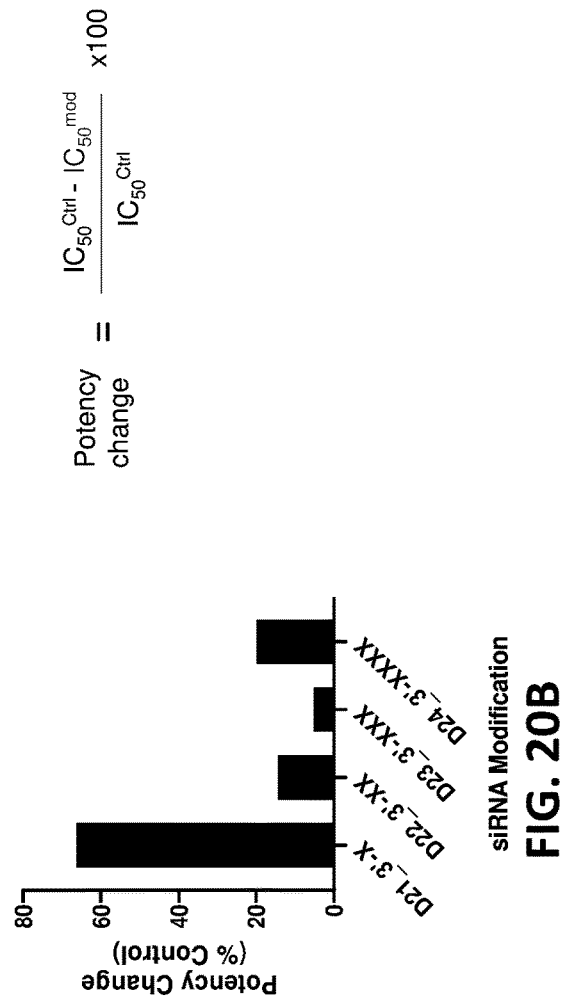
FIG. 20A
FIG. 20B

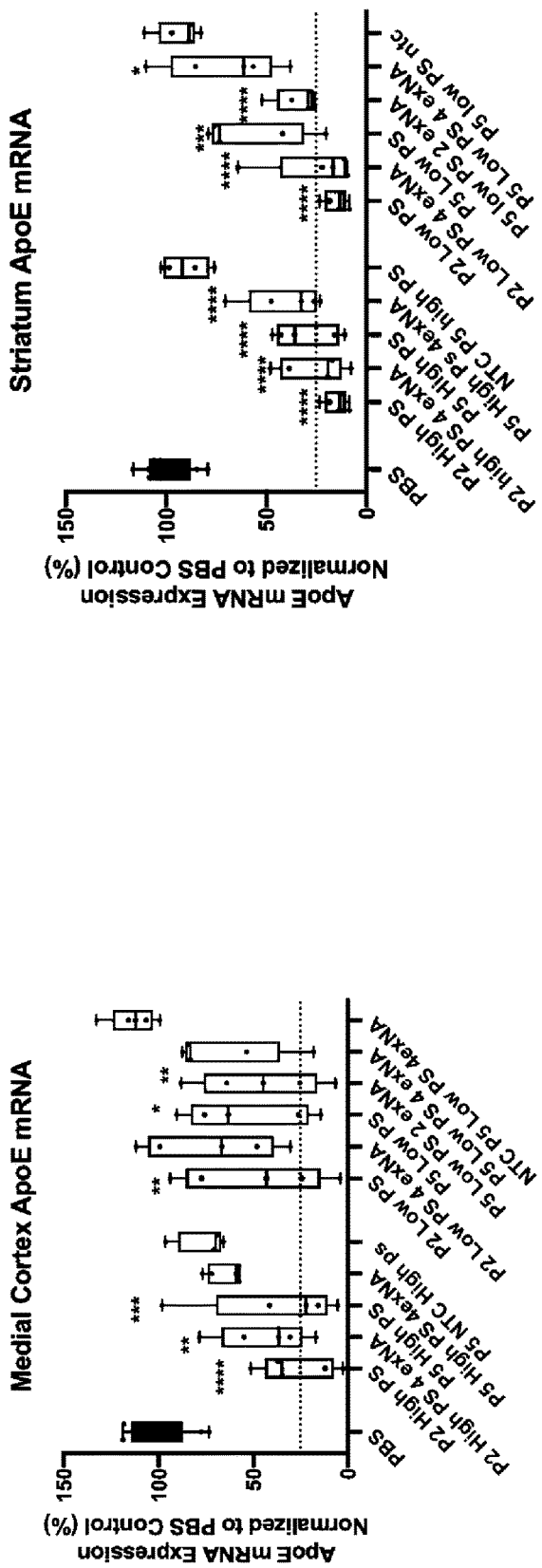
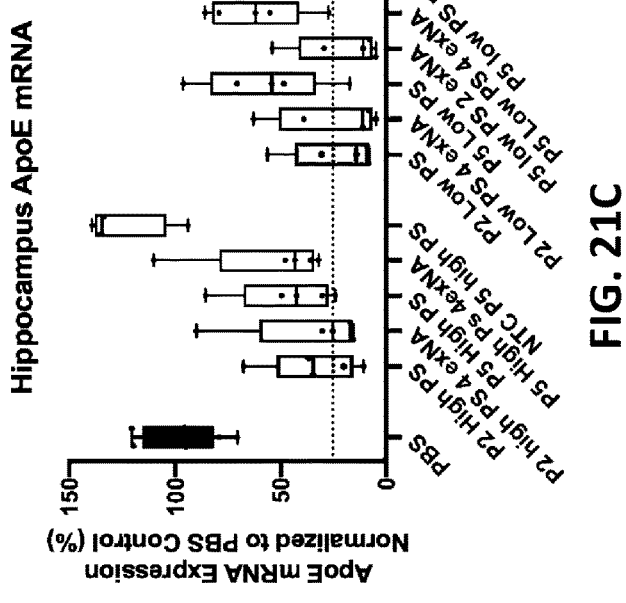
FIG. 21A
FIG. 21B
FIG. 21C

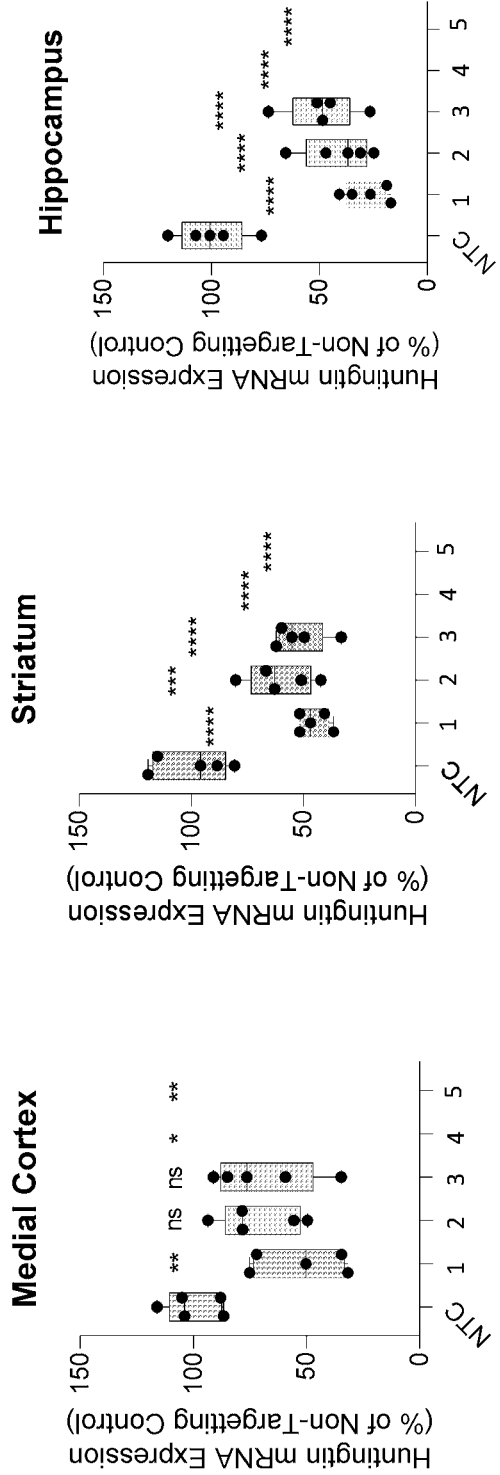
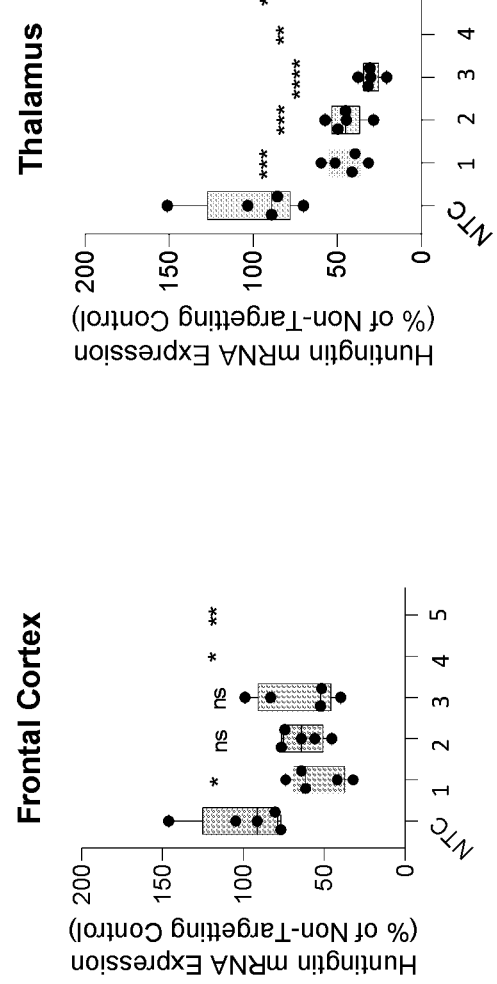
FIG. 22A, FIG. 22B, FIG. 22C, FIG. 22D, FIG. 22E

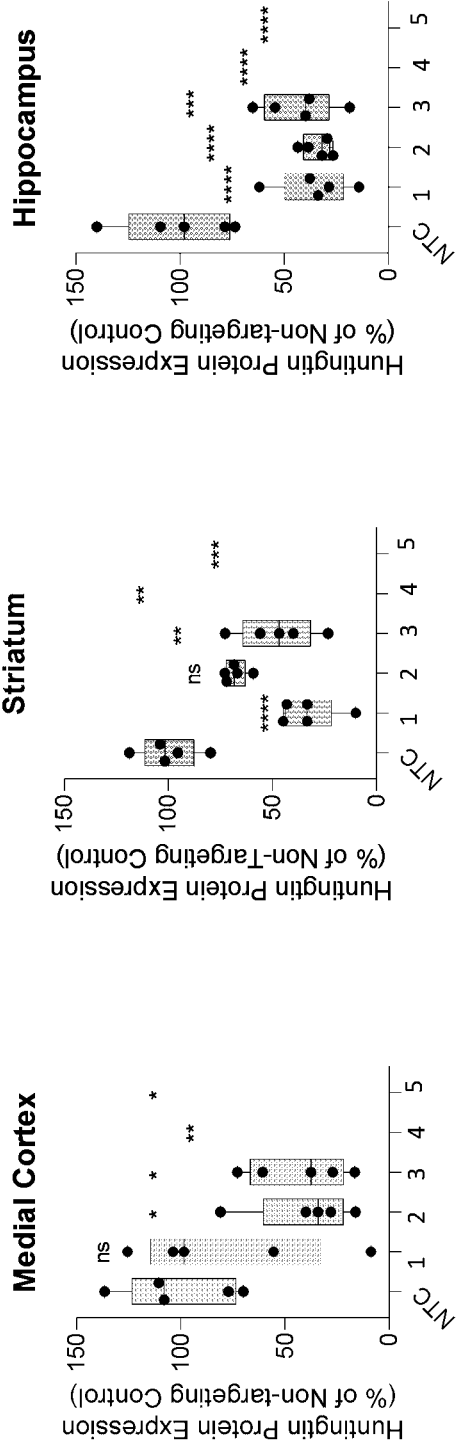
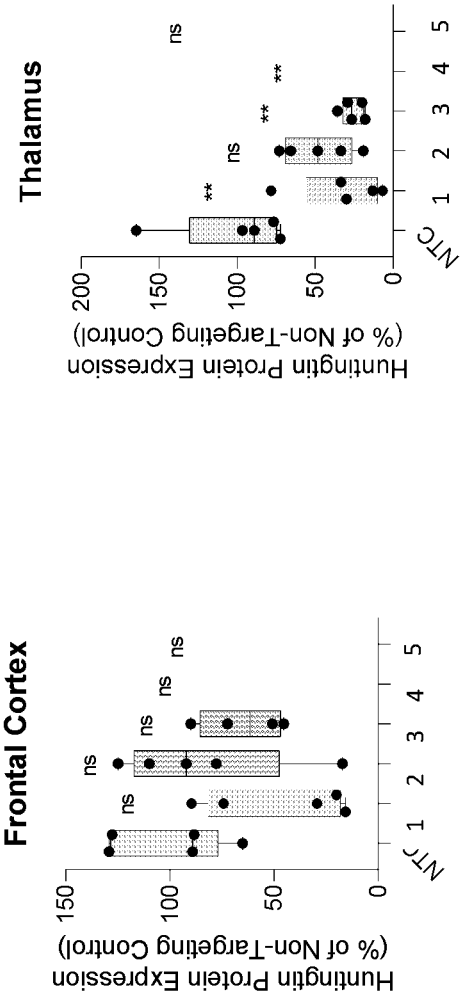

SEQUENCE LISTING

<160> NUMBER OF SEQ ID NOS: 89

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uuaaucucuu uacugauaua                                               20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uuaaucucuu uacugauaua                                               20

<210> SEQ ID NO 3
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uuuuuaaauc cugagaagaa                                               20

<210> SEQ ID NO 4
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uuuuuaaauc cugagaagaa                                               20

<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uuaaucucuu uacugauaua                                               20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uccacuaugu uuucacauau                                               20

```
<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uuaaucucuu uacugauaua                                                    20

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uccacuaugu uuucacauau                                                    20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uuaaucucuu uacugauaua                                                    20

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uuaaucucuu uacugauaua                                                    20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uuaaucucuu uacugauaua                                                    20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
uccacuaugu uuucacauau                                                    20
```

```
<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uccacuaugu uuucacauau                                                   20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uuaaucucuu uacugauaua                                                   20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ugccuaagag cacauuuagu                                                   20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
ugccuaagag cacauuuagu                                                   20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
uuaaucucuu uacugauaua                                                   20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uccacuaugu uuucacauau                                                   20
```

```
<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uuaaucucuu uacugauaua                                                      20

<210> SEQ ID NO 20
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uccacuaugu uuucacauau                                                      20

<210> SEQ ID NO 21
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ugaaaacaua gugga                                                           15

<210> SEQ ID NO 22
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
cucaggauuu aaaaa                                                           15

<210> SEQ ID NO 23
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aauguuguga ccgga                                                           15

<210> SEQ ID NO 24
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
caguaaagag auuaa                                                           15

<210> SEQ ID NO 25
```

```
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aauguuguga ccgga                                                    15

<210> SEQ ID NO 26
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
aauguuguga ccgga                                                    15

<210> SEQ ID NO 27
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
augugcucuu aggca                                                    15

<210> SEQ ID NO 28
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
cucaggauuu aaaaa                                                    15

<210> SEQ ID NO 29
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
cucaggauuu aaaaa                                                    15

<210> SEQ ID NO 30
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cucaggauuu aaaaa                                                    15

<210> SEQ ID NO 31
<211> LENGTH: 15
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
cuggaaaagc ugaua                                                     15

<210> SEQ ID NO 32
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
caguaaagag auuaa                                                     15

<210> SEQ ID NO 33
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
caguaaagag auuaa                                                     15

<210> SEQ ID NO 34
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
cuggaaaagc ugaua                                                     15

<210> SEQ ID NO 35
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
caguaaagag auuau                                                     15

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
uuaaucucuu uacugauuuu                                                20

<210> SEQ ID NO 37
<211> LENGTH: 20
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 37
uuaaucucuu uacugauaua                                                   20

<210> SEQ ID NO 38
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uuaaucucuu uacugauuuu                                                   20

<210> SEQ ID NO 39
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
uuuuuaaauc cugagaagaa                                                   20

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uccacuaugu uuucacauau                                                   20

<210> SEQ ID NO 41
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ugccuaagag cacauuuagu                                                   20

<210> SEQ ID NO 42
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uaucagcuuu uccagggucg                                                   20

<210> SEQ ID NO 43
<211> LENGTH: 20
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 43
uccggucaca acauuguggu                                                 20

<210> SEQ ID NO 44
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
auaaucucuu uacugauaua                                                 20

<210> SEQ ID NO 45
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
caguaaagag auuaa                                                      15

<210> SEQ ID NO 46
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
cucaggauuu aaaaa                                                      15

<210> SEQ ID NO 47
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ugaaaacaua gugga                                                      15

<210> SEQ ID NO 48
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
augugcucuu aggca                                                      15

<210> SEQ ID NO 49
<211> LENGTH: 15
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 49
cuggaaaagc ugaua                                                      15

<210> SEQ ID NO 50
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
aauguuguga ccgga                                                      15

<210> SEQ ID NO 51
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
caguaaagag auuau                                                      15

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uuuuuuuuuu uuuuuuuuuu                                                 20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uuuuuuuuuu uuuuuuuuuu                                                 20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uuuuuuuuuu uuuuuuuuuu                                                 20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 55
uuuuuuuuuu uuuuuuuuuu                                          20

<210> SEQ ID NO 56
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
uuuuuuuuuu uuuuuuuuuu                                          20

<210> SEQ ID NO 57
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uuuuuuuuuu uuuuuuuuuu                                          20

<210> SEQ ID NO 58
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
uuuuuuuuuu uuuuuuuuuu                                          20

<210> SEQ ID NO 59
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uuuuuuuuuu uuuuuuuuuu                                          20

<210> SEQ ID NO 60
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uuuuuuuuuu uuuuuuuuuu                                          20

<210> SEQ ID NO 61
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 61
uuuuuuuuuu uuuuuuuuuu                                          20

<210> SEQ ID NO 62
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uuuuuuuuuu uuuuuuuuuu                                          20

<210> SEQ ID NO 63
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uuuuuuuuuu uuuuuuuuuu                                          20

<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uuaaucucuu uacugauuuu                                          20

<210> SEQ ID NO 65
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uuaaucucuu uacugauuuu                                          20

<210> SEQ ID NO 66
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uuaaucucuu uacugauuuu                                          20

<210> SEQ ID NO 67
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 67
uuaaucucuu uacugauuuu                                              20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uuaaucucuu uacugauuuu                                              20

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uuggauaugg auguuguuuu u                                            21

<210> SEQ ID NO 70
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
caacauccau auccaa                                                  16

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uuggauaugg auguuguuuu u                                            21

<210> SEQ ID NO 72
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
caacauccau auccaa                                                  16

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
```
uuggauaugg auguuguuuu u 21

<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uuggauaugg auguuguuuu u 21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
uuggauaugg auguuguuuu u 21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uuggauaugg auguuguuuu u 21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
uuggauaugg auguuguuuu u 21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
uuggauaugg auguuguuuu u 21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uuggauaugg auguuguuuu u                                                         21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
uaaucguauu ugucaauuuu u                                                         21

<210> SEQ ID NO 81
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
uugacaaaua cgauua                                                               16

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
uaaucguauu ugucaauuuu u                                                         21

<210> SEQ ID NO 83
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
cgcauuagcc g                                                                    11

<210> SEQ ID NO 84
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
cgcaguagcc g                                                                    11

<210> SEQ ID NO 85
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
cgcaauagcc g                                                                    11

```
<210> SEQ ID NO 86
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
cgcacuagcc g                                                              11

<210> SEQ ID NO 87
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ucucuuucuc u                                                              11

<210> SEQ ID NO 88
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ucucuuucuc u                                                              11

<210> SEQ ID NO 89
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ucucuuucuc u                                                              11
```

SYNTHESIS OF MODIFIED OLIGONUCLEOTIDES WITH INCREASED STABILITY

CROSS-REFERENCE TO RELATED APPLICATIONS

This application claims the benefit of U.S. Provisional Application Ser. No. 63/000,328, filed Mar. 26, 2020, the entire disclosure of which is incorporated herein by reference.

STATEMENT REGARDING FEDERALLY SPONSORED RESEARCH OR DEVELOPMENT

This invention was made with government support under Grant No. GM131839 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Aug. 19, 2021, is named 715663_UM9-228CIP_ST25.txt and is 21,209 bytes in size.

FIELD OF THE INVENTION

This disclosure relates to the synthesis of novel modified oligonucleotides, and novel phosphoramidites.

BACKGROUND

Currently, the most common metabolically stable backbone modification used in complex therapeutic RNAs is the Phosphorothioate (PS) modification. While other available backbone modification alternatives, such as Peptide Nucleic Acid (PNA) and Phosphorodiamidate Morpholino Oligonucleotide (PMO), work well as steric-blocking antisense oligonucleotides, these modifications are not tolerated in many promising RNA-based therapeutic strategies. These strategies include siRNAs, miRNAs, RNaseH-dependent antisense oligonucleotides, and aptamer-based therapeutics. This poor tolerance is due to PNA's and PMO's inability to withstand biological machineries, such as Argonaute proteins (siRNA/miRNA), and RNaseH, which strictly recognize RNA structures when they form "functional" RNA-protein complexes.

One of the most popular RNA-based therapeutic strategies is the use of metabolically stable, PS-modified RNAs or PS/PO-modified chimeric oligonucleotides. A severe drawback in this strategy, however, is toxicity due to non-specific binding of the RNAs to a variety of proteins in vivo. Another drawback is that the PS-modified, and even more so, PS/PO-modified RNAs are decomposed by endogenous nucleases. Thus, additional backbone modifications that provide higher metabolic stabilization without compromising drug efficacy are urgently needed in the field of RNA therapeutics.

Synthetic accessibility is also important factor in a development of therapeutic oligonucleotides. A variety of other modified backbones have been reported (e.g. boranophosphate, phosphoroamidate, etc.) but many of those require a specific synthetic procedure, which is not always compatible with the conventional phosphoramidite oligonucleotide synthesis cycle. This makes it difficult to freely synthesize/design chimeric backbones having these modifications in a similar manner as mixing PS/PO backbone with other sugar modified backbones. This difficulty in the synthesis limits additively diversifying the designing pattern of functional therapeutic oligonucleotides. Thus, having a new chemical tool that is easy to synthesize and compatible with currently validated chemical modification is a high demand in the field.

Provided herein is a new variety of backbone modification wherein one or more carbon chains are inserted in the backbone structure. The backbone modifications provided herein are not expected to have a profound impact on the structure of RNA, and can therefore provide compatibility with a variety of RNA-binding biological machineries. Further, these modifications are not expected to display toxic, non-specific binding to proteins, and thus can be incorporated into a wide range of therapeutic RNAs.

SUMMARY

In one aspect, the disclosure provides a modified oligonucleotide comprising a 5' end, a 3' end and at least one modified intersubunit linkage of Formula I:

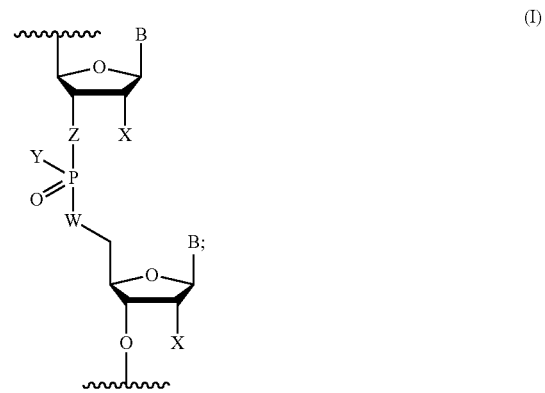

(I)

wherein:
B is a base pairing moiety;
W is O or $O(CH_2)_n$, wherein n is 1 to 10;
X is selected from the group consisting of H, OH, OR, F, SH, SR, $NR^2_2$ and $C_{1-6}$-alkoxy;
Y is selected from the group consisting of $O^-$, OH, OR, $OR^2$, $NH^-$, $NH_2$, $NR^2_2$, $BH_3$, $S^-$, $R^1$, and SH;
Z is O or $O(CH_2)_n$;
$R^1$ is alkyl, allyl or aryl; and
$R^2$ is alkyl, allyl or aryl.

In an embodiment of Formula I, Z is $O(CH_2)_n$, n is 1, W is O, and Y is $O^-$.

In an embodiment of Formula I, Z is O, W is $O(CH_2)_n$, n is 1, and Y is $O^-$.

In an embodiment of Formula I, Z is $O(CH_2)_n$, n is 1, W is O, and Y is $O^-$.

In an embodiment of Formula I, Z is $O(CH_2)_n$, n is 1, W is $O(CH_2)_n$, and Y is $O^-$.

In an embodiment of Formula I, Z is $O(CH_2)_n$, n is not 1, W is $O(CH_2)_n$, and Y is $O^-$.

In an embodiment of Formula I, the base pairing moiety B is selected from the group consisting of adenine, guanine, cytosine, and uracil.

In another aspect, the disclosure provides a modified oligonucleotide comprising a 5' end, a 3' end and at least one modified intersubunit linkage of Formula II:

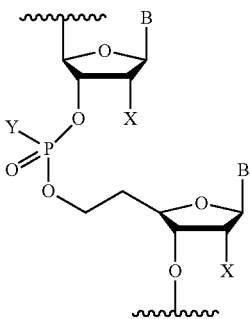

(II)

wherein:
B is a base pairing moiety;
X is selected from the group consisting of H, OH, OR, F, SH, SR, $NR^2_2$ and $C_{1-6}$-alkoxy;
Y is selected from the group consisting of $O^-$, OH, OR, $OR^2$, $NH^-$, $NH_2$, $NR^2_2$, $BH_3$, $S^-$, $R^1$, and SH;
$R^1$ is alkyl, allyl or aryl; and
$R^2$ is alkyl, allyl or aryl.

In an embodiment of Formula II, Y is O.

In an embodiment of Formula II, the base pairing moiety B is selected from the group consisting of adenine, guanine, cytosine, and uracil.

In another aspect, the disclosure provides modified oligonucleotide comprising a 5' end, a 3' end and at least one modified intersubunit linkage of Formula III:

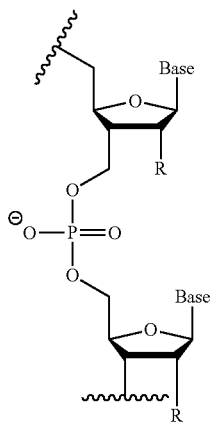

(III)

wherein:
B is a base pairing moiety;
R is alkyl, allyl or aryl.

In an embodiment of Formula III, Y is O.

In an embodiment of Formula III, the base pairing moiety B is selected from the group consisting of adenine, guanine, cytosine, and uracil.

In another aspect, the disclosure provides a modified oligonucleotide comprising a 5' end, a 3' end and at least one modified intersubunit linkage of Formula IV:

(IV)

wherein:
B is a base pairing moiety;
R is alkyl, allyl or aryl.

In an embodiment of Formula IV, the base pairing moiety B is selected from the group consisting of adenine, guanine, cytosine, and uracil.

In another aspect, the disclosure provides modified oligonucleotide comprising a 5' end, a 3' end and at least one modified intersubunit linkage of Formula V:

(V)

wherein:
B is a base pairing moiety;
R is alkyl, allyl or aryl.

In an embodiment of Formula V, the base pairing moiety B is selected from the group consisting of adenine, guanine, cytosine, and uracil.

In another aspect, the disclosure provides modified oligonucleotide comprising a 5' end, a 3' end and at least one modified intersubunit linkage of Formula VI:

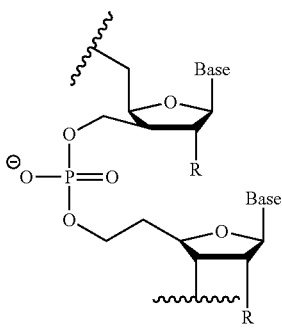

(VI)

wherein:
B is a base pairing moiety;
R is alkyl, allyl or aryl.

In an embodiment of Formula VI, the base pairing moiety B is selected from the group consisting of adenine, guanine, cytosine, and uracil.

In another aspect, the disclosure provides a phosphoramidite derivative of Formula (VII):

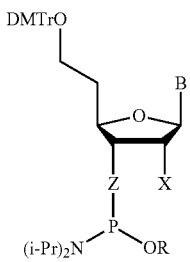

(VII)

wherein:
B is a base pairing moiety;
X is selected from the group consisting of H, OH, OR, F, SH, SR, $NR^2_2$, MOE, alkyl, allyl, aryl, and $C_{1-6}$-alkoxy;
Z is O or $OCH_2$:
R is OMe or OCE (cyanoethyl):
$R^1$ is alkyl, allyl or aryl; and
$R^2$ is alkyl, allyl or aryl.

In an embodiment of Formula VII, the base pairing moiety B is selected from the group consisting of adenine, guanine, cytosine, and uracil.

In another aspect, the disclosure provides a phosphoramidite derivative of Formula (VIII):

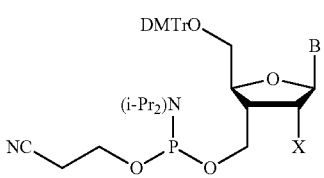

(VIII)

wherein:
B is a base pairing moiety;
X is selected from the group consisting of H, OH, OR, F, SH, SR, $NR^2_2$, MOE, alkyl, allyl, aryl, and $C_{1-6}$-alkoxy;
$R^1$ is alkyl, allyl or aryl; and
$R^2$ is alkyl, allyl or aryl.

In an embodiment of Formula (VIII), the base pairing moiety B is selected from the group consisting of adenine, guanine, cytosine, and uracil.

In another aspect, the disclosure provides phosphoramidite derivative of Formula (IX):

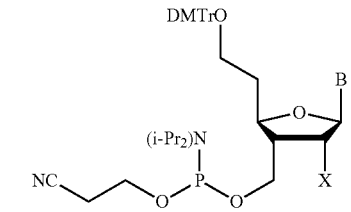

(IX)

wherein:
B is a base pairing moiety;
X is selected from the group consisting of H, OH, OR, F, SH, SR, $NR^2_2$, MOE, alkyl, allyl, aryl, and $C_{1-6}$-alkoxy;
$R^1$ is alkyl, allyl or aryl; and
$R^2$ is alkyl, allyl or aryl.

In an embodiment of Formula (IX) wherein the base pairing moiety B is selected from the group consisting of adenine, guanine, cytosine, and uracil.

In another aspect, the disclosure provides a method for synthesizing a modified oligonucleotide comprising a 5' end, a 3' end and at least one modified intersubunit linkage comprising:

(a) providing a nucleoside having a 5'-protecting group linked to a solid support;
(b) removal of the protecting group;
(c) combining the deprotected nucleoside with a phosphoramidite derivative of Formula (VII) to form a phosphite triester;

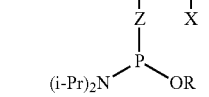

(VII)

(d) capping the phosphite triester;
(e) oxidizing the phosphite triester;
(f) repeating steps (b) through (e) using an additional phosphoramidite; and
(g) cleaving from the solid support.

In another aspect, the disclosure provides method for coupling a phosphoramidite derivative of Formula (VII):

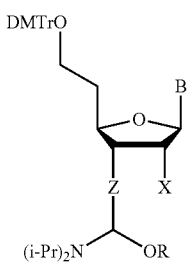

(VII)

to a 5'-terminus of a nucleoside or an oligonucleotide comprising adding the phosphoramidite derivative of Formula (VII) to the nucleoside or the oligonucleotide in an organic solvent comprising an aromatic heterocyclic acid.

In another aspect, the disclosure provides. A method for synthesizing a exNA phosphoramidite:
(a) providing a nucleoside having 3'-protecting group;
(b) oxidizing 5'-hydroxyl group of the nucleoside to a 5'-aldehyde group;
(c) converting 5'-aldehyde group of the nucleoside to a 5'-vinyl group by Wittig olefination;
(d) conducting hydroboration/oxidation on the 5'-vinyl group to produce a 6'-hydroxyl group;
(e) protecting the 6'-hydroxyl group with a DMTr group;
(f) removing the 3'-protecting group of the nucleoside;
(g) phosphitylating 3'-hydroxyl group to produce a 3'-phosphoramidite.

BRIEF DESCRIPTION OF THE DRAWINGS

The foregoing and other features and advantages of the present disclosure will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 2 provides a synthesis of a 2'-OMe-exNA phosphoramidite 9a.

FIG. 13 provides a chart of exNA-modified RNA nucleotides that have been synthesized. FIG. 13 discloses SEQ ID NOS 83 and 83-89, respectively, in order of appearance.

FIG. 20A-FIG. 20B provide results depicting in vitro silencing activity of several siRNA duplexes containing one or more antisense strand 3' end exNA intersubunit linkages. An antisense strand comprising one, two, three, or four 3' end exNA intersubunit linkages was used in a dose response curve (FIG. 20A). The percent potency change relative to an siRNA duplex control that does not contain an exNA intersubunit linkage was also determined (FIG. 20B).

FIG. 21A-FIG. 21E provide results depicting in vivo silencing activity of several siRNA duplexes containing one or more antisense strand 3' end exNA intersubunit linkages. The siRNA duplexes were in the Di-siRNA format targeting ApoE mRNA. Each siRNA duplex was administered at 5 nmol by ICV injection to mice, with ApoE mRNA levels measured 1 month later. ApoE mRNA levels were measured in the following brain regions: medial cortex (FIG. 21A), striatum (FIG. 21B), hippocampus (FIG. 21C), thalamus (FIG. 21D, and cerebellum (FIG. 21E).

FIG. 22A-FIG. 22E provide results depicting in vivo silencing activity of several siRNA duplexes containing one or more antisense strand 3' end exNA intersubunit linkages. The siRNA duplexes targeted Htt mRNA. Each siRNA duplex was administered at ~60 µg by ICV injection to mice, with Htt mRNA levels measured 2 months later. Htt mRNA levels were measured in the following brain regions: medial cortex (FIG. 22A), striatum (FIG. 22B), hippocampus (FIG. 22C), frontal cortex (FIG. 22D), and thalamus (FIG. 22E). Numbers 1-5 along the X-axis correspond to the correspond to the siRNA chemical modification patterns depicted in Example 14.

FIG. 23A-FIG. 23E provide results depicting in vivo silencing activity of several siRNA duplexes containing one or more antisense strand 3' end exNA intersubunit linkages. The siRNA duplexes targeted Htt mRNA. Each siRNA duplex was administered at ~60 µg by ICV injection to mice, with Htt protein levels measured 2 months later. Htt protein levels were measured in the following brain regions: medial cortex (FIG. 22A), striatum (FIG. 22B), hippocampus (FIG. 22C), frontal cortex (FIG. 22D), and thalamus (FIG. 22E). Numbers 1-5 along the X-axis correspond to the correspond to the siRNA chemical modification patterns depicted in Example 14.

DETAILED DESCRIPTION OF CERTAIN EXEMPLARY EMBODIMENTS

Figure 1:
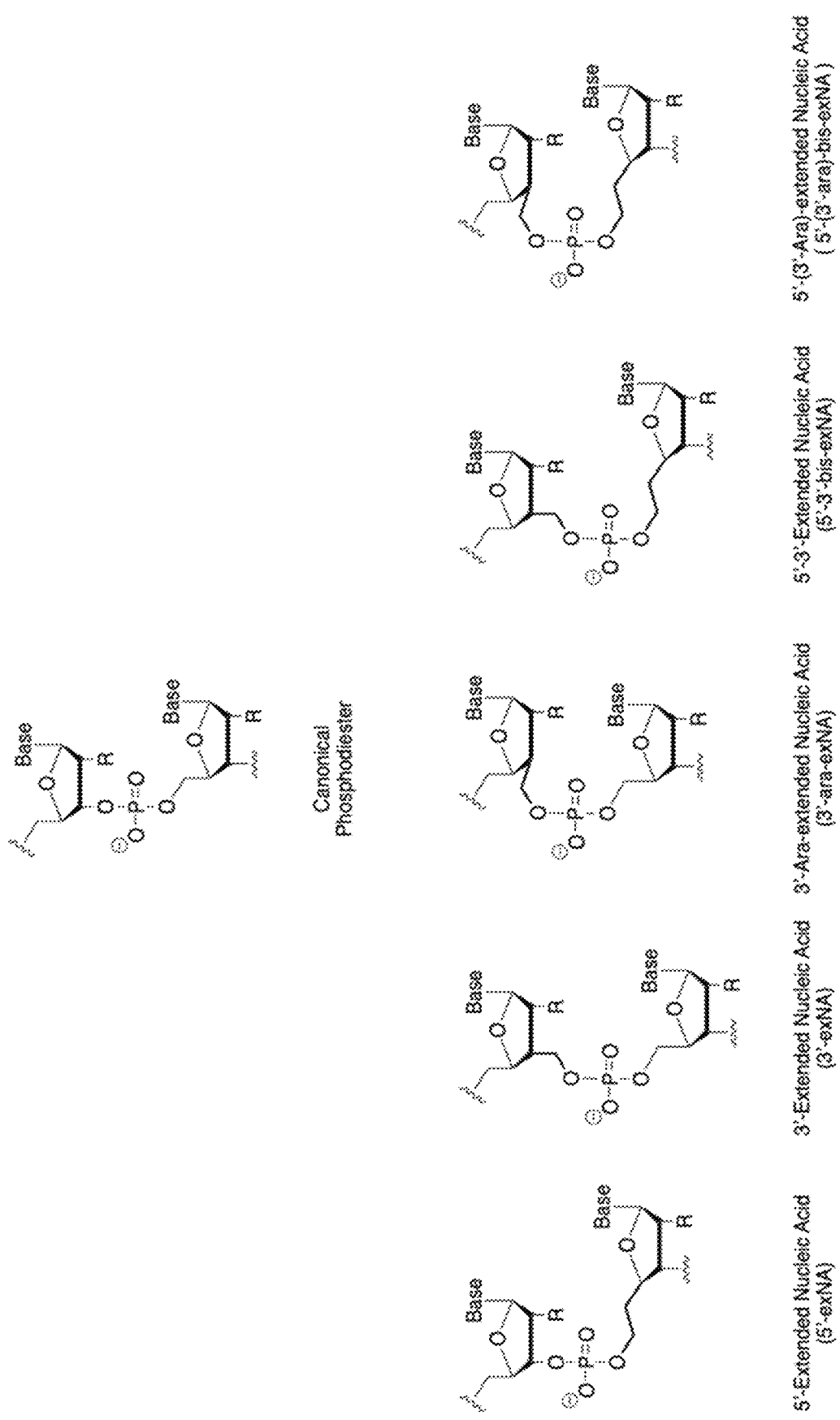
FIG. 1 summarizes the modified intersubunit linkers provided herein.

Novel modified oligonucleotides and their syntheses are provided. Also provided are novel phosphoramidites and their syntheses.

Unless otherwise specified, nomenclature used in connection with cell and tissue culture, molecular biology, immunology, microbiology, genetics and protein and nucleic acid chemistry and hybridization described herein are those well-known and commonly used in the art. Unless otherwise specified, the methods and techniques provided herein are performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the disclosure may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or "deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example, the 2' OH-group may be replaced by a group selected from H, OR, R, F, Cl, Br, I, SH, SR, $NH_2$, NHR, $NR_2$, or COOR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is an allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The phrase "examining the function of a gene in a cell or organism" refers to examining or studying the expression, activity, function or phenotype arising therefrom.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small noncoding RNAs can be generated. Exemplary RNA silencing agents include siRNAs, miRNAs, siRNA-like duplexes, antisense oligonucleotides, GAPMER molecules, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, 2N-methylguanosine and 2,2N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-µ, wherein T is an mRNA targeting moiety, L is a linking moiety, and µ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, $C_1$-$C_6$ alkoxy groups are provided herein.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "hydroxy" alone or as part of another substituent means, unless otherwise stated, an alcohol moiety having the formula —OH.

As used herein, the term "exNA" refers to an "extended nucleic acid" that contains an intersubunit linkage that contains one or more additional CH2 groups at the 3' position, at the 5' position, or both.

Preparation of linkers can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods described herein may be adjusted as necessary in light of the various substituents.

Various methodologies of the instant disclosure include step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the disclosure into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the disclosure are described in further detail in the following subsections.

I. Novel Modified Oligonucleotide Synthesis

Here we describe a portfolio of synthetic procedures for oligonucleotides modified with a novel backbone modification, Extended Nucleic Acid (exNA). This chemical modification of the backbone significantly enhances oligonucleotide metabolic stability. The chemical modification includes one or more carbon atoms or chains inserted in the backbone at the 5'-position, 3'-position, or both. This structural modulation forms non-canonical stretched/flexible structure on oligo-backbones, which protect oligonucleotides from cleavage by various nucleases.

The novel exNA-modification is widely compatible in an siRNA scaffold. The combination of an exNA-PS backbone enables drastic enhancement of metabolic stability (10-50 orders of magnitude as compared to unmodified oligos) without compromising siRNA efficacy (e.g. 5'-[exNA-PS] 4-3' modification induce NO negative impact on siRNA efficacy while inducing drastically high exonuclease stability), as will be shown below. Thus, this metabolically stabilizing exNA modification widely and robustly improves the performance of therapeutic oligonucleotide candidates in vivo.

In this disclosure, the synthesis protocol for exNA-modified oligonucleotide is described. Importantly, the exNA monomer phosphoramidite synthesis can be realized from commercially available nucleosides and the exNA-modified oligonucleotide can be made using conventional oligonucleotide solid phase synthesis procedures on an automatic oligo synthesizer.

This synthetic procedure provides following noteworthy benefits. For example, the conversion of a regular nucleoside to an "exNA-format" is applicable to many diverse modified nucleosides. Thus, this expands the possibilities to synthesize and create many more types of modified oligonucleotides with compatibility of the chemical synthesis. Secondly, there is no need of a separate specific synthesis procedure during an oligonucleotide synthesis cycle. This is a huge benefit in the ease of use of these oligos, especially with an automated synthesizer where a bottle of exNA phosphoramidite could easily be added to the machine. Thirdly, there is no need of a specific oligonucleotide deprotection condition because the exNA phosphoramidites and oligos are compatible with conventional deprotection conditions. Again, this is beneficial for the ease of synthesis and in the use of an automated synthesizer. Fourthly, it is possible to synthesize mix-mer oligonucleotide having both exNA and clinically validated modified nucleotides (e.g., 2'-OMe, 2'-F, phosphorothioate, various ligand conjugates, lipid conjugates, etc.).

In one aspect, the disclosure provides a modified oligonucleotide comprising a 5' end, a 3' end and at least one modified intersubunit linkage of Formula I:

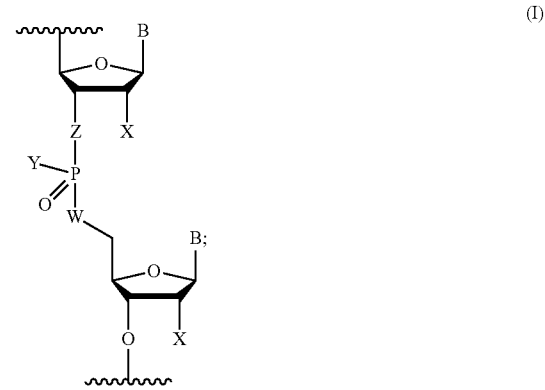

wherein:

B is a base pairing moiety;

W is O or $O(CH_2)_n$, wherein n is 1 to 10;

X is selected from the group consisting of H, OH, OR, F, SH, SR, $NR^2_2$ and $C_{1-6}$-alkoxy;

Y is selected from the group consisting of $O^-$, OH, OR, $OR^2$, $NH^-$, $NH_2$, $NR^2_2$, $BH_3$, $S^-$, $R^1$, and SH;

Z is O or $O(CH_2)_n$;

$R^1$ is alkyl, allyl or aryl; and $R^2$ is alkyl, allyl or aryl.

In an embodiment of Formula I, Z is $O(CH_2)_n$, n is 1, W is O, and Y is $O^-$.

In an embodiment of Formula I, Z is O, W is $O(CH_2)_n$, n is 1, and Y is $O^-$.

In an embodiment of Formula I, Z is $O(CH_2)_n$, n is 1, W is O, and Y is $O^-$.

In an embodiment of Formula I, Z is $O(CH_2)_n$, n is 1, W is $O(CH_2)_n$, and Y is $O^-$.

In an embodiment of Formula I, Z is $O(CH_2)_n$, n is not 1, W is $O(CH_2)_n$, and Y is $O^-$.

In an embodiment of Formula I, the base pairing moiety B is selected from the group consisting of adenine, guanine, cytosine, and uracil.

In another aspect, the disclosure provides a modified oligonucleotide comprising a 5' end, a 3' end and at least one modified intersubunit linkage of Formula II:

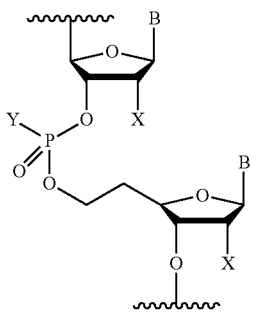

(II)

wherein:
B is a base pairing moiety;
X is selected from the group consisting of H, OH, OR, F, SH, SR, $NR^2_2$ and $C_{1-6}$-alkoxy;
Y is selected from the group consisting of $O^-$, OH, OR, $OR^2$, $NH^-$, $NH_2$, $NR^2_2$, $BH_3$, $S^-$, $R^1$, and SH;
$R^1$ is alkyl, allyl or aryl; and
$R^2$ is alkyl, allyl or aryl.

In an embodiment of Formula II, Y is O.

In an embodiment of Formula II, the base pairing moiety B is selected from the group consisting of adenine, guanine, cytosine, and uracil.

In another aspect, the disclosure provides modified oligonucleotide comprising a 5' end, a 3' end and at least one modified intersubunit linkage of Formula III:

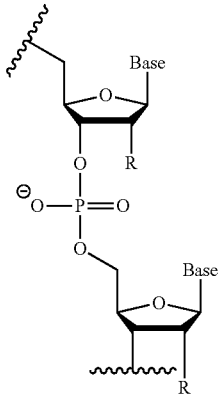

(III)

wherein:
B is a base pairing moiety;
R is alkyl, allyl or aryl.

In an embodiment of Formula III, Y is O.

In an embodiment of Formula III, the base pairing moiety B is selected from the group consisting of adenine, guanine, cytosine, and uracil.

In another aspect, the disclosure provides a modified oligonucleotide comprising a 5' end, a 3' end and at least one modified intersubunit linkage of Formula IV:

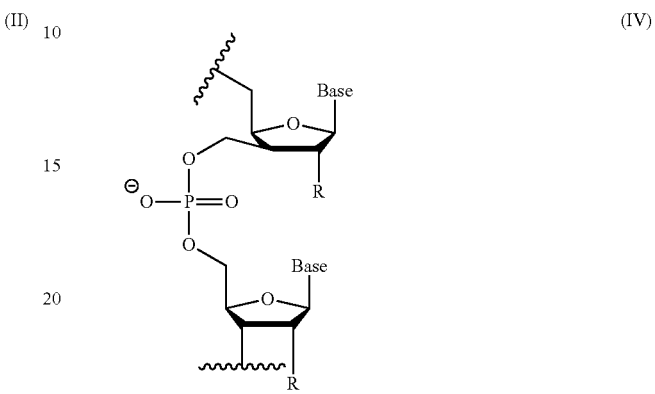

(IV)

wherein:
B is a base pairing moiety;
R is alkyl, allyl or aryl.

In an embodiment of Formula IV, the base pairing moiety B is selected from the group consisting of adenine, guanine, cytosine, and uracil.

In another aspect, the disclosure provides modified oligonucleotide comprising a 5' end, a 3' end and at least one modified intersubunit linkage of Formula V:

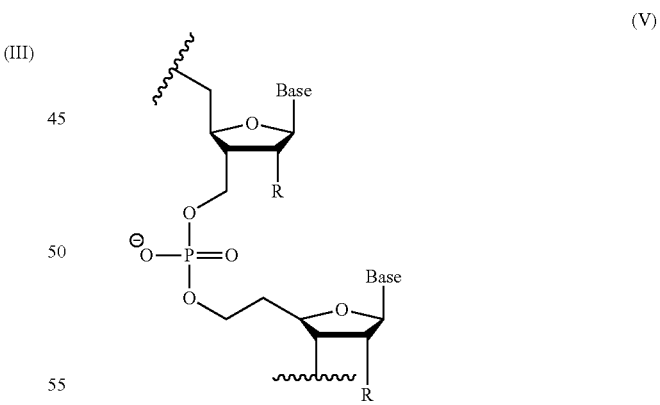

(V)

wherein:
B is a base pairing moiety;
R is alkyl, allyl or aryl.

In an embodiment of Formula V, the base pairing moiety B is selected from the group consisting of adenine, guanine, cytosine, and uracil.

In another aspect, the disclosure provides modified oligonucleotide comprising a 5' end, a 3' end and at least one modified intersubunit linkage of Formula VI:

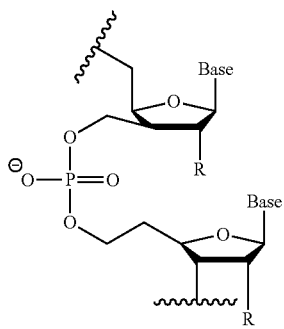

wherein:

B is a base pairing moiety;

R is alkyl, allyl or aryl.

In an embodiment of Formula VI, the base pairing moiety B is selected from the group consisting of adenine, guanine, cytosine, and uracil.

In another aspect, the disclosure provides a method for synthesizing a modified oligonucleotide comprising a 5' end, a 3' end and at least one modified intersubunit linkage comprising:

(a) providing a nucleoside having a 5'-protecting group linked to a solid support;

(b) removal of the protecting group;

(c) combining the deprotected nucleoside with a phosphoramidite derivative of Formula (VII) to form a phosphite triester;

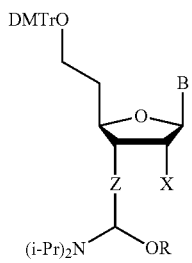

(d) capping the phosphite triester;

(e) oxidizing the phosphite triester;

(f) repeating steps (b) through (e) using an additional phosphoramidite; and (g) cleaving from the solid support.

II. Novel Phosphoramidite Derivative Synthesis

Figure 11:
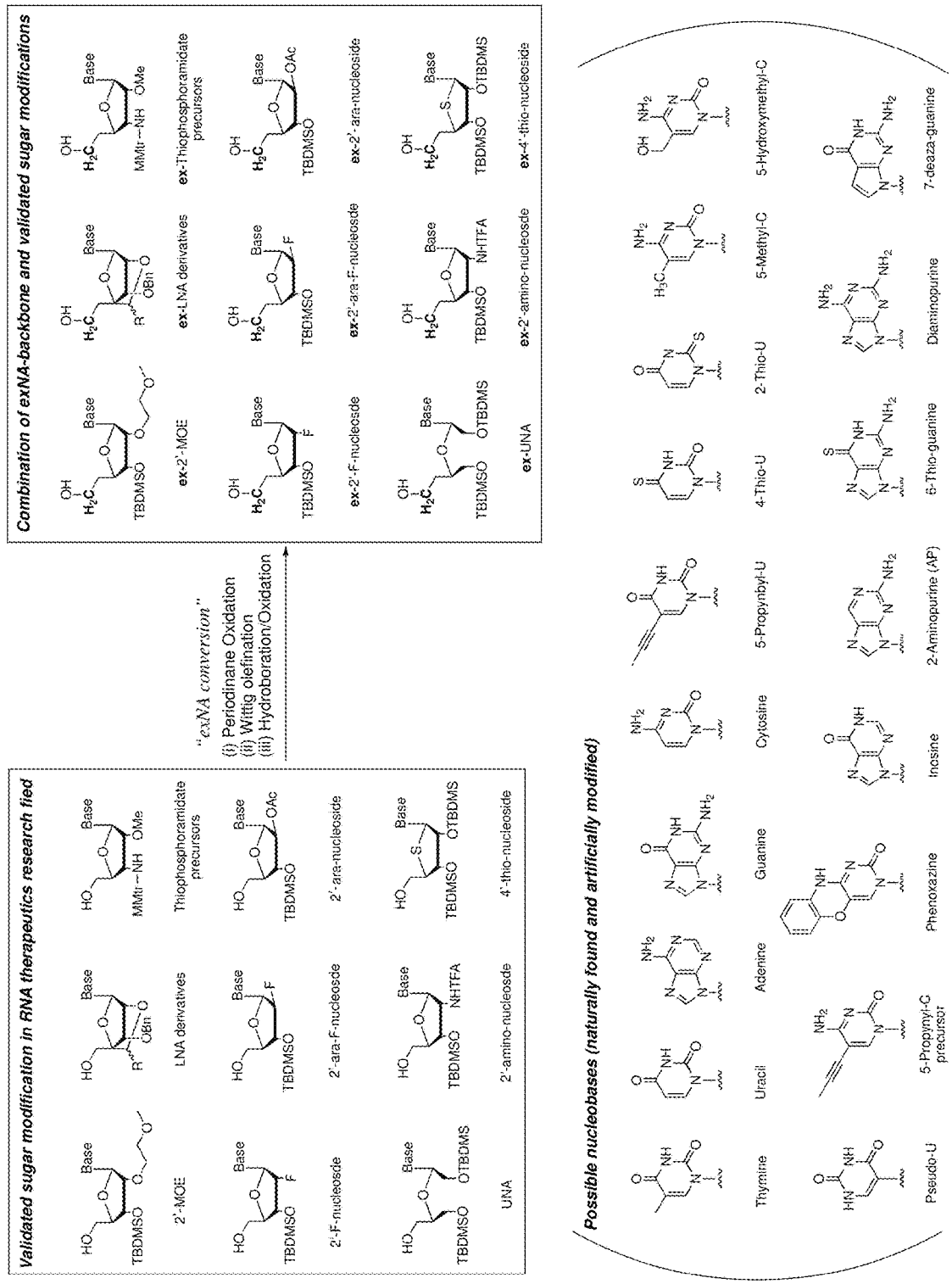
FIG. 11 provides a universal scheme for exNA conversion of sugar-modified nucleotides.

Here we describe a collection of synthetic procedures for novel phosphoramidite derivatives used to make oligonucleotides modified with the novel backbone modification, Extended Nucleic Acid (exNA). As shown in FIG. 11, this modification is very versatile and can be combined with many existing nucleosides to greatly enhance the diversity of oligonucleotides having an enhanced stability. In this aspect, the disclosure provides a phosphoramidite derivative of Formula (VII):

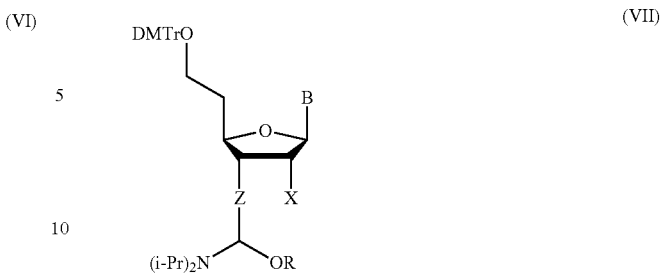

wherein:

B is a base pairing moiety;

X is selected from the group consisting of H, OH, OR, F, SH, SR, $NR^2_2$, MOE, alkyl, allyl, aryl, and $C_{1-6}$-alkoxy;

Z is O or $OCH_2$:

R is OMe or OCE (cyanoethyl):

$R^1$ is alkyl, allyl or aryl; and $R^2$ is alkyl, allyl or aryl.

In an embodiment of Formula VII, the base pairing moiety B is selected from the group consisting of adenine, guanine, cytosine, and uracil.

In another aspect, the disclosure provides a phosphoramidite derivative of Formula (VIII):

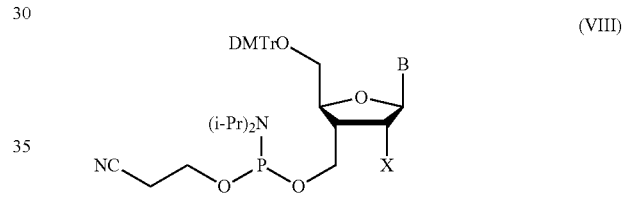

wherein:

B is a base pairing moiety;

X is selected from the group consisting of H, OH, OR, F, SH, SR, $NR^2_2$, MOE, alkyl, allyl, aryl, and $C_{1-6}$-alkoxy;

$R^1$ is alkyl, allyl or aryl; and $R^2$ is alkyl, allyl or aryl.

In an embodiment of Formula (VIII), the base pairing moiety B is selected from the group consisting of adenine, guanine, cytosine, and uracil.

In another aspect, the disclosure provides phosphoramidite derivative of Formula (IX):

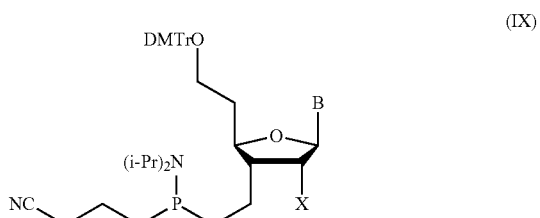

wherein:

B is a base pairing moiety;

X is selected from the group consisting of H, OH, OR, F, SH, SR, $NR^2_2$, MOE, alkyl, allyl, aryl, and $C_{1-6}$-alkoxy;

R[1] is alkyl, allyl or aryl; and
R[2] is alkyl, allyl or aryl.

In an embodiment of Formula (IX) wherein the base pairing moiety B is selected from the group consisting of adenine, guanine, cytosine, and uracil.

In another aspect, the disclosure provides method for coupling a phosphoramidite derivative of Formula (VII):

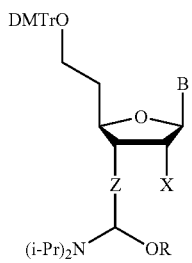

(VII)

to a 5'-terminus of a nucleoside or an oligonucleotide comprising adding the phosphoramidite derivative of Formula (VII) to the nucleoside or the oligonucleotide in an organic solvent comprising an aromatic heterocyclic acid.

In another aspect, the disclosure provides a method for synthesizing a exNA phosphoramidite including:
(a) providing a nucleoside having 3'-protecting group:
(b) oxidizing 5'-hydroxyl group of the nucleoside to a 5'-aldehyde group;
(c) converting 5'-aldehyde group of the nucleoside to a 5'-vinyl group by Wittig olefination;
(d) conducting hydroboration/oxidation on the 5'-vinyl group to produce a 6'-hydroxyl group;
(e) protecting the 6'-hydroxyl group with a DMTr group;
(f) removing the 3'-protecting group of the nucleoside;
(g) phosphitylating 3'-hydroxyl group to produce a 3'-phosphoramidite.

III. siRNA Design

In some embodiments, siRNAs are designed as follows. First, a portion of the target gene is identified. Cleavage of mRNA at these sites should eliminate translation of corresponding protein. Sense strands were designed based on the target sequence. In certain embodiments, the portion (and corresponding sense strand) includes about 15 to 25 nucleotides, e.g., 15, 16, 17, 18, 19, 20, 21, 22, 23, 24 or 25 nucleotides. The skilled artisan will appreciate, however, that siRNAs having a length of less than 15 nucleotides or greater than 25 nucleotides can also function to mediate RNAi. Accordingly, siRNAs of such length are also within the scope of the instant disclosure provided that they retain the ability to mediate RNAi. Longer RNAi agents have been demonstrated to elicit an interferon or PKR response in certain mammalian cells which may be undesirable. In one aspect, the RNAi agents of the disclosure do not elicit a PKR response (i.e., are of a sufficiently short length). However, longer RNAi agents may be useful, for example, in cell types incapable of generating a PKR response or in situations where the PKR response has been down-regulated or dampened by alternative means.

The sense strand sequence is designed such that the target sequence is essentially in the middle of the strand. Moving the target sequence to an off-center position may, in some instances, reduce efficiency of cleavage by the siRNA. However, such compositions, i.e., less efficient compositions, may be desirable for use if off-silencing of the wild-type mRNA is detected.

The antisense strand is routinely the same length as the sense strand and includes complementary nucleotides. In one embodiment, the strands are fully complementary, i.e., the strands are blunt-ended when aligned or annealed. In another embodiment, the strands comprise align or anneal such that 1-, 2-, 3-, 4-, 5-, 6- or 7-nucleotide overhangs are generated, i.e., the 3' end of the sense strand extends 1, 2, 3, 4, 5, 6 or 7 nucleotides further than the 5' end of the antisense strand and/or the 3' end of the antisense strand extends 1, 2, 3, 4, 5, 6 or 7 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment, the base-pair strength is less due to fewer G:C base pairs between the 5' end of the first or antisense strand and the 3' end of the second or sense strand than that between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the target sequences of interest is described in detail below. siRNAs can be designed according to the above exemplary teachings for any other target sequences found in the target gene. Moreover, the technology is applicable to targeting any other target sequences, e.g., non-disease-causing target sequences.

To validate the effectiveness by which siRNAs destroy mRNAs (e.g., mRNA expressed from a target gene of interest), the siRNA can be incubated with cDNA (e.g., cDNA corresponding to a target gene of interest) in a *Drosophila*-based in vitro mRNA expression system. Radiolabeled with $^{32}$P, newly synthesized mRNAs (e.g., target mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence. Sites of siRNA-mRNA complementation are selected which result in optimal mRNA specificity and maximal mRNA cleavage.

IV. RNAi Agents

The present disclosure includes siRNA molecules designed, for example, as described above. The siRNA molecules of the disclosure can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present disclosure can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/BseRI-BamHI_Strategy.pdf and katandin.cshl.org:9331/RNAi/docs/Web_version_of_PCR_strategy1.pdf).

Expression constructs of the present disclosure include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes and to facilitate delivery under certain circumstances, one or more siRNA can be expressed within cells from recombinant DNA constructs. Such methods for expressing siRNA duplexes within cells from recombinant DNA constructs permit longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002, supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when co-transfected into the cells with a vector expressing T7 RNA polymerase (Jacque et al., 2002, supra). A single construct may contain multiple sequences coding for siRNAs, such as multiple regions of the target gene, targeting the same gene or multiple genes, and can be driven, for example, by separate PolIII promoter sites.

Animal cells express a range of noncoding RNAs of approximately 22 nucleotides termed micro RNA (miR-NAs), which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the disclosure include both unmodified siRNAs and modified siRNAs as known in the art, such as crosslinked siRNA derivatives or derivatives having non-nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the disclosure can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present disclosure can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^3$H, $^{32}$P, or another appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

V. RNA Silencing Agents

In one embodiment, the present disclosure provides novel RNA silencing agents (e.g., siRNA and shRNAs), methods of making said RNA silencing agents, and methods (e.g., research and/or therapeutic methods) for using said improved RNA silencing agents (or portions thereof) for RNA silencing of a target gene. The RNA silencing agents comprise an antisense strand (or portions thereof), wherein the antisense strand has sufficient complementary to a heterozygous single nucleotide polymorphism to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-16 base pair duplexes; and (4) single-stranded, partially or fully phosphorothioated tails of 5-8 bases. The number of phosphorothioate modifications is varied from 6 to 17 total in different embodiments. In certain embodiments, the siRNA comprises 8 total phosphorothioate modifications and at least one exNA internucleotide linkage. In certain embodiments, the siRNA comprises an antisense strand with 4 total phosphorothioate modifications and at least one exNA internucleotide linkage.

In certain embodiments, the siRNA compounds described herein can be conjugated to a variety of targeting agents, including, but not limited to, cholesterol, DHA, phenyltropanes, cortisol, vitamin A, vitamin D, GalNac, and gangliozides. The cholesterol-modified version showed 5-10 fold improvement in efficacy in vitro versus previously used chemical stabilization patterns (e.g., wherein all purine but not pyrimidines are modified) in wide range of cell types (e.g., HeLa, neurons, hepatocytes, trophoblasts).

Certain compounds of the disclosure having the structural properties described herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

In the liver, hsiRNA-ASP is delivered specifically to endothelial and kupper cells, but not hepatocytes, making this chemical modification pattern complimentary rather than competitive technology to GalNac conjugates.

The compounds of the disclosure can be described in the following aspects and embodiments.

In a first aspect, provided herein is an oligonucleotide of at least 16 contiguous nucleotides, said oligonucleotide having a 5' end, a 3' end and complementarity to a target, wherein: (1) the oligonucleotide comprises alternating 2'-methoxy-ribonucleotides and 2'-fluoro-ribonucleotides; (2) the nucleotides at positions 2 and 14 from the 5' end are not 2'-methoxy-ribonucleotides; and (3) the nucleotides are connected via modified linkages as shown in FIG. 1.

a) Design of siRNA Molecules

An siRNA molecule of the disclosure is a duplex consisting of a sense strand and complementary antisense strand. In one embodiment, the siRNA molecule has a length from about 10-50 or more nucleotides, i.e., each strand comprises 10-50 nucleotides (or nucleotide analogs). In another embodiment, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In one aspect, the strands are aligned such that there are at least 1, 2, or 3 bases at the end of the strands, which do not align (i.e., for which no complementary bases occur in the opposing strand), such that an overhang of 1, 2 or 3 residues occurs at one or both ends of the duplex when the strands are annealed. In another aspect, the siRNA molecule has a length from about 10-50 or more nucleotides, i.e., each strand comprises 10-50 nucleotides (or nucleotide analogs). In yet another aspect, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Usually, siRNAs can be designed by using any method known in the art, for instance, by using the following protocol:

2. The sense strand of the siRNA is designed based on the sequence of the selected target site. In one embodiment, the sense strand includes about 19 to 25 nucleotides, e.g., 19, 20, 21, 22, 23, 24 or 25 nucleotides. In another embodiment, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant disclosure, provided that they retain the ability to mediate RNAi. Longer RNA silencing agents have been demonstrated to elicit an interferon or Protein Kinase R (PKR) response in certain mammalian cells which may be undesirable. In one aspect, the RNA silencing agents of the disclosure do not elicit a PKR response (i.e., are of a sufficiently short length). However, longer RNA silencing agents may be useful, for example, in cell types incapable of generating a PKR response or in situations where the PKR response has been down-regulated or dampened by alternative means.

The siRNA molecules described herein have sufficient complementarity with the target sequence such that the siRNA can mediate RNAi. In general, siRNA containing nucleotide sequences are sufficiently identical to a target sequence portion of the target gene to effect RISC-mediated cleavage of the target gene. Accordingly, in one embodiment, the sense strand of the siRNA is designed to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is utilized in one embodiment. The disclosure herein has the advantage of being able to tolerate certain sequence variations to enhance efficiency and specificity of RNAi. In one embodiment, the sense strand has 4, 3, 2, 1, or 0 mismatched nucleotide(s) with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). One non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). One non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus, in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, the potential targets can be compared to the appropriate genome database (human, mouse, rat, etc.) and any target sequences with significant homology to other coding sequences can be eliminated. One such method for such sequence homology searches is known as BLAST, which is available at National Center for Biotechnology Information website.

5. Select one or more sequences that meet criteria for evaluation.

Further general information about the design and use of siRNA may be found in "The siRNA User Guide," available at The Max-Plank-Institut fur Biophysikalische Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na$^+$] is the concentration of sodium ions in the hybridization buffer ([Na$^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant mRNA), the siRNA may be incubated with target cDNA in a *Drosophila*-based in vitro mRNA expression system. Radiolabeled with $^{32}$P, newly synthesized target mRNAs are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

In certain embodiments, the siRNA comprises a sense strand comprising a linkage set forth at FIG. 1, or an antisense strand comprising a linkage set forth at FIG. 1.

Sites of siRNA-mRNA complementation are selected, which result in optimal mRNA specificity and maximal mRNA cleavage.

b) siRNA-Like Molecules siRNA-like molecules of the disclosure have a sequence (i.e., have a strand having a sequence) that is "sufficiently complementary" to a target sequence of an mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further embodiment, the "bulge" is centered at nucleotide positions 12 and 13 from the 5' end of the miRNA molecule.

c) Short Hairpin RNA (shRNA) Molecules

In certain featured embodiments, the instant disclosure provides shRNAs capable of mediating RNA silencing of a target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides, which can regulate gene expression at the post transcriptional or translational level during plant and animal development. One common feature of miRNAs is that they are excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the disclosure are artificial constructs based on these naturally occurring pre-miRNAs, but which are engineered to deliver desired RNA silencing agents (e.g., siRNAs of the disclosure). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant disclosure, one portion of the duplex stem is a nucleic acid sequence that is complementary (or anti-sense) to the target sequence. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the disclosure include the sequences of a desired siRNA molecule described supra. In other embodiments, the sequence of the antisense portion of a shRNA can be designed essentially as described above or generally by selecting an 18, 19, 20, 21 nucleotides, or longer, sequence from within the target RNA, for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the disclosure include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans,* zebrafish, *Arabidopsis thalania, Mus musculus,* and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with an miRNA disorder.

d) Dual Functional Oligonucleotide Tethers

In other embodiments, the RNA silencing agents of the present disclosure include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offers several advantages over existing techniques to repress the expression of a particular gene. First, the methods described herein allow an endogenous molecule (often present in abundance), an miRNA, to mediate RNA silencing. Accordingly, the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present disclosure can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the disclosure are designed such that they recruit miRNAs (e.g., endogenous cellular miRNAs) to a target mRNA so as to induce the modulation of a gene of interest. In preferred embodiments, the tethers have the formula T-L-µ, wherein T is an mRNA targeting moiety, L is a linking moiety, and µ is an miRNA recruiting moiety. Any one or more moiety may be double stranded. Preferably, however, each moiety is single stranded.

Moieties within the tethers can be arranged or linked (in the 5' to 3' direction) as depicted in the formula (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: µ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the disclosure, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the disclosure, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (e.g., target gene expression) can be modulated using oligonucleotide-based compounds comprising two or more single stranded antisense oligonucleotides that are linked through their 5'-ends that allow the presence of two or more accessible 3'-ends to effectively inhibit or decrease target gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.) Provided herein are novel and improved GSOs comprising intersubunit linkages according to Formula (I) and its embodiments.

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the disclosure, therefore, comprise two or more oligonucleotides linked to a nucleotide or a non-nucleotide linker. Such oligonucleotides according to the disclosure are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidate or H-phosphonate chemistry which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

VI. Modified RNA Silencing Agents

In certain aspects of the disclosure, the oligonucleotides, siRNA, and RNA silencing agents (or any portion thereof) of the disclosure as described supra may be modified such that the activity of the agent is further improved. For example, the RNA silencing agents described in Section II supra may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the oligonucleotides, siRNA, and RNA silencing agents of the disclosure may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the disclosure are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotides include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the disclosure are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide.

In preferred embodiments, the destabilizing nucleotide is introduced in the same strand or strand portion that contains the specificity-determining nucleotide.

2) Modifications to Enhance Efficacy and Specificity

In certain embodiments, the oligonucleotides, siRNA, and RNA silencing agents of the disclosure may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the disclosure or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S '5) of said RNA silencing agent.

In one embodiment, the asymmetry of an RNA silencing agent of the disclosure may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the disclosure may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the disclosure may be enhanced such that there is at least one wobble base pair, e.g., G:U, between the 5' end of the first or antisense strand and the 3' end of the sense strand portion. In another embodiment, the asymmetry of an RNA silencing agent of the disclosure may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the disclosure may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present disclosure can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a one aspect, the disclosure features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In one aspect, the disclosure features RNA silencing agents that are at least 80% chemically modified. In a preferred embodiment of the present disclosure, the RNA silencing agents may be fully chemically modified, i.e., 100% of the nucleotides are chemically modified.

In a preferred embodiment of the present disclosure, the RNA silencing agents may contain at least one modified nucleotide analogue. The nucleotide analogues may be located at positions where the target-specific silencing activity, e.g., the RNAi mediating activity or translational repression activity is not substantially affected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing moieties of the instant disclosure. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the disclosure comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the disclosure comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the disclosure includes RNA silencing agents having two complementary strands of nucleic acid, wherein the two strands are crosslinked. The disclosure also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a O with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a O with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the disclosure includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of disclosure is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl) cholenic acid, dimethoxytrityl, or phenoxazine.

5) Tethered Ligands

Other entities can be tethered to an RNA silencing agent of the disclosure. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., 0-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycosides, artificial endonucleases (e.g. EDTA), lipophilic molecules, e.g., cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octadecyl) glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu$^{3+}$ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to anon-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low-density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide. In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., Nature 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

6) Branched Oligonucleotides

Two or more oligonucleotides, where at least one of the oligonucleotides includes an intersubunit linkage according to an embodiment of Formula (I), may be connected to one another by one or more moieties independently selected from a linker, a spacer and a branching point, to form a branched compound. For example, the branched compound may contain two or more RNA silencing agents of the types set out above, resulting in a new type of RNA silencing agent having a branched structure. In representative embodiments, the oligonucleotides each comprise an antisense strand (or portions thereof), wherein the antisense strand has sufficient complementary to a heterozygous single nucleotide polymorphism to mediate an RNA-mediated silencing mechanism (e.g. RNAi).

In exemplary embodiments, the branched compounds may have two to eight RNA silencing agents attached through a linker. The linker may be hydrophobic. In a typical embodiment, branched oligonucleotides of the present application have two to three oligonucleotides. In an embodiment, the oligonucleotides independently have substantial chemical stabilization (e.g., at least 40% of the constituent bases are chemically-modified). In a particular embodiment, the oligonucleotides have full chemical stabilization (i.e., all the constituent bases are chemically-modified). In some embodiments, branched oligonucleotides comprise one or more single-stranded phosphorothioated tails, each tail independently having two to twenty nucleotides. In a non-limiting embodiment, each single-stranded tail has eight to ten nucleotides.

In certain embodiments, branched compounds are characterized by three properties: (1) a branched structure, (2) full metabolic stabilization, and (3) the presence of a single-stranded tail comprising phosphorothioate linkers. In an exemplary embodiment, branched oligonucleotides have 2 or 3 branches. The increased overall size of the branched structures promotes increased uptake. Also, without being bound by a particular theory of activity, it appears that multiple adjacent branches (e.g., 2 or 3) allow each branch to act cooperatively and thus dramatically enhance rates of internalization, trafficking and release.

Branched compounds are provided in various structurally diverse embodiments. In some embodiments nucleic acids attached at the branching points are single stranded and include miRNA inhibitors, gapmers, mixmers, SSOs, PMOs, or PNAs. These single strands can be attached at their 3' or 5' end. Combinations of siRNA and single stranded oligonucleotides could also be used for dual function. In another embodiment, short nucleic acids complementary to the gapmers, mixmers, miRNA inhibitors, SSOs, PMOs, and PNAs are used to carry these active single-stranded nucleic acids and enhance distribution and cellular internalization. The short duplex region has a low melting temperature ($T_m$~37° C.) for fast dissociation upon internalization of the branched structure into the cell.

"Di-siRNA" compounds, that is, branched oligonucleotides having two siRNAs and a linker, may comprise chemically diverse conjugates. Conjugated bioactive ligands may be used to enhance cellular specificity and to promote membrane association, internalization, and serum protein binding. Examples of bioactive moieties to be used for conjugation include DHAg2, DHA, GalNAc, and cholesterol. These moieties can be attached to Di-siRNA either through the connecting linker or spacer, or added via an additional linker or spacer attached to another free siRNA end.

Without being bound to any particular theory, it has been found that the presence of a branched structure improves the level of tissue retention in the brain more than 100-fold compared to non-branched compounds of identical chemical composition, suggesting a new mechanism of cellular retention and distribution. Branched oligonucleotides have unexpectedly uniform distribution throughout the spinal cord and brain. Moreover, branched oligonucleotides exhibit unexpectedly efficient systemic delivery to a variety of tissues, and very high levels of tissue accumulation.

Branched oligonucleotides may comprise a variety of therapeutic nucleic acids, including ASOs, miRNAs, miRNA inhibitors, splice switching, PMOs, PNAs. In some embodiments, branched oligonucleotides further comprise conjugated hydrophobic moieties and exhibit unprecedented silencing and efficacy in vitro and in vivo.

Linkers

In an embodiment of the branched oligonucleotide compounds, each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment, each linker is an ethylene glycol chain. In another embodiment, each linker is an alkyl chain. In another embodiment, each linker is a peptide. In another embodiment, each linker is RNA. In another embodiment, each linker is DNA. In another embodiment, each linker is a phosphate. In another embodiment, each linker is a phosphonate. In another embodiment, each linker is a phosphoramidate. In another embodiment, each linker is an ester. In another embodiment, each linker is an amide. In another embodiment, each linker is a triazole.

VI.

In another aspect, provided herein is a branched oligonucleotide compound of formula (1):

$$L\text{-}(N)_n \quad (1)$$

wherein L is selected from an ethylene glycol chain, an alkyl chain, a peptide, RNA, DNA, a phosphate, a phosphonate, a phosphoramidate, an ester, an amide, a triazole, and combinations thereof, wherein Formula (1) optionally further comprises one or more branch point Bp, and one or more spacer S; wherein Bp is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; N is an RNA duplex comprising a sense strand and an antisense strand, wherein the sense strand and antisense strand each independently comprise one or more chemical modifications; and n is 2, 3, 4, 5, 6, 7 or 8. In an embodiment, at least one N includes a modified intersubunit linkage of Formula (I).

In an embodiment, the compound of Formula (1) has a structure selected from formulas (1-1)-(1-9) of Table 1.

TABLE 1

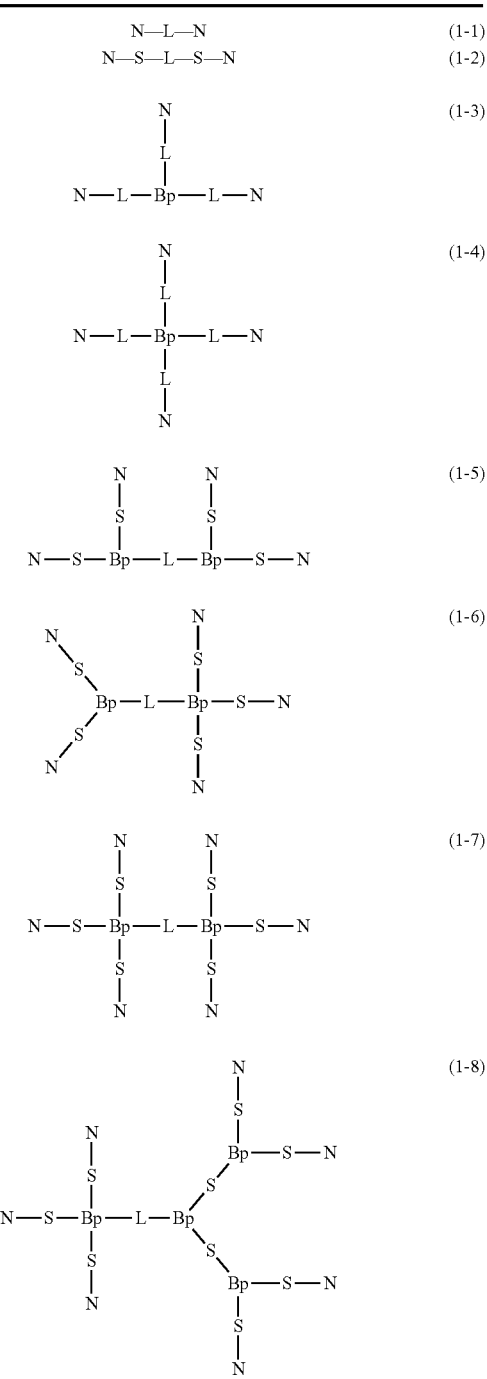

TABLE 1-continued

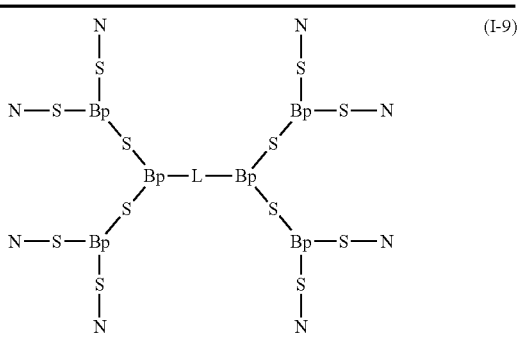

(I-9)

In one embodiment, the compound of Formula (1) is formula (1-1). In another embodiment, the compound of Formula (1) is Formula (1-2). In another embodiment, the compound of Formula (1) is Formula (1-3). In another embodiment, the compound of formula (1) is Formula (1-4). In another embodiment, the compound of Formula (1) is formula (1-5). In another embodiment, the compound of Formula (1) is Formula (1-6). In another embodiment, the compound of Formula (1) is Formula (1-7). In another embodiment, the compound of Formula (1) is Formula (1-8). In another embodiment, the compound of formula (1) is formula (1-9).

In an embodiment of the compound of Formula (1), each linker is independently selected from an ethylene glycol chain, an alkyl chain, a peptide, RNA, DNA, a phosphate, a phosphonate, a phosphoramidate, an ester, an amide, a triazole, and combinations thereof; wherein any carbon or oxygen atom of the linker is optionally replaced with a nitrogen atom, bears a hydroxyl substituent, or bears an oxo substituent. In one embodiment of the compound of Formula (1), each linker is an ethylene glycol chain. In another embodiment, each linker is an alkyl chain. In another embodiment of the compound of Formula (1), each linker is a peptide. In another embodiment of the compound of Formula (1), each linker is RNA. In another embodiment of the compound of Formula (1), each linker is DNA. In another embodiment of the compound of Formula (1), each linker is a phosphate. In another embodiment, each linker is a phosphonate. In another embodiment of the compound of Formula (1), each linker is a phosphoramidate. In another embodiment of the compound of Formula (1), each linker is an ester. In another embodiment of the compound of Formula (1), each linker is an amide. In another embodiment of the compound of Formula (1), each linker is a triazole.

In one embodiment of the compound of Formula (1), Bp is a polyvalent organic species. In another embodiment of the compound of Formula (1), Bp is a derivative of a polyvalent organic species. In one embodiment of the compound of Formula (1), Bp is a triol or tetrol derivative. In another embodiment, Bp is a tri- or tetra-carboxylic acid derivative. In another embodiment, Bp is an amine derivative. In another embodiment, Bp is a tri- or tetra-amine derivative. In another embodiment, Bp is an amino acid derivative.

Polyvalent organic species are moieties comprising carbon and three or more valencies (i.e., points of attachment with moieties such as S, L or N, as defined above). Non-limiting examples of polyvalent organic species include triols (e.g., glycerol, phloroglucinol, and the like), tetrols (e.g., ribose, pentaerythritol, 1,2,3,5-tetrahydroxybenzene, and the like), tri-carboxylic acids (e.g., citric acid, 1,3,5-cyclohexanetricarboxylic acid, trimesic acid, and the like), tetra-carboxylic acids (e.g., ethylenediaminetetraacetic acid, pyromellitic acid, and the like), tertiary amines (e.g., tripropargylamine, triethanolamine, and the like), triamines (e.g., diethylenetriamine and the like), tetramines, and species comprising a combination of hydroxyl, thiol, amino, and/or carboxyl moieties (e.g., amino acids such as lysine, serine, cysteine, and the like).

In an embodiment of the compound of Formula (1), each nucleic acid comprises one or more chemically-modified nucleotides. In an embodiment of the compound of Formula (1), each nucleic acid consists of chemically-modified nucleotides. In certain embodiments of the compound of Formula (1), >95%, >90%, >85%, >80%, >75%, >70%, >65%, >60%, >55% or >50% of each nucleic acid comprises chemically-modified nucleotides.

In an embodiment, each antisense strand independently comprises a 5' terminal group R selected from the groups of Table 2.

TABLE 2

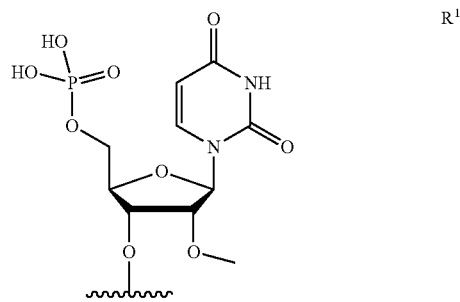

$R^1$

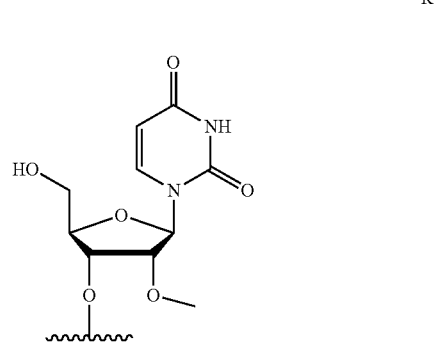

$R^2$

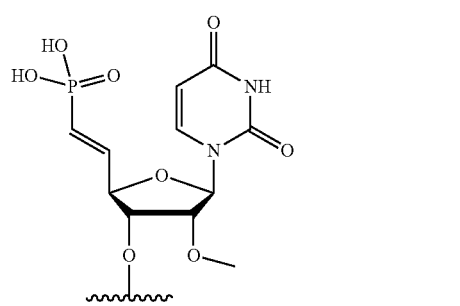

$R^3$

TABLE 2-continued

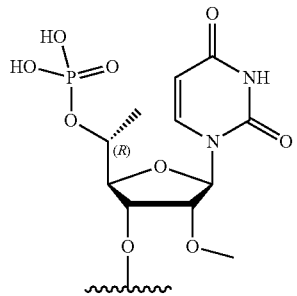
R⁴

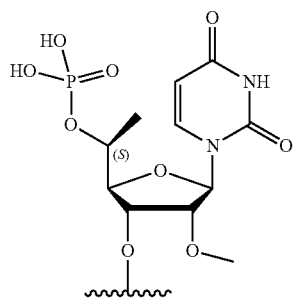
R⁵

TABLE 2-continued

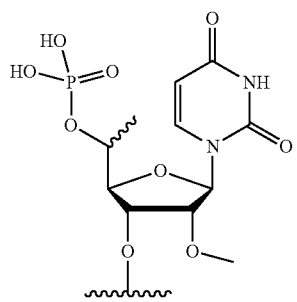
R⁶

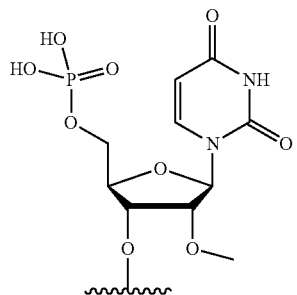
R⁷

TABLE 2-continued

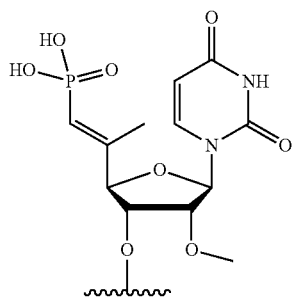
R⁸

In one embodiment, R is $R_1$. In another embodiment, R is $R_2$. In another embodiment, R is $R_3$. In another embodiment, R is $R_4$. In another embodiment, R is $R_5$. In another embodiment, R is $R_6$. In another embodiment, R is $R_7$. In another embodiment, R is $R_8$.

Structure of Formula (2)

In an embodiment, the compound of Formula (1) the structure of Formula (2):

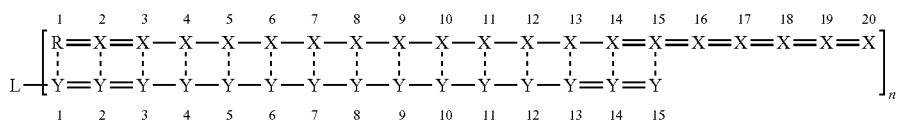

(2)

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; = represents a phosphorothioate internucleoside linkage; and - - - represents, individually for each occurrence, a base-pairing interaction or a mismatch. Moreover, at least one of the internucleoside linkages may be replaced with a modified intersubunit linkage of Formula (I).

In certain embodiments, the structure of Formula (2) does not contain mismatches. In one embodiment, the structure of Formula (2) contains 1 mismatch. In another embodiment, the compound of Formula (2) contains 2 mismatches. In another embodiment, the compound of Formula (2) contains 3 mismatches. In another embodiment, the compound of Formula (2) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of Formula (2) are chemically-modified nucleotides. In other embodiments, >95%, >90%, >85%, >80%, >75%, >70%, >65%, >60%, >55% or >50% of X's of the structure of Formula (2) are chemically-modified nucleotides.

Structure of Formula (3)

In an embodiment, the compound of Formula (1) has the structure of Formula (3):

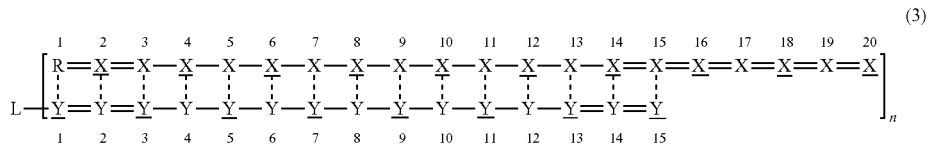

wherein X̲, for each occurrence, independently, is a nucleotide comprising a 2'-deoxy-2'-fluoro modification; X, for each occurrence, independently, is a nucleotide comprising a 2'-O-methyl modification; Y̲, for each occurrence, independently, is a nucleotide comprising a 2'-deoxy-2'-fluoro modification; and Y, for each occurrence, independently, is a nucleotide comprising a 2'-O-methyl modification.

In an embodiment, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of Formula (3) does not contain mismatches. In one embodiment, the structure of Formula (3) contains 1 mismatch. In another embodiment, the compound of Formula (3) contains 2 mismatches. In another embodiment, the compound of Formula (3) contains 3 mismatches. In another embodiment, the compound of Formula (3) contains 4 mismatches.

Structure of Formula (4)

In an embodiment, the compound of Formula (1) has the structure of Formula (4):

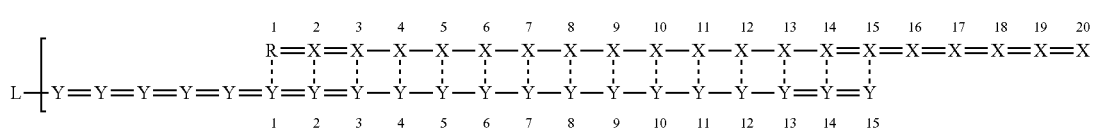

wherein X, for each occurrence, independently, is selected from adenosine, guanosine, uridine, cytidine, and chemically-modified derivatives thereof; Y, for each occurrence, independently, is selected from adenosine, guanosine, uridine, cytidine, and chemically-modified derivatives thereof; — represents a phosphodiester internucleoside linkage; ═ represents a phosphorothioate internucleoside linkage; and - - - represents, individually for each occurrence, a base-pairing interaction or a mismatch. Also, at least one of the internucleoside linkages may be replaced with a modified intersubunit linkage of Formula (I).

In certain embodiments, the structure of Formula (4) does not contain mismatches. In one embodiment, the structure of Formula (4) contains 1 mismatch. In another embodiment, the compound of Formula (4) contains 2 mismatches. In another embodiment, the compound of Formula (4) contains 3 mismatches. In another embodiment, the compound of Formula (4) contains 4 mismatches. In an embodiment, each nucleic acid consists of chemically-modified nucleotides.

In certain embodiments, >95%, >90%, >85%, >80%, >75%, >70%, >65%, >60%, >55% or >50% of X's of the structure of Formula (2) are chemically-modified nucleotides. In other embodiments, >95%, >90%, >85%, >80%, >75%, >70%, >65%, >60%, >55% or >50% of X's of the structure of Formula (2) are chemically-modified nucleotides.

Structure of Formula (5)

In some embodiments, the compound of Formula (1) has the structure of Formula (5):

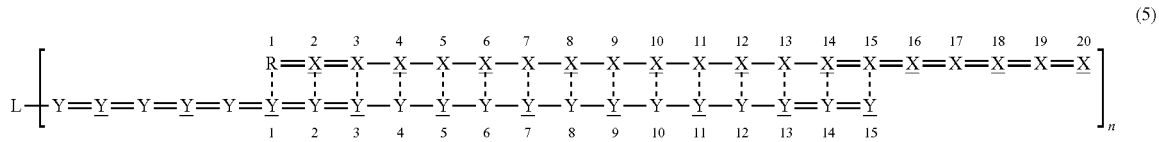

wherein X̲, for each occurrence, independently, is a nucleotide comprising a 2'-deoxy-2'-fluoro modification; X, for each occurrence, independently, is a nucleotide comprising a 2'-O-methyl modification; Y̲, for each occurrence, independently, is a nucleotide comprising a 2'-deoxy-2'-fluoro modification; and Y, for each occurrence, independently, is a nucleotide comprising a 2'-O-methyl modification.

In certain embodiments, X is chosen from the group consisting of 2'-deoxy-2'-fluoro modified adenosine, guanosine, uridine or cytidine. In an embodiment, X is chosen from the group consisting of 2'-O-methyl modified adenosine, guanosine, uridine or cytidine. In an embodiment, Y is chosen from the group consisting of 2'-deoxy-2'-fluoro modified adenosine, guanosine, uridine or cytidine. In an embodiment, Y is chosen from the group consisting of 2'-O-methyl modified adenosine, guanosine, uridine or cytidine.

In certain embodiments, the structure of Formula (5) does not contain mismatches. In one embodiment, the structure of Formula (6) contains 1 mismatch. In another embodiment, the compound of Formula (5) contains 2 mismatches. In another embodiment, the compound of Formula (5) contains 3 mismatches. In another embodiment, the compound of formula (V) contains 4 mismatches.

Variable Linkers

In an embodiment of the compound of Formula (1), L has the structure of L1:

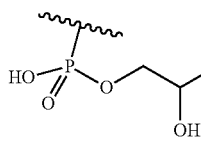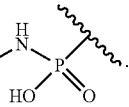

(L1)

In an embodiment of L1, R is $R^3$ and n is 2.

In an embodiment of the structure of formula (II), L has the structure of L1. In an embodiment of the structure of formula (III), L has the structure of L1. In an embodiment of the structure of formula (IV), L has the structure of L1. In an embodiment of the structure of formula (V), L has the structure of L1. In an embodiment of the structure of formula (VI), L has the structure of L1. In an embodiment of the structure of formula (VII), L has the structure of L1.

In an embodiment of the compound of Formula (1), L has the structure of L2:

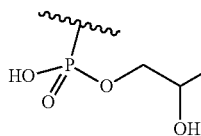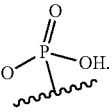

(L2)

In an embodiment of L2, R is $R^3$ and n is 2. In an embodiment of the structure of Formula (2), L has the structure of L2. In an embodiment of the structure of Formula (3), L has the structure of L2. In an embodiment of the structure of Formula (4), L has the structure of L2. In an embodiment of the structure of Formula (5), L has the structure of L2.

Delivery System

In another aspect, provided herein is a delivery system for therapeutic nucleic acids having the structure of Formula (6):

L-(cNA)$_n$   (6)

wherein L is selected from an ethylene glycol chain, an alkyl chain, a peptide, RNA, DNA, a phosphate, a phosphonate, a phosphoramidate, an ester, an amide, a triazole, and combinations thereof, wherein Formula (6) optionally further comprises one or more branch point Bp, and one or more spacer S; wherein Bp is independently for each occurrence a polyvalent organic species or derivative thereof; S is independently for each occurrence selected from an ethylene glycol chain, an alkyl chain, a peptide, RNA, DNA, a phosphate, a phosphonate, a phosphoramidate, an ester, an amide, a triazole, and combinations thereof; each cNA, independently, is a carrier nucleic acid comprising one or more chemical modifications; and n is 2, 3, 4, 5, 6, 7 or 8. In an embodiment, at least one cNA includes a modified intersubunit linkage of Formula (I).

In one embodiment of the delivery system, L is an ethylene glycol chain. In another embodiment of the delivery system, L is an alkyl chain. In another embodiment of the delivery system, L is a peptide. In another embodiment of the delivery system, L is RNA. In another embodiment of the delivery system, L is DNA. In another embodiment of the delivery system, L is a phosphate. In another embodiment of the delivery system, L is a phosphonate. In another embodiment of the delivery system, L is a phosphoramidate. In another embodiment of the delivery system, L is an ester. In another embodiment of the delivery system, L is an amide. In another embodiment of the delivery system, L is a triazole.

In one embodiment of the delivery system, S is an ethylene glycol chain. In another embodiment, S is an alkyl chain. In another embodiment of the delivery system, S is a peptide. In another embodiment, S is RNA. In another embodiment of the delivery system, S is DNA. In another embodiment of the delivery system, S is a phosphate. In another embodiment of the delivery system, S is a phosphonate. In another embodiment of the delivery system, S is a phosphoramidate. In another embodiment of the delivery system, S is an ester. In another embodiment, S is an amide. In another embodiment, S is a triazole.

In one embodiment of the delivery system, n is 2. In another embodiment of the delivery system, n is 3. In another embodiment of the delivery system, n is 4. In another embodiment of the delivery system, n is 5. In another embodiment of the delivery system, n is 6. In another embodiment of the delivery system, n is 7. In another embodiment of the delivery system, n is 8.

In certain embodiments, each cNA comprises >95%, >90%, >85%, >80%, >75%, >70%, >65%, >60%, >55% or >50% chemically-modified nucleotides.

In an embodiment, the compound of Formula (6) has a structure selected from formulas (6-1)-(6-9) of Table 3:

TABLE 3

| | |
|---|---|
| ANc—L—cNA | (6-1) |
| ANc—S—L—S—cNA | (6-2) |
| 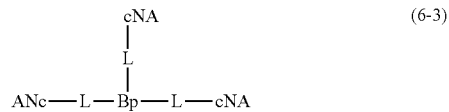 | (6-3) |

TABLE 3-continued (6-4)
```
         cNA
          |
          L
          |
ANc—L—Bp—L—cNA
          |
          L
          |
         cNA
```

(6-5)
```
         cNA        cNA
          |          |
          S          S
          |          |
ANc—S—Bp—L—Bp—S—cNA
```

(6-6)
```
                    cNA
                     |
ANc                  S
   \                 |
    S                |
     \               |
      Bp—L—Bp—S—cNA
     /               |
    S                S
   /                 |
ANc                  |
                    cNA
```

(6-7)
```
         cNA        cNA
          |          |
          S          S
          |          |
ANc—S—Bp—L—Bp—S—cNA
          |          |
          S          S
          |          |
         cNA        cNA
```

(6-8)
```
                     cNA
                      |
                      S
         cNA          |
          |          Bp—S—cNA
          S         /
          |        S
ANc—S—Bp—L—Bp
          |        S
          S         \
          |          Bp—S—cNA
         cNA          |
                      S
                      |
                     cNA
```

(6-9)
```
    ANc                        cNA
     |                          |
     S                          S
     |                          |
ANc—S—Bp                       Bp—S—cNA
        \                     /
         S                   S
          \                 /
           Bp—L—Bp
          /                 \
         S                   S
        /                     \
ANc—S—Bp                       Bp—S—cNA
     |                          |
     S                          S
     |                          |
    cNA                        cNA
```

In an embodiment, the compound of Formula (6) is the structure of formula (6-1). In an embodiment, the compound of Formula (6) is the structure of Formula (6-2). In an embodiment, the compound of Formula (6) is the structure of Formula (6-3). In an embodiment, the compound of Formula (6) is the structure of Formula (6-4). In an embodiment, the compound of Formula (6) is the structure of formula (6-5). In an embodiment, the compound of Formula (6) is the structure of formula (6-6). In an embodiment, the compound of Formula (6) is the structure of Formula (6-7). In an embodiment, the compound of Formula (6) is the structure of formula (6-8). In an embodiment, the compound of Formula (6) is the structure of formula (6-9).

In an embodiment, the compound of Formulas (6) (including, e.g., one of formulas (6-1)-(6-9), each cNA independently comprises at least 15 contiguous nucleotides. In an embodiment, each cNA independently consists of chemically-modified nucleotides.

In an embodiment, each NA is hybridized to at least one cNA. In an embodiment, at least one NA includes a modified intersubunit linkage of Formula (I). In certain embodiments, compounds of the disclosure are characterized by the following properties: (1) two or more branched oligonucleotides, e.g., wherein there is a non-equal number of 3' and 5' ends; (2) substantially chemically stabilized, e.g., wherein more than 40%, optimally 100%, of oligonucleotides are chemically modified (e.g., no RNA and optionally no DNA); and (3) phosphorothioated single oligonucleotides containing at least 3, optimally 5-20 phosphorothioated bonds.

VII. Methods of Introducing Nucleic Acids, Vectors Host Cells, and Branched Oligonucleotide Compounds RNA silencing agents of the disclosure may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the disclosure can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus, the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Depending on the assay, quantitation of the amount of gene expression allows one to determine a degree of inhibition which is greater than 10%, 33%, 50%, 90%, 95% or 99% as compared to a cell not treated according to the present disclosure. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the disclosure (e.g., an siRNA targeting a target sequence of interest) is tested for its ability to specifically degrade mutant mRNA (e.g., target mRNA and/or the production of target protein) in cells, in particular, in neurons (e.g., striatal or cortical neuronal clonal lines and/or primary neurons). Also, suitable for cell-based validation assays are other readily transfectable cells, for example, HeLa cells or COS cells. Cells are transfected with human wild type or mutant cDNAs (e.g., human wild type or mutant target cDNA). Standard siRNA, modified siRNA or vectors able to produce siRNA from U-looped mRNA are co-transfected. Selective reduction in target mRNA and/or target protein is measured. Reduction of target mRNA or protein can be compared to levels of target mRNA or protein in the absence of an RNAi agent or in the presence of an RNAi agent that does not target the target mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

Recombinant Adeno-Associated Viruses and Vectors

In certain exemplary embodiments, recombinant adeno-associated viruses (rAAVs) and their associated vectors can be used to deliver one or more siRNAs into cells, e.g., neural cells (e.g., brain cells). AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In particular embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) Mol. Ther. 19(8):1440-8. doi: 10.1038/mt.2011.98. Epub 2011 May 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., Macaque) or the like. In certain embodiments, a host animal is a non-human host animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the central nervous system (CNS) of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the disclosure may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 base pairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present disclosure is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

VIII. Methods of Treatment

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the disclosure provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the disclosure pertains to methods treating subjects therapeutically, i.e., alter onset of symptoms of the disease or disorder.

With regards to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the disclosure provides methods for tailoring an individual's prophylactic or therapeutic treatment with either the target gene molecules of the present disclosure or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent. Alternatively, an agent can be used in an animal model to determine the mechanism of action of such an agent.

A pharmaceutical composition containing an RNA silencing agent of the disclosure can be administered to any patient diagnosed as having or at risk for developing a neurodegenerative disease. In one embodiment, the patient is diagnosed as having a neurological disorder, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as motor fluctuations and dyskinesis in Parkinson's disease patients. In another embodiment, the patient has not reached an advanced stage of the disease.

An RNA silencing agent modified for enhanced uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the brain) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. The dosage can be an amount effective to treat or prevent a neurodegenerative disease or disorder, e.g., AD or ALS. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it may be desirable to have the patient undergo maintenance therapy to prevent the recurrence of the disease state, wherein the compound of the disclosure is administered in maintenance doses, ranging from 0.01 µg to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or, preferably, can include a series of treatments. It will also be appreciated that the effective dosage of an RNA silencing agent for treatment may increase or decrease over the course of a particular treatment. Changes in dosage may result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is affected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

IX. Pharmaceutical Compositions and Methods of Administration

The disclosure pertains to uses of the above-described agents for prophylactic and/or therapeutic treatments as described infra. Accordingly, the modulators (e.g., branched oligonucleotides comprising RNA silencing agents) of the present application can be incorporated into pharmaceutical compositions suitable for administration. Such compositions typically comprise the nucleic acid molecule, protein, antibody, or branched oligonucleotide compound and a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, a pharmaceutical composition of the disclosure is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like). Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous, IS, ICV and/or IT administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the disclosure, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack or dispenser together with optional instructions for administration.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1 μg to 1000 mg may be administered; in some embodiments, 10, 30, 100 or 1000 μg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the disclosure can be inserted into expression constructs, e.g., viral vectors, retroviral vectors, expression cassettes, or plasmid viral vectors, e.g., using methods known in the art, including but not limited to those described in Xia et al., (2002), Supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the disclosure can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

In certain exemplary embodiments, a composition that includes an RNA silencing agent of the disclosure can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. A preferred route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present disclosure may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the disclosure is delivered across the Blood-Brain-Barrier (BBB) suing a variety of suitable compositions and methods described herein.

The route of delivery can be dependent on the disorder of the patient. For example, a subject diagnosed with a neurodegenerative disease can be administered an RNA silencing agent of the disclosure directly into the brain (e.g., into the globus pallidus or the corpus striatum of the basal ganglia, and near the medium spiny neurons of the corpus striatum). In addition to an RNA silencing agent of the disclosure, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, CA). In one embodiment, a pump and reservoir are implanted in an area distant from the tissue, e.g., in the abdomen, and delivery is affected by a conduit leading from the pump or reservoir to the site of release. Devices for delivery to the brain are described, for example, in U.S. Pat. Nos. 6,093,180, and 5,814,014.

An RNA silencing agent of the disclosure can be further modified such that it is capable of traversing the blood brain barrier. For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the disclosure. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; El-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; EL Andaloussi S, Mäger I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mager I, Wood M J. (2013). Exosomes for targeted siRNA delivery across biological barriers. Adv Drug Deliv Rev. 2013 March; 65(3): 391-7. doi: 10.1016/j.addr.2012.08.008).

In certain embodiments, one or more lipophilic molecules are used to allow delivery of an RNA silencing agent of the disclosure past the BBB (Alvarez-Ervit (2011)). The RNA silencing agent would then be activated, e.g., by enzyme degradation of the lipophilic disguise to release the drug into its active form.

In certain embodiments, one or more receptor-mediated permeabilizing compounds can be used to increase the permeability of the BBB to allow delivery of an RNA silencing agent of the disclosure. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA silencing agent of the disclosure across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA silencing agent of the disclosure can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the disclosure can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration preferably do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA silencing agent of the disclosure can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-beta-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An RNA silencing agent of the disclosure can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

An RNA silencing agent can be packaged in a viral natural capsid or in a chemically or enzymatically produced artificial capsid or structure derived therefrom.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

Example 1. Synthesis of a 2'-OMe-exNA Phosphoramidite

Synthesis of Compound 5a

Figure 2:
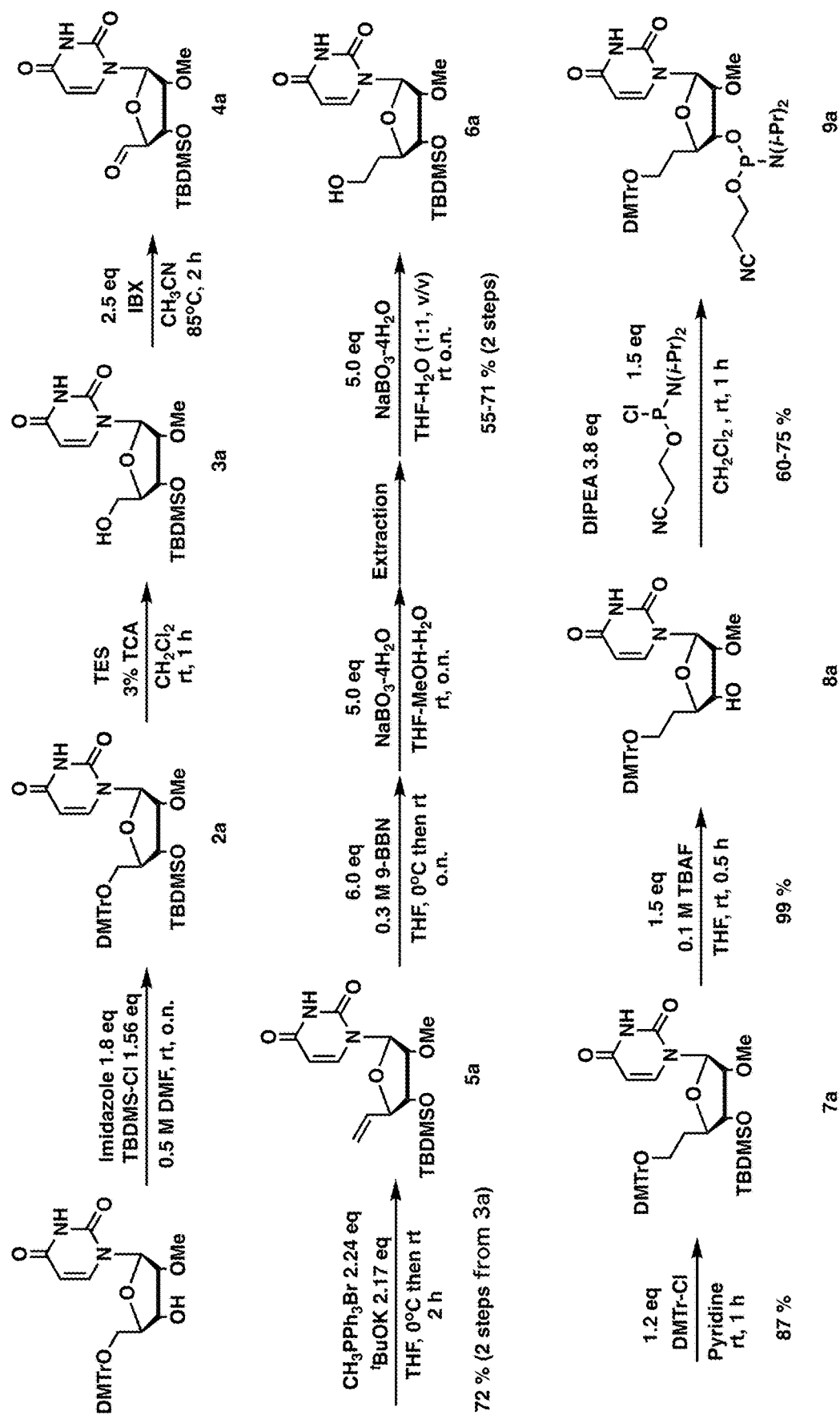

According to FIG. 2, the following synthesis was completed. Anhydrous solution of compound 3a (2.94 g, 7.89 mmol) in $CH_3CN$ (80 mL) was added IBX (5.53 g, 19.7 mmol) and stirred for 2 h at 85° C. After cooling the mixture in an ice bath, the precipitate in the solution was filtered off through celite. Collected eluent was evaporated, co-evaporated with anhydrous $CH_3CN$ three times under argon atmosphere, and obtained compound 4a as a white foam was used without further purification. In a separate flask, anhydrous THF (80 mL) solution containing methyltriphenylphosphonium bromide (8.47 g, 23.7 mmol) was added tert-BuOK (2.57 g, 22.9 mmol) at 0° C. and stirred for 30 min at 0° C. To this solution, anhydrous THF solution (80 mL) of compound 4a was added dropwise (10 min) at 0° C. and stirred for 7 h at rt. After evaporating excess THF, the obtained mixture was dissolved in excess ethyl acetate, washed by aq. sat. $NH_4Cl$, dried over $MgSO_4$, filtered, and evaporated. Obtained material was dissolved into minimum amount of $CH_2Cl_2$ and added dropwise to excess diethyl ether solution under vigorously stirring at 0° C. Precipitate in solution was filtered off through celite and eluents was evaporated. Obtained crude material was purified by silica gel column chromatography (hexane/ethyl acetate, 9:1 to 1:2) yielding compound 5a as a white foam (2.19 g, 75% in 2 steps). $^1$H NMR (500 MHz, $CDCl_3$) δ 9.55 (br-s, 1H), 7.38 (d, 1H, J=8.2 Hz), 5.89 (ddd, 1H, J=17.1, 10.6, 6.6 Hz), 5.82 (d, 1H, J=2.0 Hz), 5.77 (dd, 1H, J=8.1, 1.5 Hz), 5.44 (dt, 1H, J=17.2, 1.2 Hz), 5.34 (dt, 1H, J=10.5, 1.1 Hz), 4.43-4.40 (m, 1H), 3.90 (dd, 1H, J=7.7, 5.1 Hz), 3.71 (dd, 1H, J=5.0, 2.0 Hz), 3.55 (s, 3H), 0.89 (s, 9H), 0.09 (s, 3H), 0.07 (s, 3H); $^{13}$C NMR (125 MHz, $CDCl_3$) δ 163.4, 150.0, 139.7, 134.4, 119.2, 102.4, 89.7, 84.0, 83.5, 74.5, 58.7, 25.7, 18.2, −4.6, −4.7; HRMS (ESI) calcd. for $C_{17}H_{29}N_2O_5Si^+[M+H]^+$ m/z 369.1840, found m/z 369.1838.

Synthesis of Compound 6a

Anhydrous solution of compound 5a (7.29 g, 19.8 mmol) in THF (158.3 mL) was added 0.5 M 9-BBN/THF solution (237.4 mL, 118.7 mmol) dropwise for 10 min at 0° C. After stirring the mixture at rt 6 h, the solution was iced and added methanol (65.4 mL) and stirred until bubbling cease down. Then under vigorous stirring, $H_2O$ (98.4 mL) was added dropwise for 10 min to avoid precipitation of an intermediate compound. At 0° C., $NaBO_3$-$4H_2O$ (15.7 g, 102.0 mmol) was added in one portion and stirred at rt o.n. After evaporation of excess THF, obtained crude mixture was dissolved into excess ethyl acetate, and washed repeatedly by sat. aq. $NH_4Cl$ solution. After evaporating organic layer, obtained material was dissolved in THF (450 mL) and $H_2O$ (450 mL). To this solution, $NaBO_3$-$4H_2O$ (15.7 g, 102.0 mmol) was added in one portion at rt, then stirred o.n. at rt. After evaporating of excess THF, the mixture was added ethyl acetate, then extracted. Obtained organic layer was repeatedly washed by aq. sat. $NH_4Cl$, dried over $MgSO_4$, filtered, and evaporated. Obtained crude material was purified by silica gel column chromatography (hexane/ethyl acetate, 7:3 to 0:10) yielding compound 6a as a white foam (4.73 g, 62% in 2 steps). $^1$H NMR (500 MHz, $CDCl_3$) δ 9.21 (br-s, 1H), 7.35 (d, 1H, J=8.1 Hz), 5.78-5.76 (m, 2H), 4.14-4.10 (m, 1H), 3.92-3.79 (m, 4H), 3.75 (dd, 1H, J=5.2, 2.3 Hz), 2.06-2.00 (m, 1H), 1.90-1.82 (m, 1H), 0.91 (s, 9H), 0.11 (s, 3H), 0.10 (s, 3H); $^{13}$C NMR (125 MHz, $CDCl_3$) δ 163.1, 149.9, 140.0, 102.6, 90.1, 83.0, 82.0, 74.5, 60.3, 58.4, 35.5, 25.7, 18.1, −4.6, −4.9; HRMS (ESI) calcd. for $C_{17}H_{31}N_2O_5Si^+[M+H]^+$ m/z 387.1946, found m/z 187.1944.

Synthesis of Compound 8a

Anhydrous solution of compound 6a (9.46 g, 24.5 mmol) in pyridine (240 mL) was added DMTrCl (9.95 g, 29.4 mmol) and stirred at rt for 2 h. After quenching the reaction mixture by MeOH (20 mL), excess pyridine was evaporated, then obtained material was dissolved into excess ethyl acetate. The organic solution was washed by aq. sat. $NaHCO_3$, dried over $MgSO_4$, filtered, evaporated, then co-evaporated with toluene to remove pyridine residues. This crude mixture containing compound Tawas dissolved into THF (330 mL), added 1.0 M TBAF-THF solution (36.7 mL, 36.7 mmol), then stirred for 1 h at rt. After evaporation excess THF and co-evaporation with $CH_2Cl_2$, the crude material was purified by silica gel column chromatography yielding compound 8a (13.15 g, 93% in 2 steps). $^1$H NMR (500 MHz, $CDCl_3$) δ 8.91 (br-s, 1H), 7.43-7.21 (m, 2H), 7.32-7.14 (m, 8H), 6.83-6.82 (m, 1H), 5.80 (d, 1H, J=1.8 Hz), 5.69 (d, 1H, J=8.2 Hz), 4.02-3.98 (m, 1H), 3.85 (dd, 1H, J=6.7, 6.7 Hz), 3.79 (s, 6H), 3.72 (dd, 1H, J=5.5, 1.9 Hz), 3.34-3.25 (m, 2H), 2.91 (br-s, 1H), 2.11-2.04 (m, 1H), 1.95-1.89 (m, 1H); $^{13}$C NMR (125 MHz, $CDCl_3$) δ 163.2, 163.1, 158.4, 149.9, 114.8, 139.1, 136.1, 136.0, 129.92, 129.90, 128.0, 127.8, 126.8, 113.1, 102.5, 88.1, 86.6, 83.5, 81.3, 73.2, 60.1, 58.8, 55.2, 53.4, 33.4; HRMS (ESI) calcd. for $C_{32}H_{34}N_2O_8Na$ $[M+Na]^+$ m/z 597.2203, found m/z 597.2153.

Synthesis of Compound 9a

Compound 8a (9.57 g, 16.65 mmol) was rendered anhydrous by repeated co-evaporation with anhydrous $CH_3CN$ and then dissolved into anhydrous $CH_2Cl_2$ (150 mL). To this solution N,N-diisopropylethylamine (7.6 mL, 62.4 mmol) and 2-cyanoethyl N,N-diisopropylchlorophosphoramidite (4.85 mL, 25.0 mmol) were added at 0° C. After stirring for 4 h at rt, the reaction mixture was added $CH_2Cl_2$ (200 mL) then aq. sat. $NaHCO_3$ (350 mL). Organic layer was repeatedly washed by aq. sat. $NaHCO_3$, dried over $MgSO_4$, filtered, then evaporated. Obtained crude material was purified by silica gel column chromatography (1% TEA-hexanes-ethyl acetate, from 80:20 to 30:70) yielding compound 9a with an impurity of phosphitylating reagent residues. To remove the impurity, obtained material was dissolved in $Et_2O$-ethylacetate (1:1, v/v, 400 mL), then repeatedly washed by aq. sat. NaHCO₃ yielding compound 9a as a white solid (11.12 g, 86%); ³¹P NMR (202 MHz, CDCl₃) δ 150.0, 149.9; HRMS (ESI) calcd. for C₄₁H₅₂N₄O₉P [M+H]⁺ m/z 775.3486, found m/z 775.3414.

Example 2. Synthesis of a 2'-F-exNA Phosphoramidite

Synthesis of Compound 5b

Figure 3:
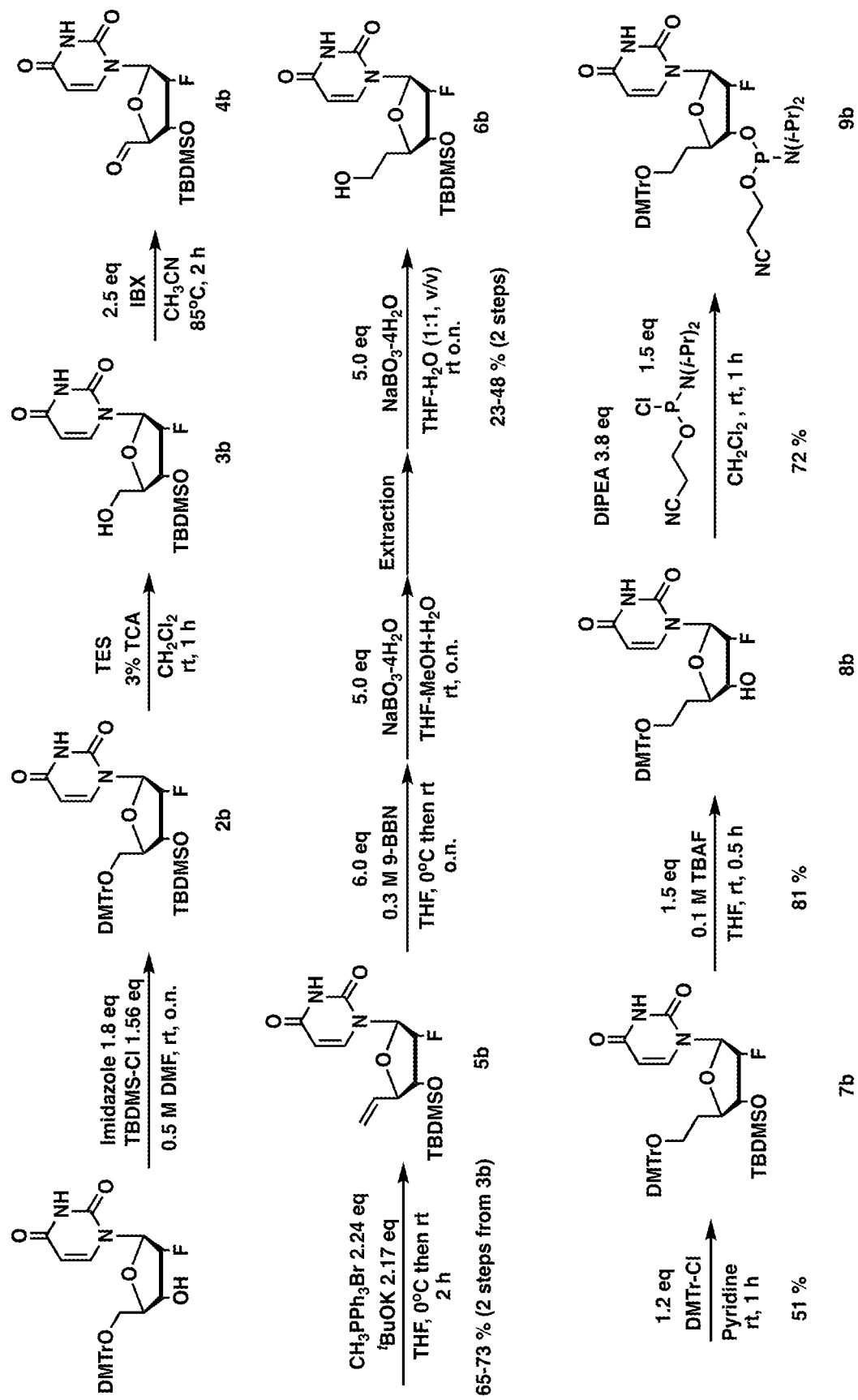
FIG. 3 provides a synthesis of a 2'-F-exNA phosphoramidite 9b.

According to FIG. 3, the following synthesis was completed. Anhydrous solution of compound 3b (10.8 g, 30.0 mmol) in CH₃CN (300 mL) was added IBX (21.0 g, 75.0 mmol) and stirred for 2 h at 85° C. After cooling the mixture in an ice bath, the precipitate in the solution was filtered off through celite. Collected eluent was evaporated, co-evaporated with anhydrous CH₃CN three times under argon atmosphere, and obtained compound 4b as a white foam was used without further purification. In a separate flask, anhydrous THF (250 mL) solution containing tert-BuOK (7.30 g, 65.1 mmol) was added methyltriphenylphosphonium bromide (24.0 g, 68.1 mmol) was added in one portion at 0° C. and stirred for 1 h at 0° C. To this solution, anhydrous THF solution (150 mL) of compound 4b was added dropwise (10 min) at 0° C. and stirred o.n. at rt. After evaporating excess THF, the obtained mixture was dissolved in excess ethyl acetate, washed by aq. sat. NH₄Cl, dried over MgSO₄, filtered, and evaporated. Obtained material was dissolved into minimum amount of CH₂Cl₂ and added dropwise to excess diethyl ether solution under vigorously stirring at 0° C. Precipitate in solution was filtered off through celite and eluents was evaporated. Obtained crude material was purified by silica gel column chromatography (hexane/ethyl acetate, 8:2 to 6:4) yielding compound 5b as a white foam (7.12 g, 67% in 2 steps). ¹H NMR (500 MHz, CDCl₃) δ 11.4 (br-s, 1H), 7.65 (d, 1H, J=8.1 Hz), 5.93 (ddd, 1H, J=17.5, 10.4, 7.5 Hz), 5.82 (dd, 1H, $J_{HF}$=22.2 Hz, $J_{HH}$=1.3 Hz), 5.65 (d, 1H, J=8.1 Hz), 5.42-5.38 (m, 1H), 5.33-5.31 (m, 1H), 5.15 (ddd, 1H, $J_{HF}$=53.4 Hz, $J_{HH}$=4.6, 1.2 Hz), 4.27 (ddd, 1H, $J_{HF}$=20.6 Hz, $J_{HH}$=8.4, 4.9 Hz), 4.18 (dd, 1H, J=7.7, 7.7 Hz), 0.88 (s, 9H), 0.08 (s, 3H), 0.07 (s, 3H); ¹³C NMR (125 MHz, CDCl₃) δ 170.8, 183.7, 150.7, 142.5, 135.3, 120.2, 102.4, 92.9 (d, $J_{CF}$=186.2 Hz), 90.2 (d, $J_{CF}$=36.4 Hz), 83.4, 73.8 (d, $J_{CF}$=15.5 Hz), 60.2, 26.0, 21.2, 18.2, 14.6, −4.4, −4.5; ¹⁹F NMR (470 MHz, DMSO-d6) δ −198.3 (ddd, J=53.8, 20.8, 20.8 Hz).

Synthesis of Compound 7b

Anhydrous solution of compound 5b (10.15 g, 28.5 mmol) in THF (228 mL) was added 0.5 M 9-BBN/THF solution (342 mL, 171 mmol) dropwise for 20 min at 0° C. After stirring the mixture at rt 4 h, the solution was iced and added methanol (131 mL) and stirred until bubbling cease down. Then under vigorous stirring, H₂O (197 mL) was added dropwise for 15 min to avoid precipitation of an intermediate compound. At 0° C., NaBO₃·4H₂O (21.9 g, 142.5 mmol) was added in one portion and stirred at rt o.n. After evaporation of excess THF, obtained crude mixture was dissolved into excess ethyl acetate, and washed repeatedly by sat. aq. NH₄Cl solution. After evaporating organic layer, obtained material was dissolved in THF (450 mL) and H₂O (450 mL). To this solution, NaBO₃·4H₂O (21.9 g, 142.5 mmol) was added in one portion at rt, then stirred o.n. at rt. After evaporating of excess THF, the mixture was added ethyl acetate, then extracted. Obtained organic layer was repeatedly washed by aq. sat. NH₄Cl, dried over MgSO₄, filtered, and evaporated. Obtained crude material was purified by silica gel column chromatography (CH₂Cl₂/methanol, 100:0 to 93:7) yielding compound 6b as a syrup (2.44 g with reagent impurity); HRMS (ESI) calcd. for C₁₆H₂₈FN₂O₅Si⁺[M+H]⁺ m/z 375.1746, found m/z 375.1746. This compound 6b with reagent impurity was rendered anhydrous by repeated co-evaporation with anhydrous pyridine under argon atmosphere, then dissolved in anhydrous pyridine (64 mL). To this solution, DMTrCl (2.64 g, 7.79 mmol) was added and stirred at rt for 1 h. After the reaction was quenched by addition of methanol (5 mL), reaction mixture was diluted with ethyl acetate (300 mL) and washed repeated by aq. sat. NaHCO3, dried over MgSO4, filtered, evaporated, then co-evaporated with toluene three times to remove remaining pyridine. Obtained crude material was purified by silica gel chromatography (hexane-ethyl acetate from 2:8 to 4:6) yielding compound 7b as a white solid (2.25 g, 12% in 2 steps). ¹H NMR (500 MHz, CD₃CN) δ 9.16 (br-s, 1H), 7.43-7.42 (m, 2H), 7.31-7.28 (m, 8H), 6.86-6.85 (m, 4H), 5.75 (dd, 1H, $J_{HF}$=20.0 Hz, $J_{HH}$=1.9 Hz), 5.59 (d, 1H, J=8.1 Hz), 4.96 (ddd, $J_{HF}$=53.3 Hz, $J_{HH}$=4.6, 1.8 Hz), 4.06-3.98 (m, 2H), 3.76 (s, 6H), 3.19 (dd, 2H, J=7.4, 5.6 Hz), 2.09-2.02 (m, 1H), 1.89-1.82 (m, 1H), 0.91 (s, 9H), 0.10 (s, 3H), 0.09 (s, 3H); ¹³C NMR (125 MHz, CD₃CN) δ 163 0.9, 159.6, 151.1, 146.4, 141.9, 137.31, 137.26, 130.92, 130.89, 128.9, 128.8, 127.8, 114.0, 102.9, 93.7 (d, $J_{CF}$=188.0 Hz), 90.6 (d, J=36.4 Hz), 87.0, 80.7, 74.6 (d, J=15.4 Hz), 60.9, 55.9, 33.8, 26.1, 18.7, −4.5, −4.8; ¹⁹F NMR (470 MHz, CD₃CN) δ-201.4 (ddd, J=53.7, 19.1, 19.1 Hz); HRMS (ESI) calcd. for C₃₇H₄₅FN₂O₇Na [M+Na]⁺ m/z 699.2872, found m/z 699.2866.

Synthesis of Compound 8b

Compound 7a (2.24 g, 3.30 mmol) was dissolved into THF (36.0 mL), then added 1.0 M TBAF-THF solution (4.0 mL, 4.0 mmol), then stirred for 30 min at rt. After evaporation excess THF and co-evaporation with CH₂Cl₂, the crude material was purified by silica gel column chromatography [CH₂Cl₂(1% TEA)-methanol from 100:0 to 95:5] yielding compound 8b (1.51 g, 81%). ¹H NMR (500 MHz, CDCl₃) δ 9.20 (br-s, 1H), 7.45-7.43 (m, 2H), 7.32-7.13 (m, 8H), 6.87-6.85 (m, 4H), 5.77 (dd, 1H, =20.1 Hz, JHH=1.5 Hz), 5.60 (d, 1H, J=8.1 Hz), 4.98 (ddd, JHF=51.0 Hz, JHH=4.6, 1.6 Hz), 4.04-3.92 (m, 2H), 3.76 (s, 6H), 3.23-3.17 (m, 2H), 2.20 (br-s, 1H), 2.11-2.06 (m, 1H), 1.91-1.87 (m, 1H); ¹³C NMR (125 MHz, CD₃CN) δ 164.1, 159.7, 151.2, 146.4 141.7, 139.0, 137.33, 137.29, 131,00, 130.97, 129.3, 129.0, 128.9, 127.8, 126.3, 114.1, 103.0, 94.7 (d, J=184.4 Hz), 90.3 (d, J=35.4 Hz), 87.2, 80.5, 73.9 (d, J=16.4 Hz), 61.0, 56.0, 33.9; ¹⁹F NMR (470 MHz, CD₃CN) (δ-201.8 (ddd, J=53.7, 20.8, 20.8 Hz).

Synthesis of Compound 9b

Compound 8b (1.5 g, 2.67 mmol) was rendered anhydrous by repeated co-evaporation with anhydrous CH₃CN and then dissolved into anhydrous CH₂Cl₂ (30 mL). To this solution N,N-diisopropylethylamine (1.76 mL, 10.1 mmol) and 2-cyanoethyl N,N-diisopropylchlorophosphoramidite (0.90 mL, 4.01 mmol) were added at 0° C. After stirring for 2 h at rt, the reaction mixture was added CH₂Cl₂ (70 mL) then aq. sat. NaHCO₃ (100 mL). Organic layer was repeatedly washed by aq. sat. NaHCO₃, dried over MgSO₄, filtered, then evaporated. Obtained crude material was purified by silica gel column chromatography (1% TEA-hexanes-ethyl acetate, from 80:20 to 20:80) yielding compound 9a with an impurity of phosphitylating reagent residues. To remove the impurity, obtained material was dissolved in Et₂O (100 mL), then repeatedly washed by aq. sat. NaHCO₃ yielding compound 9b as a white solid (1.47 g, 64%); ³¹P NMR (202 MHz, CDCl₃) δ 150.4 (d, J=9.0 Hz), 149.9 (d, J=10.0 Hz); ¹⁹F NMR (470 MHz, CD₃CN) (δ-198.61, −198.63, −198.66, −198.68, −198.70, −198.73, −198.75, −198.77, −198.79, −198.82, −198.84, −199.04, −199.06, −199.08, −199.10, −199.12, −199.14, −199.15, −199.17, −199.20, −199.21, −199.24, −199.26.

Example 3. Synthesis of an exNA-C Phosphoramidite

Figure 4:
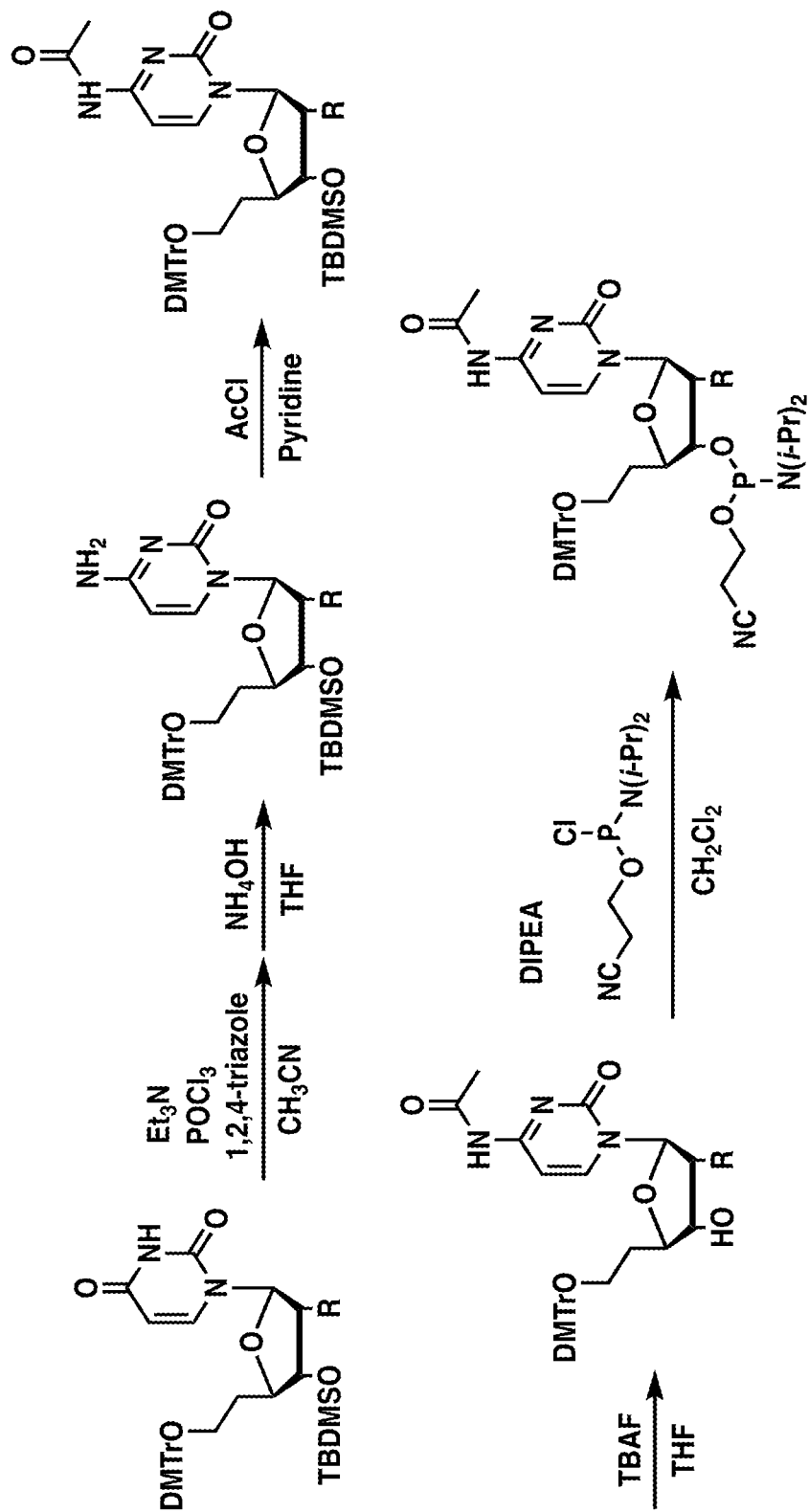
FIG. 4 provides a synthesis of an exNA-C phosphoramidite.

According to FIG. 4, the starting material will be first converted to cytidine derivative (Kaura, M. et al. J. Org. Chem. 2014, 79, 6256-6268), and then yielding 4-amino group of cytosine base will be protected by an acyl protecting group such as acetyl. After deprotection of 3'-O-TBDMS, yielding 3'-hydroxyl group will be converted to 3'-O-phosphoramidite. Each step will be first quenched and extracted followed by purification by silica gel column chromatography.

Example 4. Synthesis of an exNA-G and an exNA-A Phosphoramidite

Figure 5:
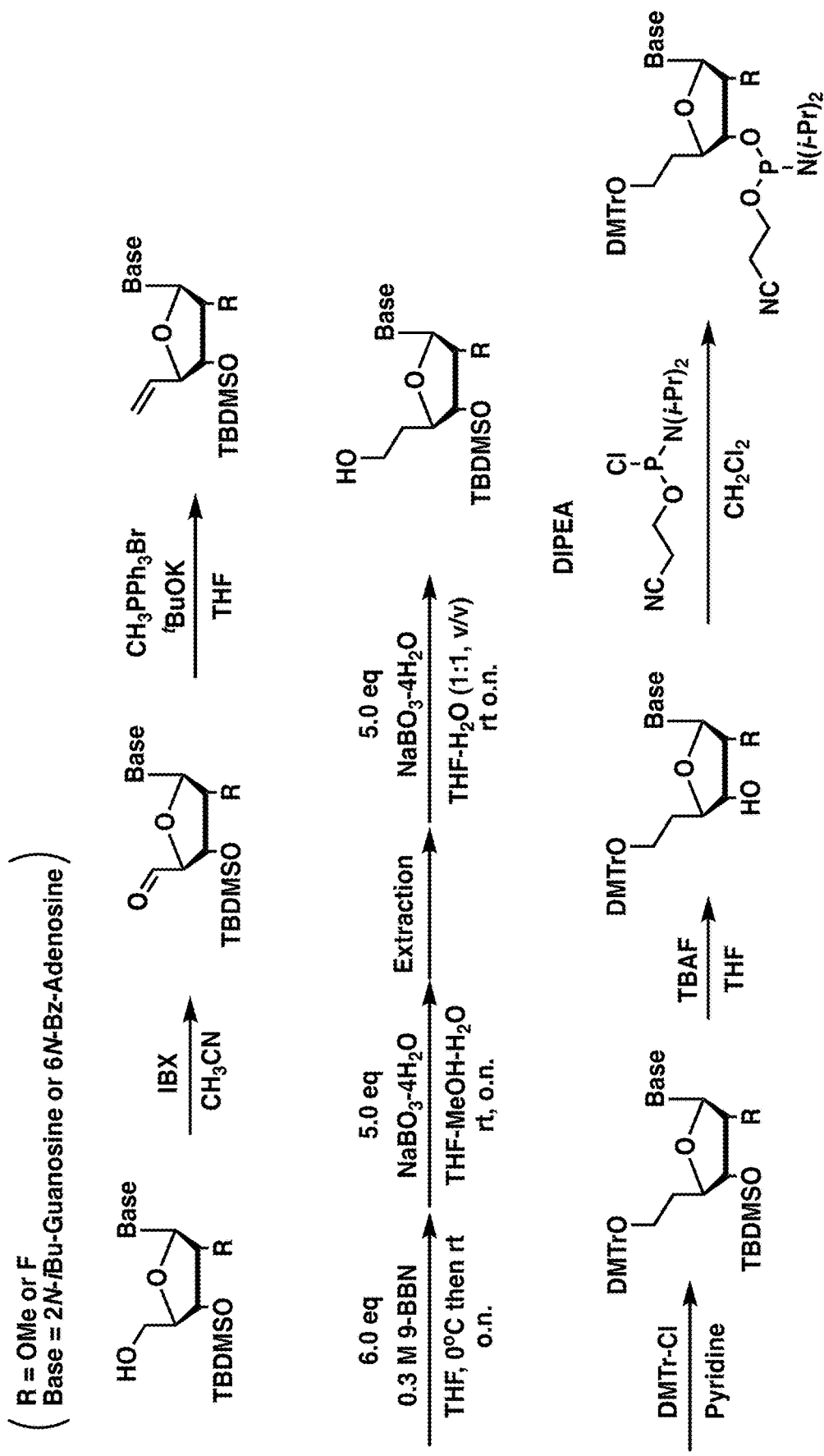
FIG. 5 provides a synthesis of an exNA-G and an exNA-A phosphoramidite.

According to FIG. 5, a 3'-O-TBDMS protected starting material will be first oxidized to aldehyde by using IBX, then applied to Wittig olefination using methyltriphenylphosphonium bromide and tert-BuOK in anhydrous THF solution to yield vinyl substituted nucleoside derivatives. This vinyl group will be reacted with 9-BBN to have boronated intermediate then forwarded to oxidation by sodium perborate yielding exNA structure with 6'-hydroxyl group. This hydroxyl group will be first protected by DMTr group, and without silica gel column purification, followed by deprotection of 3'-O-TBDMS group by 0.1 M TBAF-THF solution. Obtained 6'-O-DMTr nucleoside derivatives will be phosphitylated to yield phosphoramidites. Each step will be first quenched and extracted followed by purification by silica gel column chromatography except for the 6'-O-tritylation step.

Example 5. Synthesis of a 5'-3'-Bis-Methylene-exNA Phosphoramidite

Figure 6:
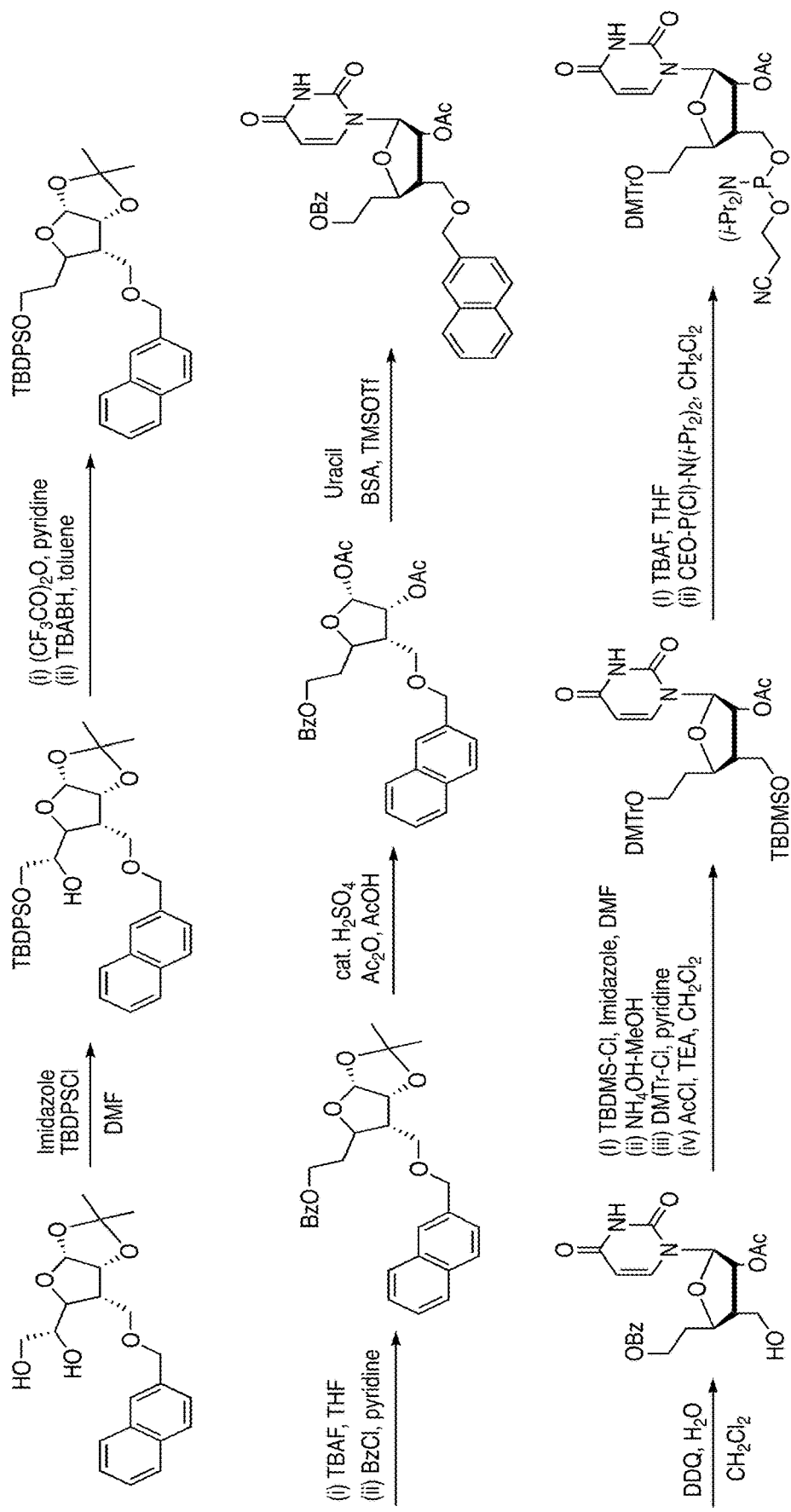
FIG. 6 provides a synthesis of a 5'-3'-bis-methylene-exNA phosphoramidite.

According to FIG. 6, a primary hydroxyl group of a starting material having Nap-protected hydroxymethyl group (Betkekar, V. V. et al. Org. Lett. 2012, 14, 1, 198-201) will be first selectively protected by TBDPS group, followed by deoxygenation of secondary alcohol (Prakash, T. P. et al. Nucleic Acids Res. 2015, 43, 2993-3011). Next, TBDPS group will be switched to benzoyl (Bz) protecting group by deprotection in 0.1M TBAF-THF solution and benzoylation using benzoyl chloride in pyridine. Isopropylidene protecting group of the sugar will next deprotected to yield 1,2-bis-acetylated sugar, then conventional BSA/TMSOTf-mediated glycosylation of uracil will be conducted to have uridine nucleoside derivative. The Nap protecting group at 3'-hydroxymethyl group will be deprotected by DDQ. Obtaining material having 6'-O-Bz-3'-hydroxymethyl group will be converted to 6'-O-DMTr-3'-TBDMS-protected hydroxymethyl compound with 2'-O-acetyl protection. After deprotection of TBDMS group, 3'-hydroxymethyl group will be phosphitylated to yield 5'-3'-bis-exNA-phosphoramidite. Each step will be first quenched and extracted followed by purification by silica gel column chromatography.

Example 6. Synthesis of an exNA-Ribo-Uridine Phosphoramidite

Figure 7:
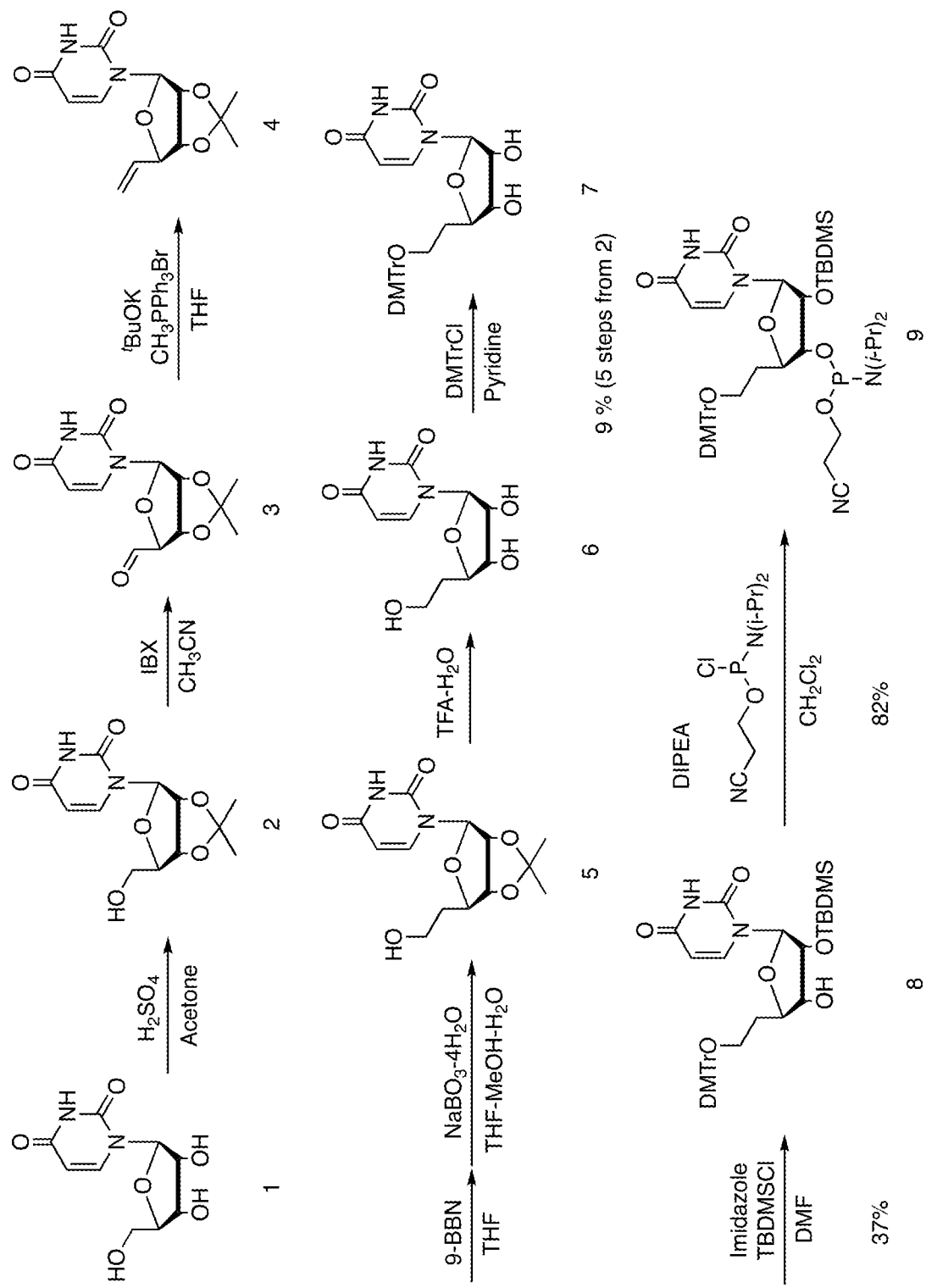
FIG. 7 provides a synthesis of an exNA-ribo-uridine phosphoramidite.
Figure 8:
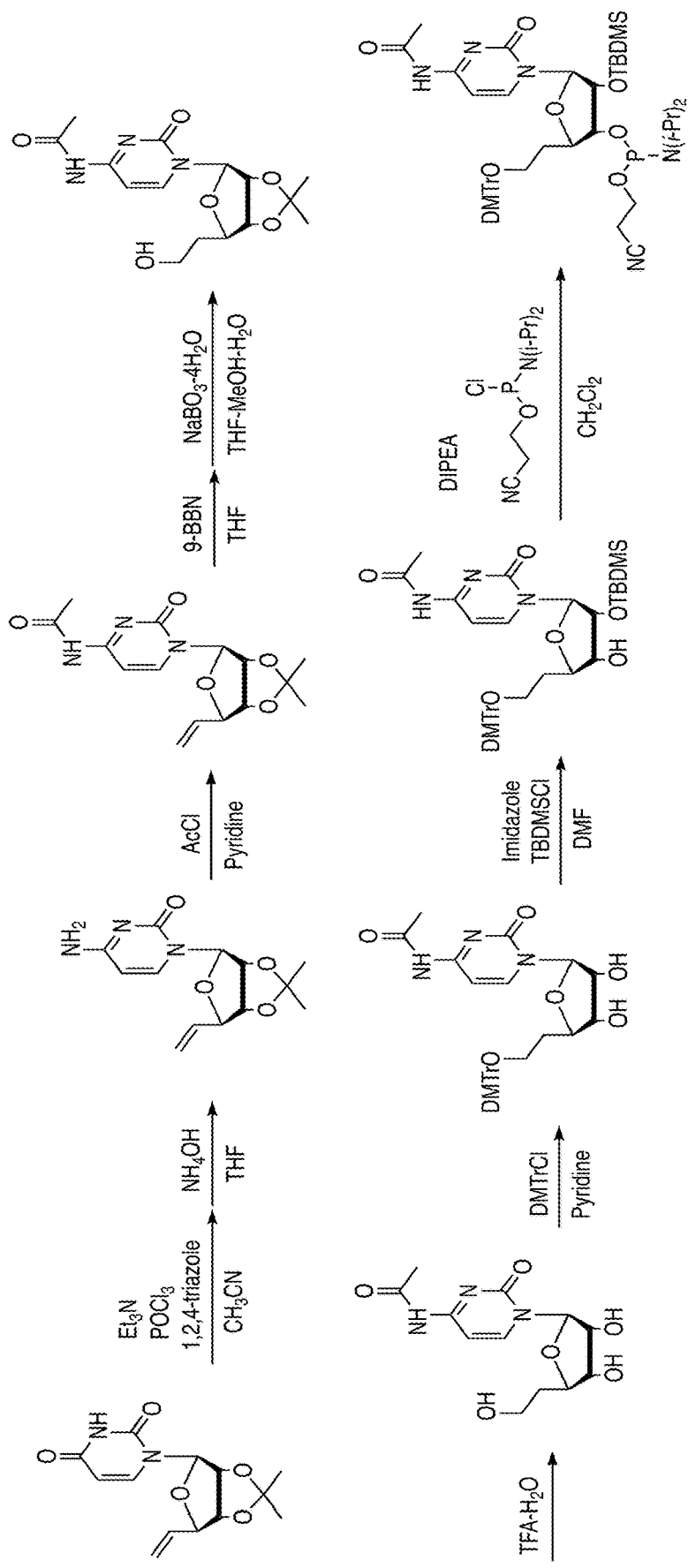
FIG. 8 provides a synthesis of an exNA-ribo-cytosine phosphoramidite.

According to FIG. 7., the following synthesis was completed. Anhydrous solution of compound 2 (15.4 g, 54.1 mmol) in $CH_3CN$ (520 mL) was added IBX (30.3 g, 108.2 mmol) and stirred for 2 h at 85° C. After cooling the mixture in an ice bath, the precipitate in the solution was filtered off through celite. Collected eluent was evaporated, co-evaporated with anhydrous $CH_3CN$ three times under argon atmosphere, and obtained compound 3 as a white foam was used without further purification. In a separate flask, anhydrous THF (500 mL) solution containing tert-BuOK (13.2 g, 117.4 mmol) was added methyltriphenylphosphonium bromide (43.3 g, 121.2 mmol) was added in one portion at 0° C. and stirred for 1 h at 0° C. To this solution, anhydrous THF solution (150 mL) of compound 3 was added dropwise (10 min) at 0° C. and stirred for 4 h. at rt. After evaporating excess THF, the obtained mixture was dissolved in excess ethyl acetate, washed by aq. sat. $NH_4Cl$, dried over $MgSO_4$, filtered, and evaporated. Obtained material was dissolved into minimum amount of $CH_2Cl_2$ and added dropwise to excess diethyl ether solution under vigorously stirring at 0° C. Precipitate in solution was filtered off through celite and eluents was evaporated. Obtained crude material was purified by silica gel column chromatography (hexane/ethyl acetate, 8:2 to 3:7) yielding compound 4 with impurity of triphenylphosphineoxide. ¾ of this crude material was rendered anhydrous by repeated co-evaporation with anhydrous $CH_3CN$, and then dissolved in anhydrous THF (200 mL). To this solution, 0.5 M 9-BBN/THF (300 mL, 150.0 mmol) was added dropwise for 10 min, then stirred at rt o.n. After confirming disappearance of starting material by TLC, the solution was iced, then added methanol (200 mL) dropwise for 10 min. After bubbling is cease down, $H_2O$ (300 mL) was added dropwise then $NaBO_3$-$4H_2O$ (19.2 g, 125.0 mmol) was added in one portion. The solution was stirred o.n. at rt. After evaporation of excess THF, obtained crude mixture was dissolved into excess ethyl acetate, and washed repeatedly by sat. aq. $NH_4Cl$ solution. After evaporating organic layer, obtained material was dissolved in THF (400 mL) and $H_2O$ (400 mL). To this solution, $NaBO_3$-$4H_2O$ (19.2 g, 125.0 mmol) was added in one portion at rt, then stirred o.n. at rt. After evaporating of excess THF, the mixture was added ethyl acetate, then extracted. Obtained organic layer was repeatedly washed by aq. sat. $NH_4Cl$, dried over $MgSO_4$, filtered, and evaporated. Obtained crude material was purified by silica gel column chromatography ($CH_2Cl_2$-methanol, 100:0 to 93:7) yielding compound 5 with impurity of reagent residues. This obtained material was added TFA solution [TFA (85 mL) and $H_2O$ (9.2 mL)] and stirred at 0° C. for 1 h. After evaporation, co-evaporation with toluene four times, crude material was purified by silica gel column chromatography ($CH_2Cl_2$-MeOH from 100:0 to 90:10) yielding compound 6 (760 mg, 12% in 3 steps). $^1H$ NMR (500 MHz, DMSO-d6) δ 11.4 (br-s, 1H), 7.58 (d, 1H, J=5.0 Hz), 5.71 (d, 1H, J=5.0 Hz), 5.64 (dd, 1H, J=8.0, 2.2 Hz), 5.34 (d, 1H, J=5.2 Hz), 5.09 (d, 1H, J=4.7 Hz), 4.51 (br-s, 1H), 4.06, (dd, 1H, J=9.8, 4.9 Hz), 3.80-3.78 (m, 1H), 3.53-3.45 (m, 2H), 1.84-1.70 (m, 2H); $^{13}C$ NMR (125 MHz, DMSO-d6) δ 163.5, 151.1, 141.6, 102.5, 89.0, 80.9, 73.5, 73.2, 58.0, 46.2, 36.8, 9.1; HRMS (ESI) calcd. for $C_{10}H_{14}N_2O_6Na$ $[M+Na]^+$ m/z 281.0744, found m/z 281.0730.

Synthesis of Compound 7

The compound 6 (760 mg, 2.94 mmol) was added anhydrous pyridine (30 mL) and then added DMTr-Cl (1.3 g, 3.82 mmol). After stirring for 2 h, reaction mixture was first extracted with $CH_2Cl_2$ an aq. sat. $NaHCO_3$, and organic layer was dried over $MgSO_4$, filtered, evaporated, co-evaporated to remove pyridine. Obtained crude material was purified by silica gel column chromatography ($CH_2Cl_2$-

MeOH from 100:0 to 95:5) yielding compound 7 (1.70 g, quant). HRMS (ESI) calcd. for $C_{31}H_{32}N_2O_8Na$ $[M+Na]^+$ m/z 583.2051, found m/z 583.2025.

Synthesis of Compound 8

An anhydrous solution of compound 7 (2.35 g, 4.19 mmol) in pyridine (21 mL) was added imidazole (576.1 mg, 8.46 mmol) and TBDMSCl (1.10 g, 7.33 mmol), and then stirred for 2 h at rt. To this reaction mixture was added $CH_2Cl_2$ (150 mL) then added aq. sat. $NaHCO_3$ (150 mL). The organic layer was repeatedly washed by aq. sat. $NaHCO_3$, dried over $MgSO_4$, filtered, evaporated, then co-evaporated with toluene to remove pyridine residue. Obtained crude material containing compound 8, 3'-O-TBDMS protected compound, 5'-3'-O-bis-TBDMS protected compound was separated by silica gel column chromatography [$CH_2Cl_2$ (1% TEA)-Acetone from 100:0 to 85:15] yielding pure compound 8 (780 mg, 28%). $^1H$ NMR (500 MHz, DMSO-d6) δ 11.4 (br-s, 1H), 7.53-7.52 (m, 2H), 7.39-7.22 (m, 8H), 6.89-6.88 (m, 4H), 5.72 (d, 1H, J=5.0 Hz), 5.62 (d, 1H, J=8.1, 2.0 Hz), 5.00 (d, 1H, J=6.0 Hz), 4.19 (dd, 1H, J=5.1, 5.1 Hz), 3.92 (ddd, 1H, J=8.8, 8.8, 4.5 Hz), 3.78-3.73 (m, 7H), 3.07-3.03 (m, 2H), 2.05-1.83 (m, 2H), 0.83 (s, 9H), 0.05 (s, 3H), 0.01 (s, 3H); $^{13}C$ NMR (125 MHz, DMSO-d6) 162.9, 158.0, 150.5, 145.1, 140.7, 135.8, 130.1, 129.4, 128.7, 128.3, 128.1, 127.1, 125.8, 113.6, 102.5, 88.8, 86.0, 81.5, 74.9, 73.4, 60.6, 55.5, 33.8, 26.1, 25.1, 18.4; HRMS (ESI) calcd. for $C_{37}H_{46}N_2O_8Na$ $[M+Na]^+$ m/z 697.2916, found m/z 697.2867.

Synthesis of Compound 9

Compound 8 (780 g, 1.16 mmol) was rendered anhydrous by repeated co-evaporation with anhydrous $CH_3CN$ and then dissolved into anhydrous $CH_2Cl_2$ (12 mL). To this solution N,N-diisopropylethylamine (0.53 mL, 4.34 mmol) and 2-cyanoethyl N,N-diisopropylchlorophosphoramidite (0.34 mL, 1.73 mmol) were added at 0° C. After stirring for 4 h at rt, the reaction mixture was added $CH_2Cl_2$ (90 mL) then aq. sat. $NaHCO_3$ (100 mL). Organic layer was repeatedly washed by aq. sat. $NaHCO_3$, dried over $MgSO_4$, filtered, then evaporated. Obtained crude material was purified by silica gel column chromatography (1% TEA-hexanes-ethyl acetate, from 80:20 to 50:50) yielding compound 9 (825.9 mg, 82%). $^{31}P$ NMR (202 MHz, $CDCl_3$) δ 149.6, 149.1.

Example 7. Synthesis of an exNA-Ribo-Cytosine Phosphoramidite

Starting material bearing vinyl substituted uridine derivative will be first converted to cytidine (Kaura, M. et al. *J. Org. Chem.* 2014, 79, 6256-6268), and then yielding 4-amino group of cytosine base will be protected by an acyl protecting group such as acetyl. After deprotection of 2'-3'-O-isopropylidene, 6'-hydroxyl group will be protected by DMTr followed by TBDMS protection. Silica gel column separated 2'-O-TBDMS protected compound will be phosphitylated to yield 3'-O-phosphoramidite. Each step will be first quenched and extracted followed by purification by silica gel column chromatography.

Figure 9:
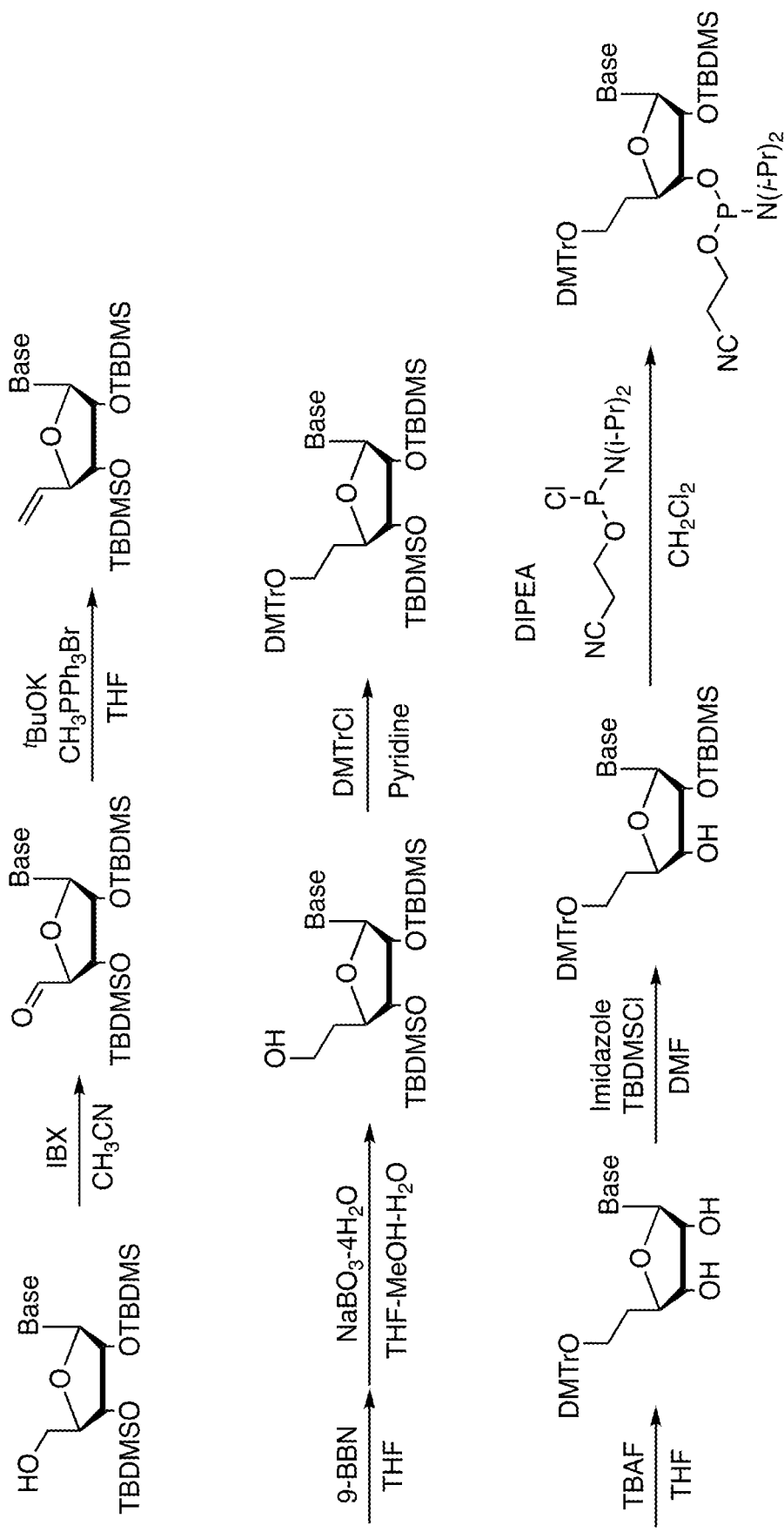
FIG. 9 provides a synthesis of an exNA-ribo-guanosine or exNA-ribo-adenine phosphoramidite.

Example 8. Synthesis of an exNA-Ribo-Guanosine or exNA-Ribo-Adenine Phosphoramidite According to FIG. 9., 2'-3'-O-bis-TBDMS protected starting material will be first oxidized to aldehyde by using IBX, then applied to Wittig olefination using methyltriphenylphosphonium bromide and tert-BuOK in anhydrous THF solution to yield vinyl substituted nucleoside derivatives. This vinyl group will be reacted with 9-BBN to have boronated intermediate then forwarded to oxidation by sodium perborate yielding exNA structure with 6'-hydroxyl group. This hydroxyl group will be first protected by DMTr group followed by TBDMS protection. Silica gel column separated 2'-O-TBDMS protected compound will be phosphitylated to yield 3'-O-phosphoramidite. Each step will be first quenched and extracted followed by purification by silica gel column chromatography. and without silica gel column purification, followed by deprotection of 3'-O-TBDMS group by 0.1 M TBAF-THF solution. Obtained 6'-O-DMTr nucleoside derivatives will be phosphitylated to yield phosphoramidites. Each step will be first quenched and extracted followed by purification by silica gel column chromatography.

Example 9. Synthesis of an exNA-Ribo-Uridine Phosphoramidite

Figure 10:
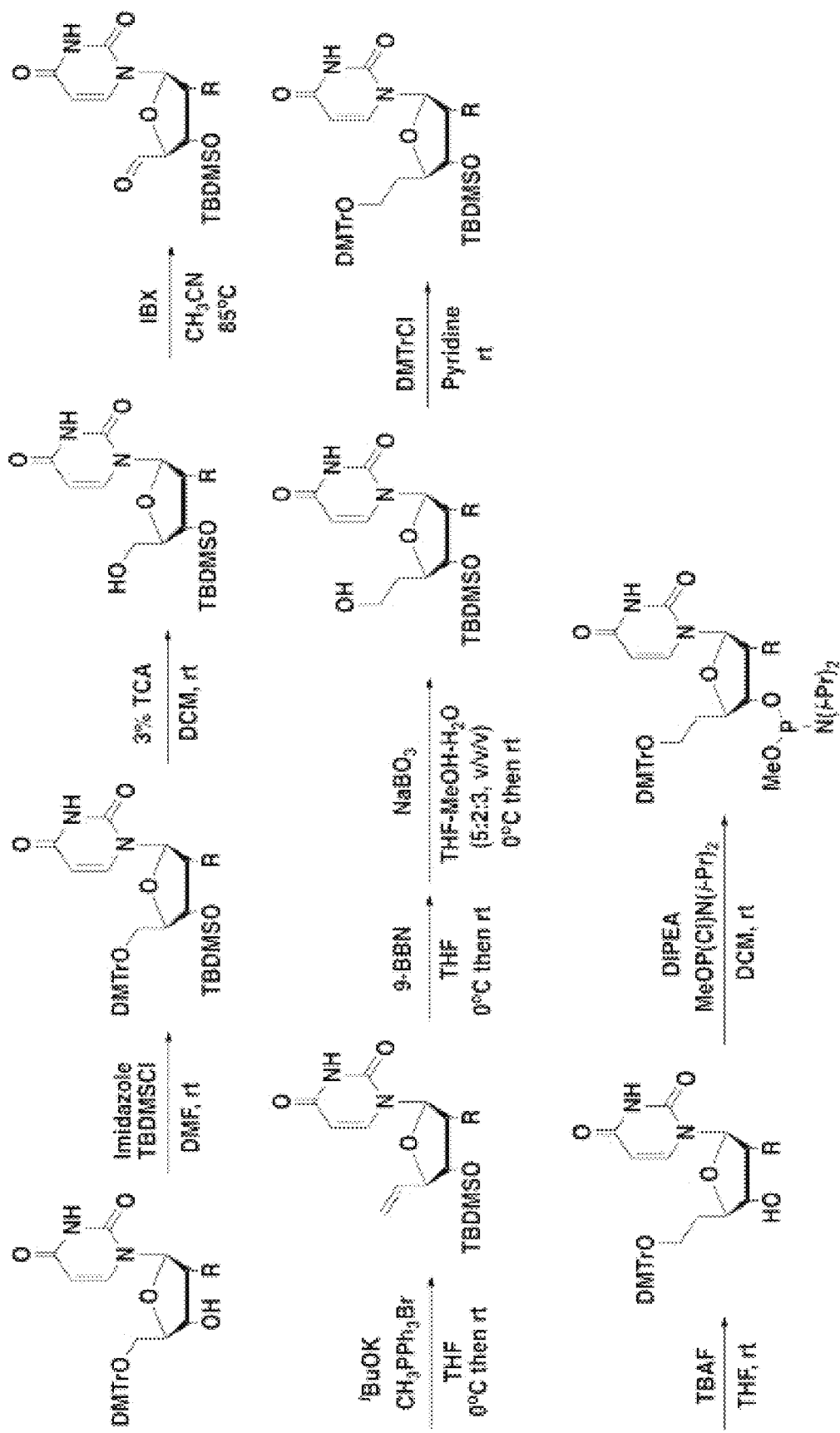
FIG. 10 provides a synthesis of a phosphoramidite monomer.

According to FIG. 10, 5'-O-DMTr protected starting material will be first protected by TBDMS, then followed by 5'-O-detritylation. Obtained compound will be next oxidized to aldehyde by using IBX, then applied to Wittig olefination using methyltriphenylphosphonium bromide and tert-BuOK in anhydrous THF solution to yield vinyl substituted nucleoside derivatives. This vinyl group will be reacted with 9-BBN to have boronated intermediate then forwarded to oxidation by sodium perborate yielding exNA structure with 6'-hydroxyl group. This hydroxyl group will be first protected by DMTr group, and without silica gel column purification, followed by deprotection of 3'-O-TBDMS group by 0.1 M TBAF-THF solution. Obtained 6'-O-DMTr nucleoside derivatives will be phosphitylated to yield methyl protected phosphoramidites. Each step will be first quenched and extracted followed by purification by silica gel column chromatography except for the first 3'-O-TBDMS protection step.

Example 10. Synthesis of Oligonucleotides Incorporating exNA Backbones

Figure 12:
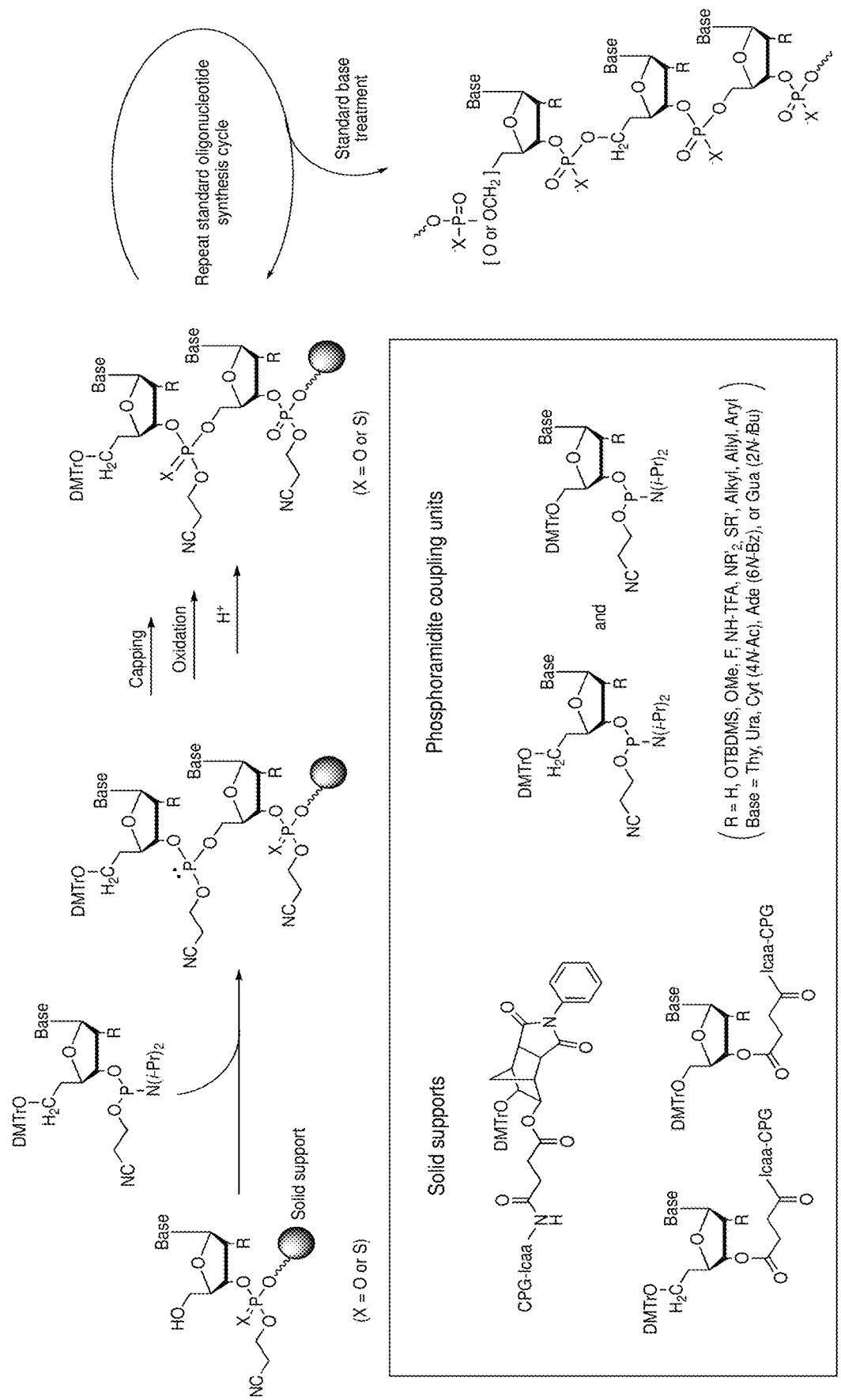
FIG. 12 provides synthesis for oligonucleotides incorporating exNA backbones.

According to FIG. 12., a method for synthesizing a modified oligonucleotide comprising a 5' end, a 3' end and at least one modified intersubunit linkage has been done. The method includes (a) providing a nucleoside having a 5'-protecting group linked to a solid support; (b) removal of the protecting group; (c) combining the deprotected nucleoside with a phosphoramidite derivative of Formula (VII) to form a phosphite triester;

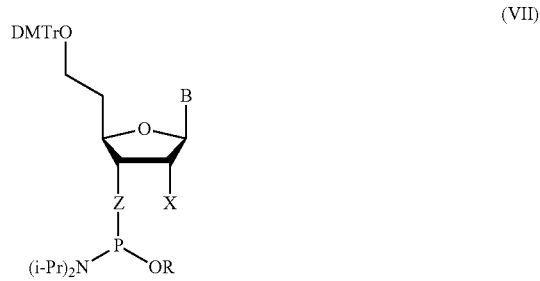

(VII)

(d) capping the phosphite triester; (e) oxidizing the phosphite triester; (f) repeating steps (b) through (e) using an additional phosphoramidite; and (g) cleaving from the solid support.

Examples of some oligonucleotides synthesized by the above method with one or more exNA-intersubunit linkages is shown in FIG. 13. The exNA-intersubunit linkages are 5'-methylene-exNA-uridine with 2'-OH.

Example 11 In Vitro Silencing Efficacy of Target mRNA with siRNA Duplexes Containing exNA Intersubunit Linkages An ex-NA intersubunit linkages was used in an oligonucleotide walk experiment, where each intersubunit linkage in an antisense and sense strand was modified with the ex-NA intersubunit linkage. The ex-NA intersubunit linkage was either (ex_mU): 5'-methylene-exNA-uridine with 2'-OMe or (ex_fU): 5'-methylene-exNA-uridine with 2'-fluoro-ex-uridine. Tables 4-10 below show the antisense and sense strands used in this Example, as well as duplexes formed by different combinations of said antisense and sense strands. A novel synthesis scheme for generating ex-NA containing oligonucleotides was also employed as shown in FIG. 12.

TABLE 4

Antisense strands having ex-NA intersubunit linkages

| Name | Sequence (5'->3')[a] | SEQ ID NO: |
|---|---|---|
| ex-1 | 5'-P(ex_mU)#(fU)#(mA)(fA)(mU)(fC)(mU)(fC)(mU)(fU)(mU)(fA)(mC)#(fU)#(mG)#(fA)#(mU)#(fA)#(mU)#(fA) | 1 |
| ex-2 | 5'-P(mU)#(ex_fU)#(mA)(fA)(mU)(fC)(mU)(fC)(mU)(fU)(mU)(fA)(mC)#(fU)#(mG)#(fA)#(mU)#(fA)#(mU)#(fA) | 2 |
| ex-3 | 5'-P(mU)#(fU)#(ex_mU)(fU)(mU)(fA)(mA)(fA)(mU)(fC)(mC)(fU)(mG)#(fA)#(mG)#(fA)#(mA)#(fG)#(mA)#(fA) | 3 |
| ex-4 | 5'-P(mU)#(fU)#(mU)(ex_fU)(mU)(fA)(mA)(fA)(mU)(fC)(mC)(fU)(mG)#(fA)#(mG)#(fA)#(mA)#(fG)#(mA)#(fA) | 4 |
| ex-5 | 5'-P(mU)#(fU)#(mA)(fA)(ex_mU)(fC)(mU)(fC)(mU)(fU)(mU)(fA)(mC)#(fU)#(mG)#(fA)#(mU)#(fA)#(mU)#(fA) | 5 |
| ex-6 | 5'-P(mU)#(fC)#(mC)(fA)(mC)(ex_fU)(mA)(fU)(mG)(fU)(mU)(fU)(mU)#(fC)#(mA)#(fC)#(mA)#(fU)#(mA)#(fU) | 6 |
| ex-7 | 5'-P(mU)#(fU)#(mA)(fA)(mU)(fC)(ex_mU)(fC)(mU)(fU)(mU)(fA)(mC)#(fU)#(mG)#(fA)#(mU)#(fA)#(mU)#(fA) | 7 |
| ex-8 | 5'-P(mU)#(fC)#(mC)(fA)(mC)(fU)(mA)(ex_fU)(mG)(fU)(mU)(fU)(mU)#(fC)#(mA)#(fC)#(mA)#(fU)#(mA)#(fU) | 8 |
| ex-9 | 5'-P(mU)#(fU)#(mA)(fA)(mU)(fC)(mU)(fC)(ex_mU)(fU)(mU)(fA)(mC)#(fU)#(mG)#(fA)#(mU)#(fA)#(mU)#(fA) | 9 |
| ex-10 | 5'-P(mU)#(fU)#(mA)(fA)(mU)(fC)(mU)(fC)(mU)(ex_fU)(mU)(fA)(mC)#(fU)#(mG)#(fA)#(mU)#(fA)#(mU)#(fA) | 10 |
| ex-11 | 5'-P(mU)#(fU)#(mA)(fA)(mU)(fC)(mU)(fC)(mU)(fU)(ex_mU)(fA)(mC)#(fU)#(mG)#(fA)#(mU)#(fA)#(mU)#(fA) | 11 |
| ex-12 | 5'-P(mU)#(fC)#(mC)(fA)(mC)(fU)(mA)(fU)(mG)(fU)(mU)(ex_fU)(mU)#(fC)#(mA)#(fC)#(mA)#(fU)#(mA)#(fU) | 12 |
| ex-13 | 5'-P(mU)#(fC)#(mC)(fA)(mC)(fU)(mA)(fU)(mG)(fU)(mU)(fU)(ex_mU)#(fC)#(mA)#(fC)#(mA)#(fU)#(mA)#(fU) | 13 |
| ex-14 | 5'-P(mU)#(fU)#(mA)(fA)(mU)(fC)(mU)(fC)(mU)(fU)(mU)(fA)(mC)#(ex_fU)#(mG)#(fA)#(mU)#(fA)#(mU)#(fA) | 14 |
| ex-15 | 5'-P(mU)#(fG)#(mC)(fC)(mU)(fA)(mA)(fG)(mA)(fG)(mC)(fA)(mC)#(fA)#(ex_mU)#(fU)#(mU)#(fA)#(mG)#(fU) | 15 |
| ex-16 | 5'-P(mU)#(fG)#(mC)(fC)(mU)(fA)(mA)(fG)(mA)(fG)(mC)(fA)(mC)#(fA)#(mU)#(ex_fU)#(mU)#(fA)#(mG)#(fU) | 16 |
| ex-17 | 5'-P(mU)#(fU)#(mA)(fA)(mU)(fC)(mU)(fC)(mU)(fU)(mU)(fA)(mC)#(fU)#(mG)#(fA)#(ex_mU)#(fA)#(mU)#(fA) | 17 |
| ex-18 | 5'-P(mU)#(fC)#(mC)(fA)(mC)(fU)(mA)(fU)(mG)(fU)(mU)(fU)(mU)#(fC)#(mA)#(fC)#(mA)#(ex_fU)#(mA)#(fU) | 18 |
| ex-19 | 5'-P(mU)#(fU)#(mA)(fA)(mU)(fC)(mU)(fC)(mU)(fU)(mU)(fA)(mC)#(fU)#(mG)#(fA)#(mU)#(fA)#(ex_mU)#(fA) | 19 |

TABLE 4-continued

Antisense strands having ex-NA intersubunit linkages

| Name | Sequence (5'->3')<sup>a</sup> | SEQ ID NO: |
|---|---|---|
| ex-20 | 5'-P(mU)#(fC)#(mC)(fA)(mC)(fU)(mA)(fU)(mG)(fU)(mU)(fU)(mU)#(fC)#(mA)#(fC)#(mA)#(fU)#(mA)#(ex_fU) | 20 |

<sup>a</sup>(mN): 2'-OMe,
(fN): 2'-Fluoro,
(ex_mU): 5'-methylene-exNA-uridine with 2'-OMe:
(ex_fU): 5'-methylene-exNA-uridine with 2'-fluoro-ex-uridine,
P: Phosphate,
Phosphorothioate %

TABLE 5

Sense strands having ex-NA intersubunit linkages

| Name | Sequence (5'->3')<sup>a</sup> | SEQ ID NO: |
|---|---|---|
| ex-SS-1 | 5'-(ex_fU)#(mG)#(fA)(mA)(mA)(fC)(mA)(fU)(mA)(fG)(mU)(fG)#(mG)#(fA)-TegChol | 21 |
| ex-SS-2 | 5'-(fC)#(ex_mU)#(fC)(mA)(fG)(mG)(fA)(mU)(fU)(mU)(fA)(mA)(fA)#(mA)#(fA)-TegChol | 22 |
| ex-SS-3 | 5'-(fA)#(mA)#(ex_fU)(mG)(fU)(mU)(fG)(mU)(fG)(mA)(fC)(mC)(fG)#(mG)#(fA)-TegChol | 23 |
| ex-SS-4 | 5'-(fC)#(mA)#(fG)(ex_mU)(fA)(mA)(fA)(mG)(fA)(mG)(fA)(mU)(fU)#(mA)#(fA)-TegChol | 24 |
| ex-SS-5 | 5'-(fA)#(mA)#(fU)(mG)(ex_fU)(mU)(fG)(mU)(fG)(mA)(fC)(mC)(fG)#(mG)#(fA)-TegChol | 25 |
| ex-SS-6 | 5'-(fA)#(mA)#(fU)(mG)(fU)(ex_mU)(fG)(mU)(fG)(mA)(fC)(mC)(fG)#(mG)#(fA)-TegChol | 26 |
| ex-SS-7 | 5'-(fA)#(mU)#(fG)(mU)(fG)(mC)(ex_fU)(mC)(fU)(mU)(fA)(mG)(fG)#(mC)#(fA)-TegChol | 27 |
| ex-SS-8 | 5'-(fC)#(mU)#(fC)(mA)(fG)(mG)(fA)(ex_mU)(fU)(mU)(fA)(mA)(fA)#(mA)#(fA)-TegChol | 28 |
| ex-SS-9 | 5'-(fC)#(mU)#(fC)(mA)(fG)(mG)(fA)(mU)(ex_fU)(mU)(fA)(mA)(fA)#(mA)#(fA)-TegChol | 29 |
| ex-SS-10 | 5'-(fC)#(mU)#(fC)(mA)(fG)(mG)(fA)(mU)(fU)(ex_mU)(fA)(mA)(fA)#(mA)#(fA)-TegChol | 30 |
| ex-SS-11 | 5'-(fC)#(mU)#(fG)(mG)(fA)(mA)(fA)(mA)(fG)(mC)(ex_fU)(mG)(fA)#(mU)#(fA)-TegChol | 31 |
| ex-SS-12 | 5'-(fC)#(mA)#(fG)(mU)(fA)(mA)(fA)(mG)(fA)(mG)(fA)(ex_mU)(fU)#(mA)#(fA)-TegChol | 32 |
| ex-SS-13 | 5'-(fC)#(mA)#(fG)(mU)(fA)(mA)(fA)(mG)(fA)(mG)(fA)(mU)(ex_fU)#(mA)#(fA)-TegChol | 33 |
| ex-SS-14 | 5'-(fC)#(mU)#(fG)(mG)(fA)(mA)(fA)(mA)(fG)(mC)(fU)(mG)(fA)#(ex_mU)#(fA)-TegChol | 34 |
| ex-SS-15 | 5'-(fC)#(mA)#(fG)(mU)(fA)(mA)(fA)(mG)(fA)(mG)(fA)(mU)(fU)#(mA)#(ex_fU)-TegChol | 35 |

<sup>a</sup>(mN): 2'-OMe,
(fN): 2'-Fluoro,
(ex_mU): 2'-OMe-ex-uridine,
(ex_fU): 2'-fluoro-ex-uridine,
P: Phosphate,
Phosphorothioate,
TegChol: Tetraethyleneglycol-linked cholesterol

TABLE 6

Control antisense strands

| Name | Sequence (5'->3')<sup>a</sup> | SEQ ID NO: |
|---|---|---|
| AS-0 | 5'-P(mU)(fU)(mA)(fA)(mU)(fC)(mU)(fC)(mU)(fU)(mU)(fA)(mC)(fU)(mG)(fA)(mU)(fU)(mU)(fU) | 36 |
| AS-1 | 5'-P(mU)#(fU)#(mA)(fA)(mU)(fC)(mU)(fC)(mU)(fU)(mU)(fA)(mC)#(fU)#(mG)#(fA)#(mU)#(fA)#(mU)#(fA) | 37 |
| AS-2 | 5'-P(mU)#(fU)#(mA)(fA)(mU)(fC)(mU)(fC)(mU)(fU)(mU)(fA)(mC)#(fU)#(mG)#(fA)#(mU)#(fU)#(mU)#(fU) | 38 |
| AS-3 | 5'-P(mU)#(fU)#(mU)(fU)(mU)(fA)(mA)(fA)(mU)(fC)(mC)(fU)(mG)#(fA)#(mG)#(fA)#(mA)#(fG)#(mA)#(fA) | 39 |

TABLE 6-continued

Control antisense strands

| Name | Sequence (5'->3')[a] | SEQ ID NO: |
|---|---|---|
| AS-4 | 5'-P(mU)#(fC)#(mC)(fA)(mC)(fU)(mA)(fU)(mG)(fU)(mU)(fU)(mU)#(fC)#(mA)#(fC)#(mA)#(fU)#(mA)#(fU) | 40 |
| AS-5 | 5'-P(mU)#(fG)#(mC)(fC)(mU)(fA)(mA)(fG)(mA)(fG)(mC)(fA)(mC)#(fA)#(mU)#(fU)#(mU)#(fA)#(mG)#(fU) | 41 |
| AS-6 | 5'-P(mU)#(fA)#(mU)(fC)(mA)(fG)(mC)(fU)(mU)(fU)(mU)(fC)(mC)#(fA)#(mG)#(fG)#(mG)#(fU)#(mC)#(fG) | 42 |
| AS-7 | 5'-P(mU)#(fC)#(mC)(fG)(mG)(fU)(mC)(fA)(mC)(fA)(mA)(fC)(mA)#(fU)#(mU)#(fG)#(mU)#(fG)#(mG)#(fU) | 43 |
| AS-8 | 5'-P(mA)#(fU)#(mA)(fA)(mU)(fC)(mU)(fC)(mU)(fU)(mU)(fA)(mC)#(fU)#(mG)#(fA)#(mU)#(fA)#(mU)#(fA) | 44 |

[a](mN): 2'-OMe,
(fN): 2'-Fluoro,
P: Phosphate,
Phosphorothioate

TABLE 7

Control sense strands

| Name | Sequence (5'->3')[a] | SEQ ID NO: |
|---|---|---|
| SS-1 | 5'-(fC)#(mA)#(fG)(mU)(fA)(mA)(fA)(mG)(fA)(mG)(fA)(mU)(fU)#(mA)#(fA)-TegChol | 45 |
| SS-2 | 5'-(fC)#(mU)#(fC)(mA)(fG)(mG)(fA)(mU)(fU)(mU)(fA)(mA)(fA)#(mA)#(fA)-TegChol | 46 |
| SS-3 | 5'-(fU)#(mG)#(fA)(mA)(fA)(mA)(fC)(mA)(fU)(mA)(fG)(mU)(fG)#(mG)#(fA)-TegChol | 47 |
| SS-4 | 5'-(fA)#(mU)#(fG)(mU)(fG)(mC)(fU)(mC)(fU)(mU)(fA)(mG)(fG)#(mC)#(fA)-TegChol | 48 |
| SS-5 | 5'-(fC)#(mU)#(fG)(mG)(fA)(mA)(fA)(mA)(fG)(mC)(fU)(mG)(fA)#(mU)#(fA)-TegChol | 49 |
| SS-6 | 5'-(fA)#(mA)#(fU)(mG)(fU)(mU)(fG)(mU)(fG)(mA)(fC)(mC)(fG)#(mG)#(fA)-TegChol | 50 |
| SS-7 | 5'-(fC)#(mA)#(fG)(mU)(fA)(mA)(fA)(mG)(fA)(mG)(fA)(mU)(fU)#(mA)#(fU)-TegChol | 51 |

[a](m): 2'-OMe,
(fN): 2'-Fluoro,
Phosphorothioate,
TegChol: Tetraethyleneglycol-linked cholesterol

TABLE 8 siRNA duplexes (D1-D20) having ex-NA modified antisense strands

| | Duplex # | exNA modified Antisense strand | Sense strand | Corresponding control duplex# (See Group 3) |
|---|---|---|---|---|
| Group 1 exNA walk on Antisense strand | D1 | ex-1 | SS-1 | D40 |
| | D2 | ex-2 | SS-1 | D40 |
| | D3 | ex-3 | SS-2 | D42 |
| | D4 | ex-4 | SS-2 | D42 |
| | D5 | ex-5 | SS-1 | D40 |
| | D6 | ex-6 | SS-3 | D43 |
| | D7 | ex-7 | SS-1 | D40 |
| | D8 | ex-8 | SS-3 | D43 |
| | D9 | ex-9 | SS-1 | D40 |
| | D10 | ex-10 | SS-1 | D40 |
| | D11 | ex-11 | SS-1 | D40 |
| | D12 | ex-12 | SS-3 | D43 |
| | D13 | ex-13 | SS-3 | D43 |
| | D14 | ex-14 | SS-1 | D40 |
| | D15 | ex-15 | SS-4 | D44 |
| | D16 | ex-16 | SS-4 | D44 |
| | D17 | ex-17 | SS-1 | D40 |
| | D18 | ex-18 | SS-3 | D43 |
| | D19 | ex-19 | SS-1 | D40 |
| | D20 | ex-20 | SS-3 | D43 |

TABLE 9 siRNA duplexes (D25-D39) having ex-NA modified sense strands

| | Duplex # | Antisense strand | exNA modified Sense strand | Corresponding control duplex# (See Group 3) |
|---|---|---|---|---|
| Group 2 exNA walk on Sense strand | D25 | AS-3 | ex-SS-1 | D43 |
| | D26 | AS-2 | ex-SS-2 | D42 |
| | D27 | AS-6 | ex-SS-3 | D46 |
| | D28 | AS-1 | ex-SS-4 | D40 |
| | D29 | AS-6 | ex-SS-5 | D46 |
| | D30 | AS-6 | ex-SS-6 | D46 |
| | D31 | AS-4 | ex-SS-7 | D44 |
| | D32 | AS-2 | ex-SS-8 | D42 |
| | D33 | AS-2 | ex-SS-9 | D42 |
| | D34 | AS-2 | ex-SS-10 | D42 |
| | D35 | AS-5 | ex-SS-11 | D45 |
| | D36 | AS-1 | ex-SS-12 | D40 |
| | D37 | AS-1 | ex-SS-13 | D40 |
| | D38 | AS-5 | ex-SS-14 | D45 |
| | D39 | AS-7 | ex-SS-15 | D47 |

TABLE 10

Control siRNA duplexes

| | Duplex # | Antisense strands | Sense strands | Corresponding exNA-duplexes |
|---|---|---|---|---|
| Group3 Control duplexes | D40 | AS-1 | SS-1 | D1, 2, 5, 7, 9, 10, 11, 14, 17, 19, D28, 36, 37 |
| | D42 | AS-3 | SS-2 | D3, 4, D26, 32, 33, 34 |
| | D43 | AS-4 | SS-3 | D6, 8, 12, 13, 18, 20, D25 |
| | D44 | AS-5 | SS-4 | D15, 16, D31 |
| | D45 | AS-6 | SS-5 | D35, 38 |
| | D46 | AS-7 | SS-6 | D27, 29, 30 |
| | D47 | AS-8 | SS-7 | D39 |

The siRNA duplexes recited above were used in in vitro mRNA silencing experiments to determine relative silencing efficacy. Experimental details are described below.

In Vitro Screen.

1.5 µM siRNAs were passively delivered to cells. Cells were plated in Dulbecco's Modified Eagle's Medium containing 6% FBS at 8,000 cells per well in 96-well cell culture plates. siRNAs were diluted to twice the final concentration in OptiMEM (Carlsbad, CA; 31985-088), and 50 µL diluted siRNAs were added to 50 µL of cells, resulting in 3% FBS final. Cells were incubated for 72 hours at 37° C. and 5% $CO_2$.

Quantitative Analysis of Target mRNA.

mRNA was quantified from cells using the QuantiGene 2.0 assay kit (Affymetrix, QS0011). Cells were lysed in 250 µL diluted lysis mixture composed of one part lysis mixture (Affymetrix, 13228), two parts $H_2O$ and 0.167 µg/µL proteinase K (Affymetrix, QS0103) for 30 min at 55° C. Cell lysates were mixed thoroughly, and 40 µL of each lysate was added per well of a capture plate with 40 µL diluted lysis mixture without proteinase K and 20 µL diluted probe set. Probe sets for human HTT and Hypoxanthine Phosphoribosyltransferase (HPRT) (Affymetrix; #SA-50339, SA-10030) were diluted and used according to the manufacturer's recommended protocol. Datasets were normalized to HPRT Cell Treatment: Reporter Assay.

HeLa cells were grown and maintained in Gibco DMEM (ref. #11965-092) with 1% pen/strep and 10% heat inactivated FBS. Three days prior to treatment, two 10 $cm^2$ dishes were plated with $2 \times 10^6$ HeLa cells. The following day, DMEM was replaced with Gibco OptiMEM (ref #31985-070) and 6 µg of reporter plasmid was added to cells using Invitrogen Lipofectamine 3000 (ref #L3000-015), following the manufacturer's protocol. Cells were left in OptiMEM/lipofectamine overnight to allow for maximum reporter plasmid transfection. The following day, siRNA was diluted in Opti-MEM and added to 96-well white wall clear bottom tissue culture plate, in triplicate, for each reporter plasmid. HeLa cells transfected with reporter plasmids the night prior were resuspended in DMEM with 6% heat inactivated FBS (no pen/strep) at $0.15 \times 10^6$ cells/mL and added to plate containing siRNA.

Cells were lysed after 72 hours of treatment (100% confluency) with 1× Passive Lysis Buffer from Dual-Luciferase Assay System Pack (Promega ref #E1960). Following lysis, luminescence was read after addition of 50 µl Luciferase Assay Reagent II (Promega ref #E1960), then read a second time after addition of 50 µL/well of Stop and Glow reagent (Promega ref #E1960). Absorbances were normalized to untreated controls and graphed on a log scale.

Figure 14:
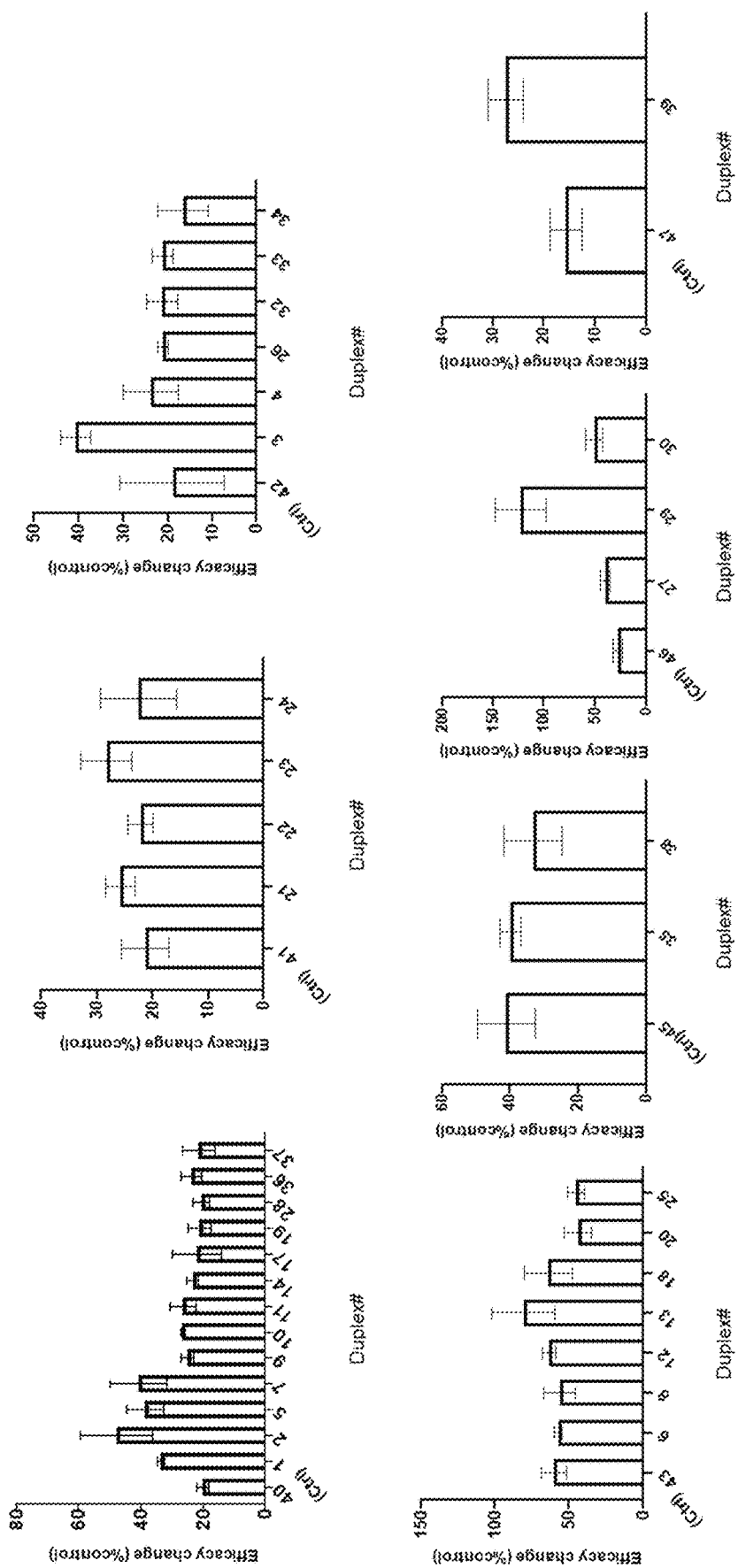
FIG. 14 provides results of in vitro silencing efficacy of target mRNA with siRNA duplexes containing exNA with intersubunit linkages at various positions.

As shown in FIG. 14, all tested siRNA duplexes effectively silenced the target HTT mRNA. Moreover, numerous siRNA duplexes silenced the target mRNA as well as the control duplex siRNA. This data provides the first example of an ex-NA internucleotide linkage incorporated into an oligonucleotide strand.

Figure 15:
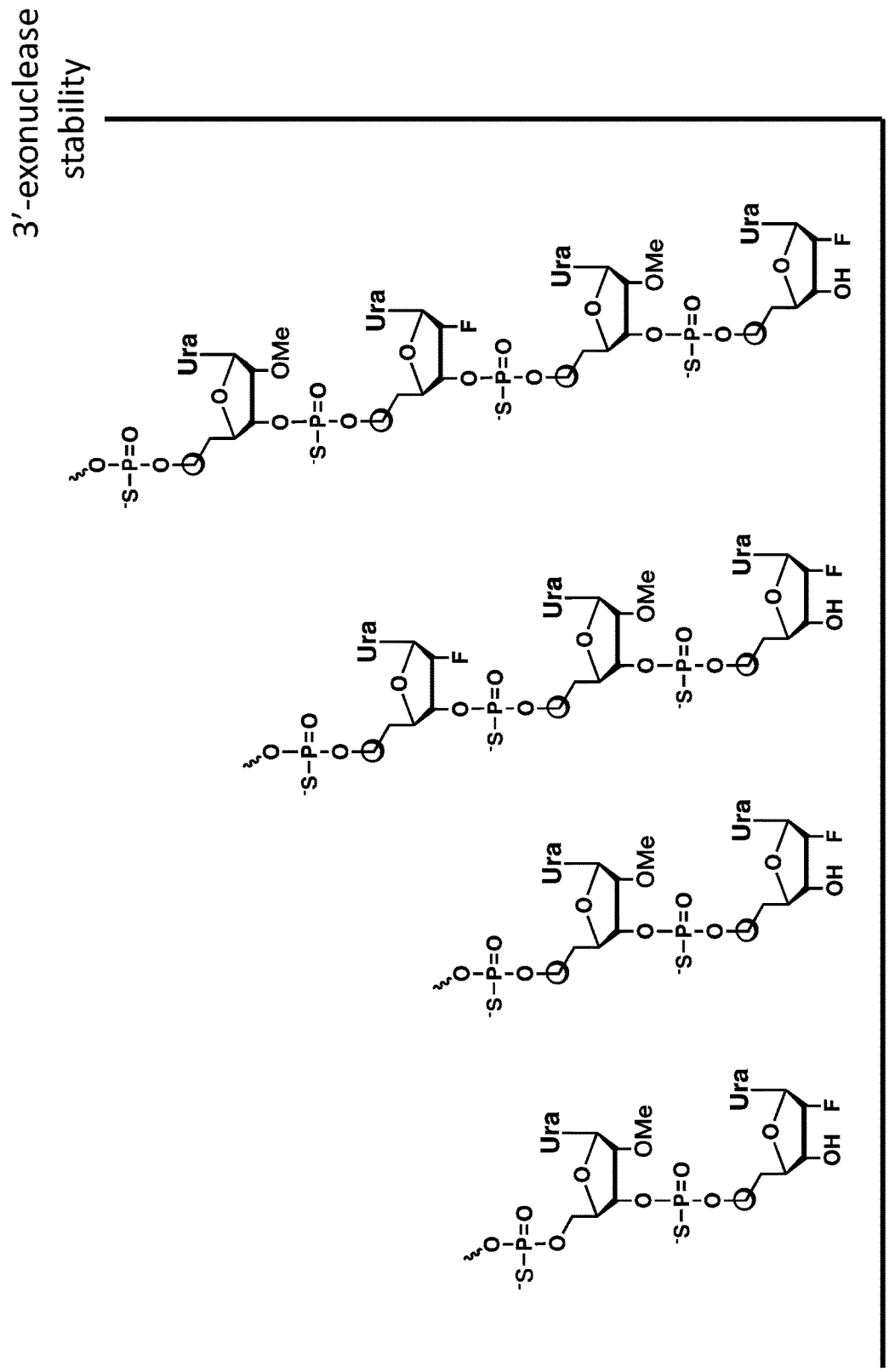
FIG. 15 provides a model depicting an increase in 3' exonuclease stability for oligonucleotides with increasing numbers of exNA and phosphorothioate intersubunit linkages.

Example 12 Nuclease Stability of siRNA Duplexes Containing exNA Intersubunit Linkages It was hypothesized that the ex-NA intersubunit linkage would be useful for increasing the nuclease stability of oligonucleotides. This effect may be observed with ex-NA intersubunit linkages alone or in combination with phosphorothioate intersubunit linkages. Moreover, multiple consecutive ex-NA intersubunit linkages in an oligonucleotide may have a greater impact on stability than a single ex-NA intersubunit linkage. There are two primary ways stability may be increased, 1) the aberrant local backbone structure of ex-NA lowers kinetics of nuclease cleavage, and 2) multiply extended backbones lower binding affinity of nucleases (poly-extension impact on whole structure of 3'-terminal region) (FIG. 15). To demonstrate this effect, several nuclease assays where employed with oligonucleotides containing one or more ex-NA intersubunit linkages.

3' Exonuclease Stability Test.

Figure 16:
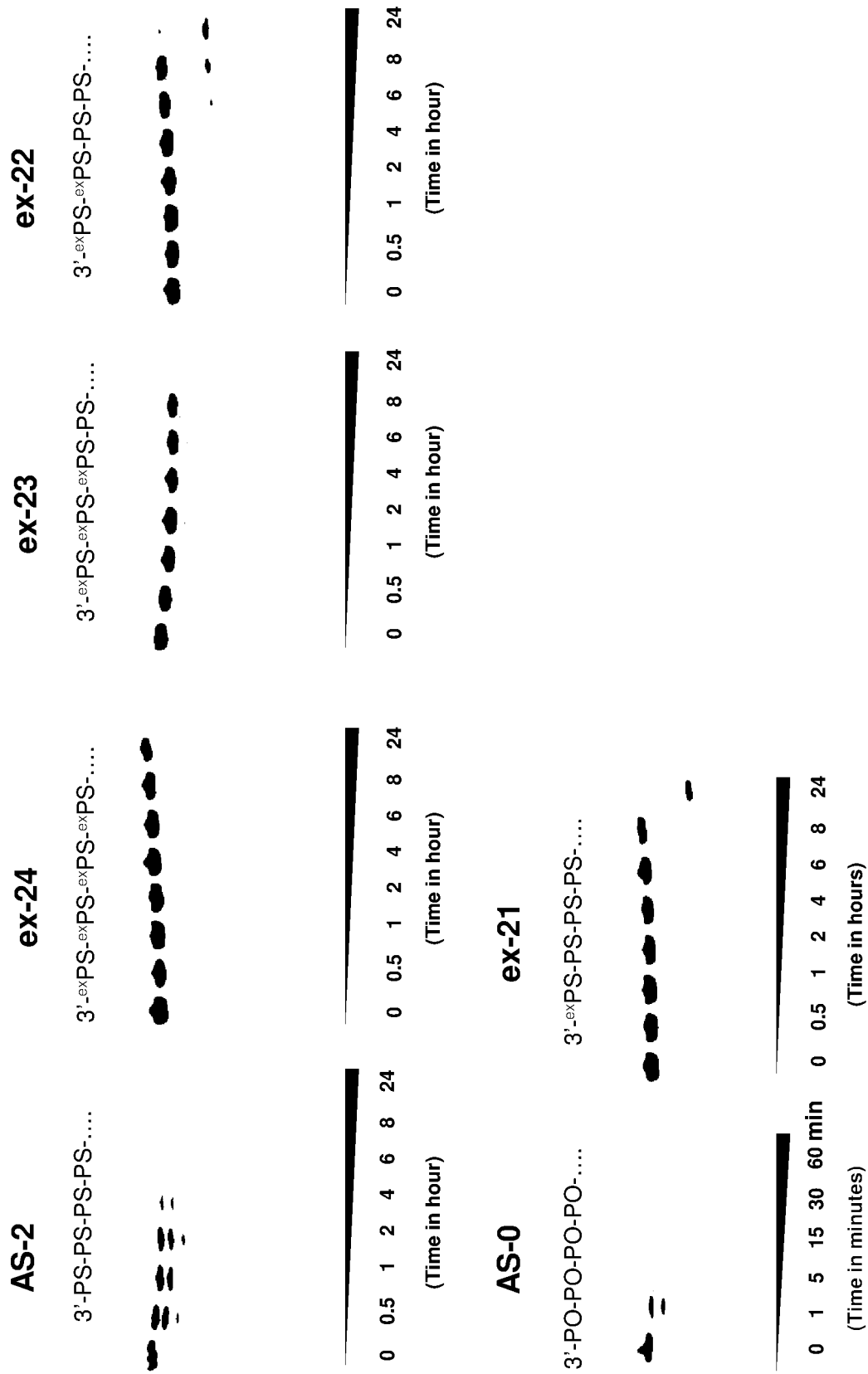
FIG. 16 provides results from a 3'-exonuclease stability test. Each oligonucleotide (17.5 mM) was incubated in a buffer containing 10 mM Tris-HCl (pH 8.0), 2 mM $MgCl_2$, and Snake Venom Phosphodiesterase I (20 mU/mL) at 37° C.

Oligonucleotides with a varying number of ex-NA intersubunit linkages at the 3' end were tested in a 3' exonuclease stability test. Oligonucleotides ex-21, ex-22, ex-23, ex-24, AS-0, and AS-2 (as recited above in Table 4 and Table 6) at a concentration of 17.5 mM were incubated in a buffer containing 10 mM Tris-HCl (pH 8.0), 2 mM $MgCl_2$, and Snake Venom Phosphodiesterase I (20 mU/mL) at 37° C. As shown in FIG. 16, multiple ex-NA intersubunit linkages with phosphorothioate intersubunit linkages (ex-24) drastically improved 3'-exonuclease stability compared to AS-2, which has the same phosphorothioate content found in clinically approved siRNA drugs. Moreover, even a single ex-NA intersubunit linkage at the 3' end dramatically improved stability (ex-21). As 3'-exonucleases are dominant in the serum, the 3' ex-NA intersubunit linkages are useful in therapeutic oligonucleotides.

Figure 17:
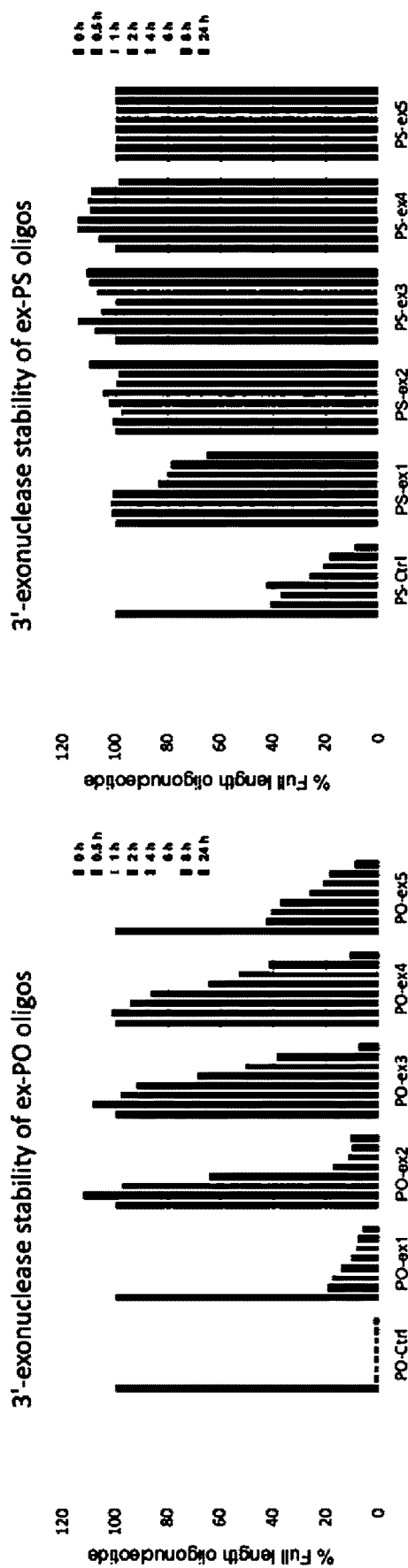
FIG. 17 provides results from a 3'-exonuclease stability test of ex-NA intersubunit linkages in a context of polyuridyl sequence with phosphodiester (PO) and phosphorothioate (PS) containing oligonucleotides. Oligonucleotides were tested with 1, 2, 3, 4, or 5 ex-NA intersubunit linkages.

An additional 3' exonuclease test was performed with ex-NA intersubunit linkages in a context of poly-uridyl sequence with phosphodiester (PO) and phosphorothioate (PS) containing oligonucleotides. Oligonucleotides were tested with 1, 2, 3, 4, or 5 ex-NA intersubunit linkages. Table 11 below recites the polynucleotides used in this test. As shown in FIG. 17, the presence of even a single ex-NA intersubunit linkage dramatically improved oligonucleotide stability. This was demonstrated in both the PO and PS oligonucleotides. Moreover, the PO-containing oligonucleotide with 5 ex-NA intersubunit linkages achieved similar nuclease stability compared the PS-containing oligonucleotide with no ex-NA intersubunit linkages (PS control). This result indicates that the number of PS-containing intersubunit linkages may be reduced if using ex-NA intersubunit linkages, thereby reducing toxicity associated with PS-containing oligonucleotides.

TABLE 11

Polyuridyl oligonucleotides for the 3'-exonuclease stability test

| Name | Sequence (5'->3')[a] | SEQ ID NO: |
|---|---|---|
| FAM-Ctrl-PO | 5'-FAM-(mU)(mU)(mU)(mU)(mU)(mU)(mU)(mU)(mU)(mU)(mU)(mU)(mU)(mU)(mU)(mU)(mU)(mU)(mU)(mU) | 52 |
| FAM-PO-ex1 | 5'-FAM-(mU)(mU)(mU)(mU)(mU)(mU)(mU)(mU)(mU)(mU)(mU)(mU)(mU)(mU)(mU)(mU)(mU)(mU)(mU)(ex-mU) | 53 |
| FAM-PO-ex2 | 5'-FAM-(mU)(mU)(mU)(mU)(mU)(mU)(mU)(mU)(mU)(mU)(mU)(mU)(mU)(mU)(mU)(mU)(mU)(mU)(ex-mU)(ex-mU) | 54 |
| FAM-PO-ex3 | 5'-FAM-(mU)(mU)(mU)(mU)(mU)(mU)(mU)(mU)(mU)(mU)(mU)(mU)(mU)(mU)(mU)(mU)(mU)(ex-mU)(ex-mU)(ex-mU) | 55 |
| FAM-PO-ex4 | 5'-FAM-(mU)(mU)(mU)(mU)(mU)(mU)(mU)(mU)(mU)(mU)(mU)(mU)(mU)(mU)(mU)(mU)(ex-mU)(ex-mU)(ex-mU)(ex-mU) | 56 |
| FAM-PO-ex5 | 5'-FAM-(mU)(mU)(mU)(mU)(mU)(mU)(mU)(mU)(mU)(mU)(mU)(mU)(mU)(mU)(mU)(ex-mU)(ex-mU)(ex-mU)(ex-mU)(ex-mU) | 57 |
| FAM-Ctrl-PS | 5'-FAM-(mU)(mU)(mU)(mU)(mU)(mU)(mU)(mU)(mU)(mU)(mU)(mU)(mU)(mU)(mU)(mU)#(mU)#(mU)#(mU)#(mU)#(mU) | 58 |
| FAM-PS-ex1 | 5'-FAM-(mU)(mU)(mU)(mU)(mU)(mU)(mU)(mU)(mU)(mU)(mU)(mU)(mU)(mU)(mU)(mU)#(mU)#(mU)#(mU)#(mU)#(ex-mU) | 59 |
| FAM-PS-ex2 | 5'-FAM-(mU)(mU)(mU)(mU)(mU)(mU)(mU)(mU)(mU)(mU)(mU)(mU)(mU)(mU)(mU)(mU)#(mU)#(mU)#(mU)#(ex-mU)#(ex-mU) | 60 |
| FAM-PS-ex3 | 5'-FAM-(mU)(mU)(mU)(mU)(mU)(mU)(mU)(mU)(mU)(mU)(mU)(mU)(mU)(mU)(mU)(mU)#(mU)#(mU)#(ex-mU)#(ex-mU)#(ex-mU) | 61 |
| FAM-PS-ex4 | 5'-FAM-(mU)(mU)(mU)(mU)(mU)(mU)(mU)(mU)(mU)(mU)(mU)(mU)(mU)(mU)(mU)(mU)#(mU)#(ex-mU)#(ex-mU)#(ex-mU)#(ex-mU) | 62 |
| FAM-PS-ex5 | 5'-FAM-(mU)(mU)(mU)(mU)(mU)(mU)(mU)(mU)(mU)(mU)(mU)(mU)(mU)(mU)(mU)(mU)#(ex-mU)#(ex-mU)#(ex-mU)#(ex-mU)#(ex-mU) | 63 |

[a](mU): 2'-OMe-uridine,
(ex-mU): 2'-OMe-ex-uridine,
Phosphorothioate,
FAM: 6-FAM fluorescein-label The fluorescein-label, "FAM" used on the oligonucleotides has no impact on 3' exonuclease activity and was used to monitor cleavage in the stability test.

5' Exonuclease Stability Test.

Oligonucleotides with an ex-NA intersubunit linkage at the 5' end were tested in two different 5' exonuclease stability tests.

Figure 18:
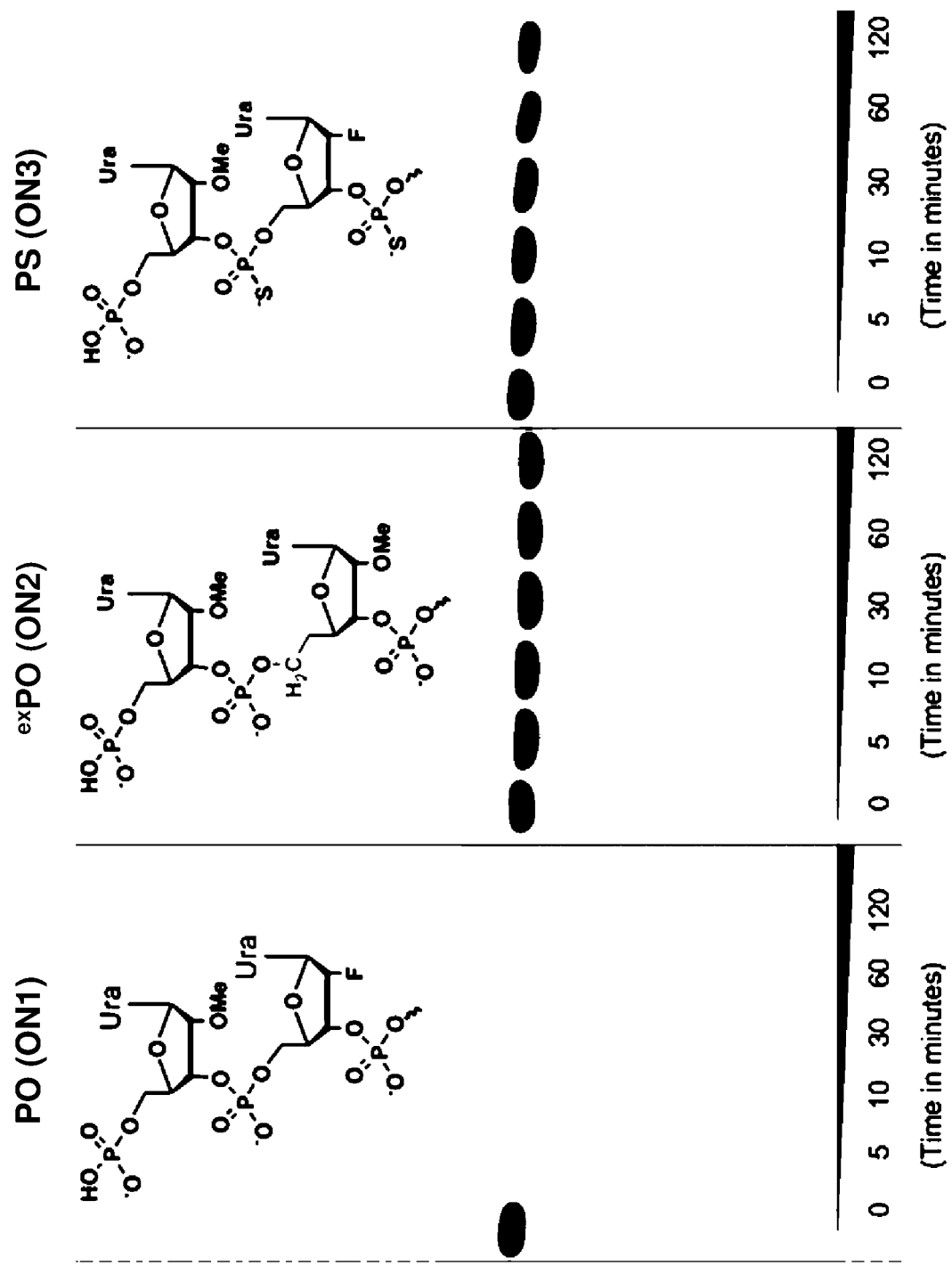
FIG. 18 provides results from a 5'-Phosphate-dependent 5'-exonuclease stability test. 2.5 µM (50 pmol) of each oligonucleotide was incubated in RNase-free water or with 3.3 Units of Terminator™ (EpiCentre) exonuclease at 37° C. in buffer A (EpiCentre, provided with Terminator™ enzyme).

The first test was a 5'-Phosphate-dependent 5'-exonuclease stability test. Oligonucleotides employed in this test are shown below in Table 12. Oligonucleotides were used at 2.5 µM (50 pmol) and were incubated in RNase-free water, or with 3.3 Unit of Terminator™ (EpiCentre) exonuclease at 37° C. in buffer A (EpiCentre, provided with Terminator™ enzyme). As shown in FIG. 18, a single ex-NA intersubunit linkage at the 5' end (ON2) drastically improved 5'-exonuclease stability compared to ON1, which contains a 5' phosphodiester linkage. Importantly, ON2 does not contain a phosphorothioate intersubunit linkage. The data demonstrates that a single ex-NA intersubunit linkage at the 5' end enhances stability to the same extent as multiple phosphorothioate intersubunit linkages at the 5' end (ON3). Excessive phosphorothioate content in therapeutic oligonucleotides can be toxic. The use of a 5' ex-NA intersubunit linkage provides a mechanism to improve oligonucleotide stability while reducing the phosphorothioate content.

Figure 19:
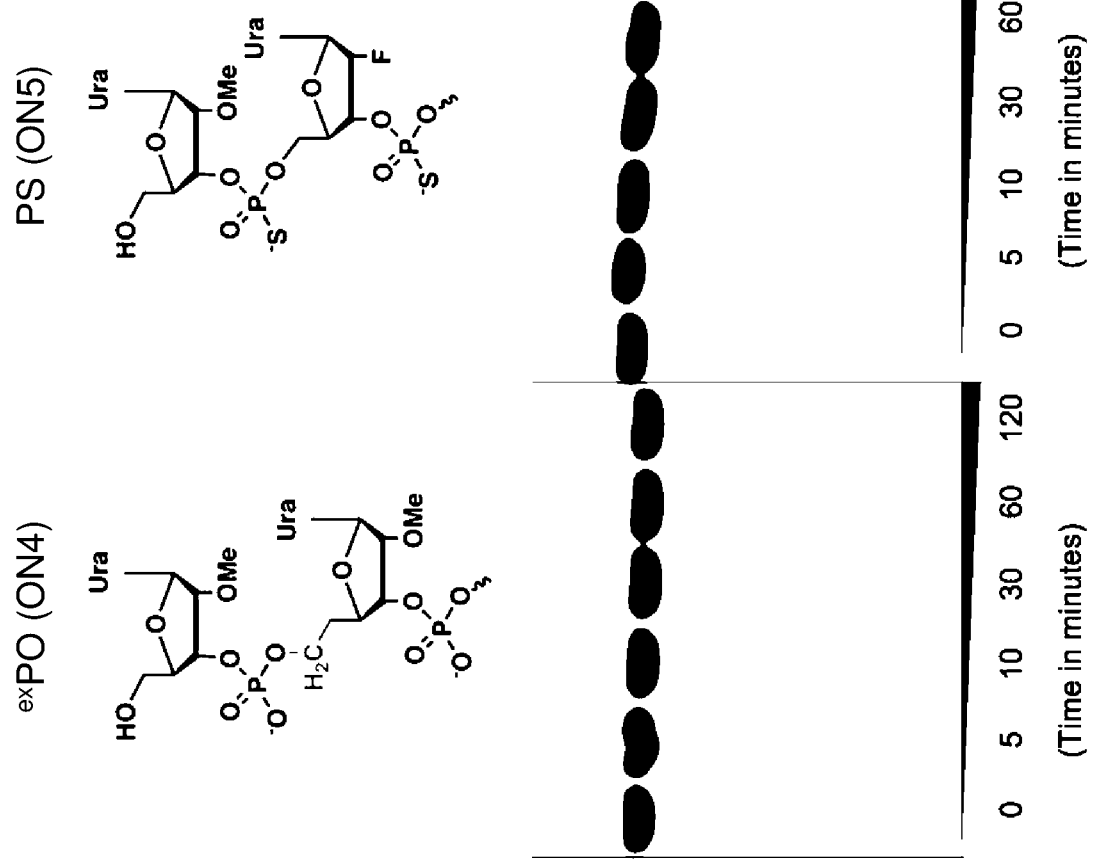
FIG. 19 provides results from a 5'-Phosphate-independent 5'-exonuclease stability test. Each oligonucleotide (10 µM) was incubated in RNase-free water or 30 mM NaOAc (pH 6.0) buffer containing 0.25 U/mL Bovine Spleen Phosphodiesterase II (BSP) at 37° C.
Figure 21E:
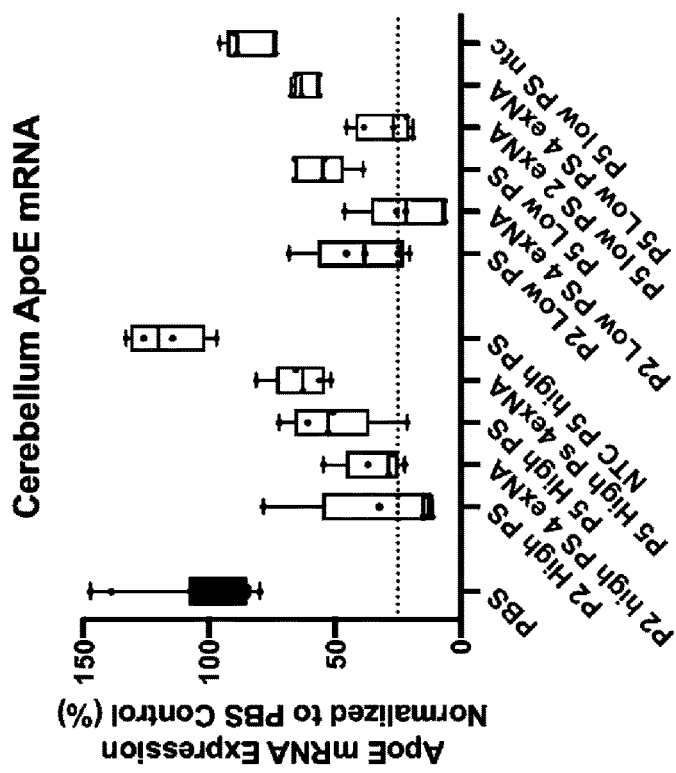
Figure 21D:
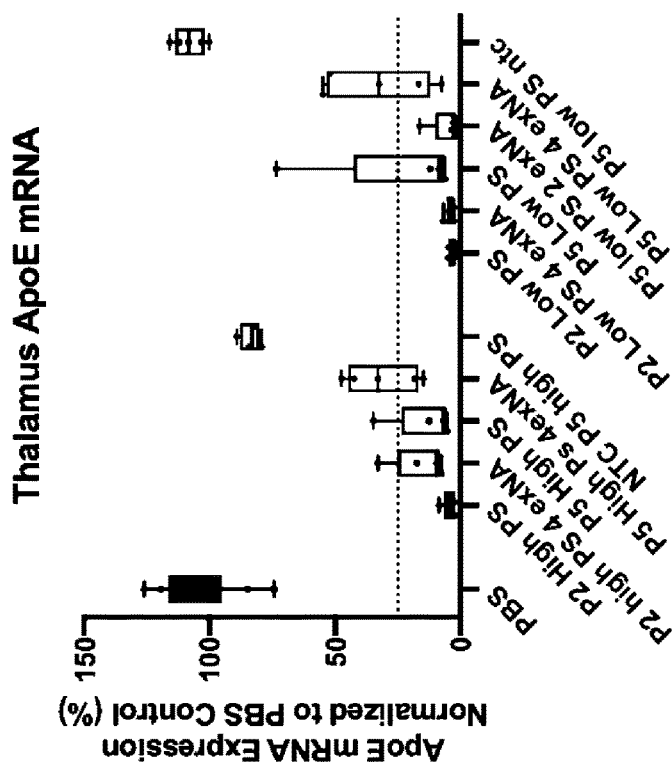

The second 5'-exonuclease stability test was a 5'-Phosphate-independent 5'-exonuclease stability test. Oligonucleotides employed in this test are shown below in Table 13. Oligonucleotides were used at 10 µM and were incubated in RNase-free water or with 30 mM NaOAc (pH 6.0) buffer containing 0.25 U/mL Bovine Spleen Phosphodiesterase II (BSP) at 37° C. As shown in FIG. 19, a single ex-NA intersubunit linkage at the 5' end (ON4) possess similar 5'-exonuclease stability compared to ON5, which contains multiple 5' phosphorothioate linkages. The data demonstrates that a single ex-NA intersubunit linkage at the 5' end enhances stability to the same extent as multiple phosphorothioate intersubunit linkages at the 5' end (ON5). Excessive phosphorothioate content in therapeutic oligonucleotides can be toxic. The use of a 5' ex-NA intersubunit linkage provides a mechanism to improve oligonucleotide stability while reducing the phosphorothioate content.

TABLE 12

Oligonucleotides for the 5'-Phosphate-dependent 5'-exonuclease stability test

| Name | Sequence (5'->3') | SEQ ID NO: |
|---|---|---|
| ON1 | 5'-P(mU)(fU)(mA)(fA)(mU)(fC)(mU)(fC)(mU)(fU)(mU)(fA)(mC)(fU)(mG)(fA)(mU)(fU)(mU)(mU) | 64 |
| ON2 | 5'-P (mU)(ex-mU)(mA)(fA)(mU)(fC)(mU)(fC)(mU)(fU)(mU)(fA)(mC)(fU)(mG)(fA)(mU)(fU)(mU)(ex-mU) | 65 |
| ON3 | 5'-P(mU)#(fU)#(mA)(fA)(mU)(fC)(mU)(fC)(mU)(fU)(mU)(fA)(mC)(fU)(mG)(fA)#(mU)#(fU)#(mU)#(mU) | 66 |

TABLE 13

Oligonucleotides for the 5'-Phosphate-independent 5'-exonuclease stability test

| Name | Sequence (5'->3') | SEQ ID NO: |
|---|---|---|
| ON4 | 5'-(mU)(ex-mU)(mA)(fA)(mU)(fC)(mU)(fC)(mU)(fU)(mU)(fA)(mC)(fU)(mG)(fA)(mU)(fU)(mU)(ex-mU) | 67 |
| ON5 | 5'-(mU)#(fU)#(mA)(fA)(mU)(fC)(mU)(fC)(mU)(fU)(mU)(fA)(mC)(fU)(mG)(fA)#(mU)#(fU)#(mU)#(mU) | 68 |

Example 13 Activity of siRNA Duplexes Containing One or More Antisense Strand 3' End exNA Intersubunit Linkages The in vitro silencing activity of several siRNA duplexes containing one or more antisense strand 3' end exNA intersubunit linkages was tested. An antisense strand comprising one, two, three, or four 3' end exNA intersubunit linkages was used in a dose response curve, as depicted in FIG. 20A. The percent potency change relative to an siRNA duplex control that does not contain an exNA intersubunit linkage was also determined (FIG. 20B). The data demonstrates that siRNA duplexes with antisense strands comprising one, two, three, or four 3' end exNA intersubunit linkages possess greater silencing efficacy than an siRNA duplex with an antisense strand lacking exNA intersubunit linkages.

Example 14 In Vivo Activity of siRNA Duplexes Containing One or More Antisense Strand 3' End exNA Intersubunit Linkages The in vivo silencing activity of several siRNA duplexes containing one or more antisense strand 3' end exNA intersubunit linkages was tested. The siRNA duplexes were in the Di-siRNA format, as described above. The sequences and chemical modification patterns are recited below in Table 14, each siRNA targeting ApoE mRNA. 5 nmol of each Di-siRNA was administered by ICV injection to mice, and ApoE mRNA was quantified 1 month later. As shown in FIG. 21A-FIG. 21E, exNA intersubunit linkage-containing siRNAs were capable of silencing ApoE in several brain regions (medial cortex, striatum, hippocampus, thalamus, and cerebellum). The silencing efficacy of siRNA duplexes containing a low phosphorothioate (PS) content was approximately maintained or improved with the inclusion of exNA intersubunit linkages.

TABLE 14

Anti-ApoE siRNA sequences used in Example 14 and FIG. 21. Table 14 discloses SEQ ID NOS 69-73, 70, 74, 72, 75, 70, 76, 72, 77, 72, 78, 70, 79, 72, 80-81, 82, and 81, respectively, in order of appearance.

| | CHEM | PS | Duplex # | Oligo name | Sequence |
|---|---|---|---|---|---|
| Control | P5_Ctrl | Low | 1 | AP-Ctrl-G1 | VP(mu)#(fU)#(mG)(mG)(mA)(fU)(mA)(mU)(mG)(mG)(mA)(mU)(mG)(fU)(mU)(fG)(mU)(mU)(mU)#(mU)#(mU) |
| | | | | #10928 | (mC)#(mA)#(mA)(mC)(mA)(mU)(mC)(fC)(mA)(fU)(fA)(fU)(mC)(mC)#(mA)#(mA)-Dio |
| | P2_Ctrl | Low | 2 | AP-Ctrl-G2 | VP(mu)#(fU)#(mG)(fG)(mA)(fU)(mA)(fU)(mG)(fG)(mA)(fU)(mG)(fU)(mU)(fG)(mU)(mU)(mU)#(mU)#(mU) |
| | | | | #10926 | (mC)#(fA)#(mA)(fC)(mA)(fU)(mC)(fC)(mA)(fU)(mA)(fU)(mC)(fC)#(mA)#(mA)-Dio |
| | P5_Ctrl | High | 3 | #10279 | V(mu)#(fU)#(mG)(mG)(mA)(fU)(mA)(mU)(mG)(mG)(mA)(mU)(mG)(fU)#(mU)#(fG)#(mU)#(mU)#(mU)#(mU)#(mU) |
| | | | | #10928 | (mC)#(fA)#(mA)(mC)(mA)(mU)(mC)(fC)(mA)(fU)(fA)(fU)(mC)(mC)#(mA)#(mA)-Dio |
| | P2_Ctrl | High | 4 | #10280 | V(mu)#(fU)#(mG)(fG)(mA)(fU)(mA)(fU)(mG)(fG)(mA)(fU)(mG)(fU)#(mU)#(fG)#(mU)#(mU)#(mU)#(mU)#(mU) |
| | | | | #10926 | (mC)#(fA)#(mA)(fC)(mA)(fU)(mC)(fC)(mA)(fU)(mA)(fU)(mC)(fC)#(mA)#(mA)-Dio |
| exNA | P5_ex | Low | 5 | AP-ex-G1 | VP(mu)#(fU)#(mG)(mG)(mA)(fU)(mA)(mU)(mG)(mG)(mA)(mU)(mG)(fU)(mU)(fG)(mU)(ex-mU)(ex-mU)#(ex-mU) |
| | | | | #10928 | (mC)#(mA)#(mA)(mC)(mA)(mU)(mC)(fC)(mA)(fU)(fA)(fU)(mC)(mC)#(mA)#(mA)-Dio |
| | P5_ex | Low | 6 | AP-ex-G2 | VP(mu)#(fU)#(mG)(mG)(mA)(fU)(mA)(mU)(mG)(mG)(mA)(mU)(mG)(fU)(mU)(fG)(mU)(mU)(mU)#(ex-mU)#(ex-mU) |
| | | | | #10926 | (mC)#(fA)#(mA)(fC)(mA)(fU)(mC)(fC)(mA)(fU)(mA)(fU)(mC)(fC)#(mA)#(mA)-Dio |
| | P2_ex | Low | 7 | AP-ex-G3 | VP(mu)#(fU)#(mG)(fG)(mA)(fU)(mA)(fU)(mG)(fG)(mA)(fU)(mG)(fU)(mU)(fG)(mU)(ex-mU)(ex-mU)#(ex-mU) |
| | | | | #10926 | (mC)#(fA)#(mA)(fC)(mA)(fU)(mC)(fC)(mA)(fU)(mA)(fU)(mC)(fC)#(mA)#(mA)-Dio |
| | P5_ex | High | 8 | #10277 | VP(mu)#(fU)#(mG)(mG)(mA)(fU)(mA)(mU)(mG)(mG)(mA)(mU)(mG)(fU)#(mU)#(fG)#(mU)#(ex-mU)#(ex-mU)#(ex-mU)#(ex-mU) |
| | | | | #10928 | (mC)#(mA)#(mA)(mC)(mA)(mU)(mC)(fC)(mA)(fU)(fA)(fU)(mC)(mC)#(mA)#(mA)-Dio |
| | P2_ex | High | 9 | #10278 | VP(mu)#(fU)#(mG)(fG)(mA)(fU)(mA)(fU)(mG)(fG)(mA)(fU)(mG)(fU)#(mU)#(fG)#(mU)#(ex-mU)(ex-mU)#(ex-mU)#(ex-mU) |
| | | | | #10926 | (mC)#(fA)#(mA)(fC)(mA)(fU)(mC)(fC)(mA)(fU)(mA)(fU)(mC)(fC)#(mA)#(mA)-Dio |
| NTC | P5_ex | Low | 10 | AP-NTC G | VP(mu)#(fA)#(mA)(mU)(mC)(fG)(mU)(mA)(mU)(mU)(mU)(mG)(mU)(fC)(mA)(fA)(mU)(ex-mU)#(ex-mU)#(ex-mU) |
| | | | | #8419 | (mU)#(mU)#(mG)(mA)(mC)(fA)(fA)(fA)(mU)(fA)(mC)(mG)(mA)(mU)#(mU)#(mA)-Dio |
| | P5_ex | High | 11 | #10281 | VP(mu)#(fA)#(mA)(mU)(mC)(fG)(mU)(mA)(mU)(mU)(mU)(mG)(mU)(fC)#(mA)#(fA)#(mU)#(ex-mU)#(ex-mU)#(ex-mU)#(ex-mU) |
| | | | | #8419 | (mU)#(mU)#(mG)(mA)(mC)(fA)(fA)(fA)(mU)(fA)(mC)(mG)(mA)(mU)#(mU)#(mA)-Dio |

An additional in vivo silencing activity experiment was performed, with Di-sRNA duplexes targeting Htt mRNA. The chemical modification patterns employed are recited below. Wild type male mice treated with ~60 µg of siRNA for 2 months, followed by quantification of Htt mRNA and protein levels in several brain regions (medial cortex, striatum, hippocampus, thalamus, and frontal cortex). The siRNA duplexes with antisense strands containing one or two exNA internucleotide linkages displayed equal or greater silencing of Htt mRNA (FIG. 22A-FIG. 22E) and protein (FIG. 23A-FIG. 23E) expression compared to siRNA duplexes lacking exNA internucleotide linkages. The exNA internucleotide linkage, which confers greater nuclease resistance than the phosphorothioate modification, permits the reduction of toxic phosphorothioate modifications without sacrificing nuclease resistance or silencing efficacy. Chemical modification patterns used in FIG. 22 and FIG. 23:

1—High PS:
Antisense strand (5' to 3'):
VP(m,X) #(fX) #(mX)(fX)(fX)(fX)(mX)(fX)(mX)(fX) (mX)(fX)(mX)(fX) #(mX) #(fX) #(miX) #(mX) #(mX) #(fX) #(mX)
Sense strand (5' to 3'):
(mX) #(mX) #(mX)(fX)(mX)(fX)(mX)(fX)(mX)(fX)(mX) (mX)(mX)(fX) #(mX) #(mX)

2-Low PS fm:
Antisense strand (5' to 3'):
VP(mX) #(fX) #(mX)(fX)(fX)(fX)(mX)(fX)(mX)(fX)(mX) (fX)(mX)(fX)(mX)(fX)(mX)(mX)(mX) #(fX) #(mX)
Sense strand (5' to 3'):
(mX) #(mX) #(mX)(fX)(mX)(fX)(mX)(fX)(mX)(fX)(mX) (mX)(mX)(fX) #(mX) #(mX)

3—Low PS mf:
Antisense strand (5' to 3'):
VP(mX) #(fX) #(mX)(fX)(fX)(fX)(mX)(fX)(mX)(fX)(mX) (fX)(niX)(fX)(mX)(fX)(mX)(niX)(mX) #(mX) #(fX)
Sense strand (5' to 3'):
(mX) #(mX) #(mX)(fX)(mX)(fX)(mX)(fX)(mX)(fX)(mX) (mX)(mX)(fX) #(mX) #(mX)

4-Low PS mf 2 exNA:
Antisense strand (5' to 3'):
VP(mX) #(fX) #(mX)(fX)(fX)(fX)(mX)(fX)(mX)(fX)(mX) (fX)(mX)(fX)(mX)(fX)(niX)(niX)(mX) #(ex-mX) #(ex-fX)
Sense strand (5' to 3'):
(mX) #(mX) #(mX)(fX)(mX)(fX)(mX)(fX)(mX)(fX)(mX) (mX)(mX)(fX) #(mX) #(mX)

5—Low PS mf 1 exNA:
Antisense strand (5' to 3'):
VP(mX) #(fX) #(mX)(fX)(fX)(fX)(mX)(fX)(mX)(fX)(mX) (fX)(mX)(fX)(mX)(fX)(niX)(niX)(mX) #(mX) #(ex-fX)
Sense strand (5' to 3'):
(mX) #(mX) #(mX)(fX)(mX)(fX)(mX)(fX)(mX)(fX)(mX) (mX)(mX)(fX) #(mX) #(mX)

For the above recited 5 chemical modification patterns, "VP" corresponds to a 5' vinyl phosphonate; "mX" corresponds to any nucleotide (A, U, G, or C) with a 2'-O-methyl modification; "fX" corresponds to any nucleotide (A, U, G, or C) with a 2'-fluoro modification; "#" corresponds to a phosphorothioate modification; "ex-mX" corresponds to any nucleotide (A, U, G, or C) with a 2'-O-methyl modification and exNA internucleotide linkage; and "ex-fX" corresponds to any nucleotide (A, U, G, or C) with a 2'-fluoro modification and exNA internucleotide linkage.

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;

Ausubel et al. (eds.), CURRENT PROTOCOLS IN MOLECULAR BIOLOGY, John Wiley &Sons, N Y (1993);

Ausubel, F. M. et al. eds., SHORT PROTOCOLS IN MOLECULAR BIOLOGY (4th Ed. 1999) John Wiley & Sons, NY. (ISBN 0-471-32938-X);

CONTROLLED DRUG BIOAVAILABILITY, DRUG PRODUCT DESIGN AND PERFORMANCE, Smolen and Ball (eds.), Wiley, New York (1984);

Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, New York, (1999);

Goodson, in MEDICAL APPLICATIONS OF CONTROLLED RELEASE, vol. 2, pp. 115-138 (1984);

Hammerling, et al., in: MONOCLONAL ANTIBODIES AND T-CELL HYBRIDOMAS 563-681 (Elsevier, N.Y., 1981;

Harlow et al., ANTIBODIES: A LABORATORY MANUAL, (Cold Spring Harbor Laboratory Press, 2nd ed. 1988);

Kabat et al., SEQUENCES OF PROTEINS OF IMMUNOLOGICAL INTEREST (National Institutes of Health, Bethesda, Md. (1987) and (1991);

Kabat, E. A., et al. (1991) SEQUENCES OF PROTEINS OF IMMUNOLOGICAL INTEREST, Fifth Edition, U.S. Department of Health and Human Services, NIH Publication No. 91-3242;

Kontermann and Dubel eds., ANTIBODY ENGINEERING (2001) Springer-Verlag. New York. 790 pp. (ISBN 3-540-41354-5).

Kriegler, Gene Transfer and Expression, A Laboratory Manual, Stockton Press, N Y (1990); Lu and Weiner eds., CLONING AND EXPRESSION VECTORS FOR GENE FUNCTION ANALYSIS (2001) BioTechniques Press. Westborough, MA 298 pp. (ISBN 1-881299-21-X). MEDICAL APPLICATIONS OF CONTROLLED RELEASE, Langer and Wise (eds.), CRC Pres., Boca Raton, Fla. (1974);

Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V.2:409 pp. (ISBN 0-632-01318-4).

Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6).

SUSTAINED AND CONTROLLED RELEASE DRUG DELIVERY SYSTEMS, J. R. Robinson, ed., Marcel Dekker, Inc., New York, 1978

Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed is:

1. A modified oligonucleotide comprising a 5' end, a 3' end and at least one modified intersubunit linkage of Formula I:

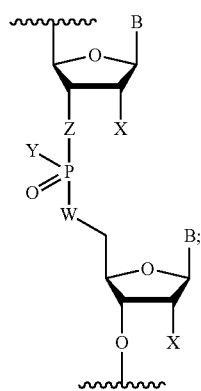

wherein:

B is a base pairing moiety;

W is O or $O(CH_2)_n$, wherein n is 1 to 10;

X is selected from the group consisting of H, OH, OR, F, SH, SR, $NR^2_2$ and $C_{1-6}$-alkoxy;

Y is selected from the group consisting of $O^-$, OH, OR, $OR^2$, $NH^-$, $NH_2$, $NR^2_2$, $BH_3$, $S^-$, $R^1$, and SH;

Z is $O(CH_2)_n$, wherein n is 1 to 10 and the oxygen from the $O(CH_2)_n$ is bonded to the phosphorus from the Formula I;

R is a substituted or unsubstituted $C_{1-6}$ alkyl, alkenyl, alkynyl, or aryl;

$R^1$ is alkyl, allyl or aryl; and $R^2$ is alkyl, allyl or aryl.

2. The modified oligonucleotide of claim 1, wherein the base pairing moiety B is selected from the group consisting of adenine, guanine, cytosine, and uracil.

3. The modified oligonucleotide of claim 2, wherein Y is O.

4. The modified oligonucleotide of claim 1 wherein the at least one modified intersubunit linkage of Formula I comprises Formula III:

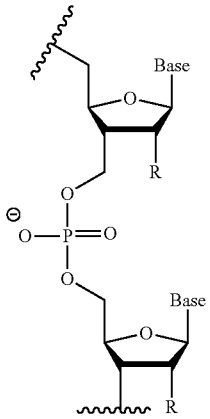

(III)

wherein:
  B is a base pairing moiety;
  R is alkyl, allyl or aryl.

5. The modified oligonucleotide of claim 4, wherein the base pairing moiety B is selected from the group consisting of adenine, guanine, cytosine, and uracil.

6. The modified oligonucleotide of claim 1 wherein the at least one modified intersubunit linkage of Formula I comprises Formula IV:

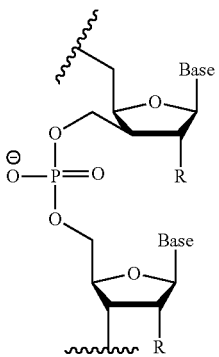

(IV)

wherein:
  B is a base pairing moiety;
  R is alkyl, allyl or aryl.

7. The modified oligonucleotide of claim 6, wherein the base pairing moiety B is selected from the group consisting of adenine, guanine, cytosine, and uracil.

8. The modified oligonucleotide of claim 1 wherein the at least one modified intersubunit linkage of Formula I comprises Formula V:

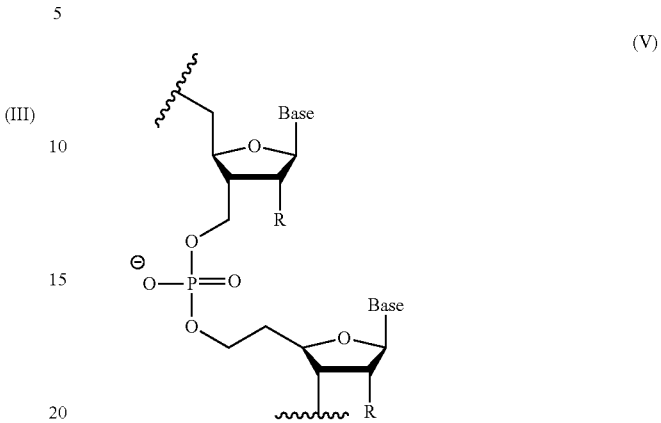

(V)

wherein:
  B is a base pairing moiety;
  R is alkyl, allyl or aryl.

9. The modified oligonucleotide of claim 8, wherein the base pairing moiety B is selected from the group consisting of adenine, guanine, cytosine, and uracil.

10. The modified oligonucleotide of claim 1 wherein the at least one modified intersubunit linkage of Formula I comprises Formula VI:

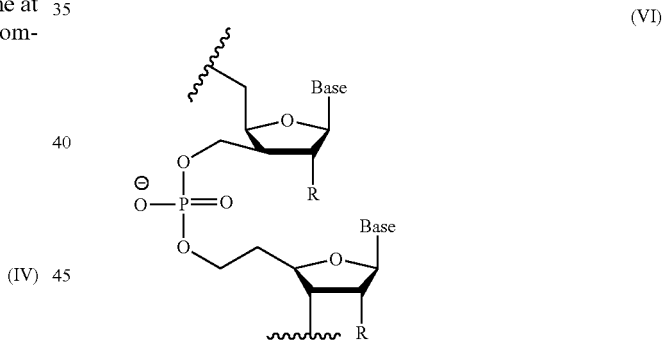

(VI)

wherein:
  B is a base pairing moiety;
  R is alkyl, allyl or aryl.

11. The modified oligonucleotide of claim 10, wherein the base pairing moiety B is selected from the group consisting of adenine, guanine, cytosine, and uracil.

12. The modified oligonucleotide of claim 1, wherein Z is $O(CH_2)_n$, n is 1, W is O, and Y is $O^-$.

13. The modified oligonucleotide of claim 1, wherein Z is $O(CH_2)_n$,
  n is 1, W is $O(CH_2)_n$, and Y is $O^-$.

14. The modified oligonucleotide of claim 1, wherein Z is $O(CH_2)_n$, n is not 1, W is $O(CH_2)_n$, and Y is $O^-$.

15. A method for synthesizing the modified oligonucleotide of claim 1, the method comprising:

(a) providing a nucleoside having a 5'-protecting group linked to a solid support;
(b) removal of the protecting group;
(c) combining the deprotected nucleoside with a phosphoramidite derivative of Formula (VII) to form a phosphite triester;

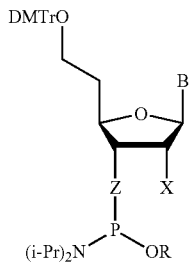

(VII)

(d) capping the phosphite triester;
(e) oxidizing the phosphite triester;
(f) repeating steps (b) through (e) using an additional phosphoramidite; and
(g) cleaving from the solid support;
wherein B, Z, X and R are defined as in Formula (I).

16. A method for synthesizing the modified oligonucleotide of claim 1, the method comprising coupling a phosphoramidite derivative of Formula (VII)

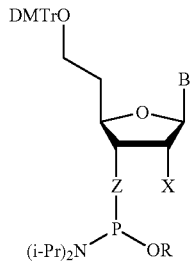

(VII)

to a 5'-terminus of a nucleoside or an oligonucleotide by adding the phosphoramidite derivative of Formula (VII) to the nucleoside or the oligonucleotide in an organic solvent comprising an aromatic heterocyclic acid; wherein B, Z, X and R are defined as in Formula (I).

17. A method for synthesizing the modified oligonucleotide of claim 1, the method comprising:
(a) providing a nucleoside having 3'-protecting group;
(b) oxidizing 5'-hydroxyl group of the nucleoside to a 5'-aldehyde group;
(c) converting 5'-aldehyde group of the nucleoside to a 5'-vinyl group by Wittig olefination;
(d) conducting hydroboration/oxidation on the 5'-vinyl group to produce a 6'-hydroxyl group;
(e) protecting the 6'-hydroxyl group with a DMTr group;
(f) removing the 3'-protecting group of the nucleoside; and
(g) phosphitylating 3'-hydroxyl group to produce a 3'-phosphoramidite,
thereby synthesizing the modified oligonucleotide.

* * * * *